(12) United States Patent
Kim et al.

(10) Patent No.: US 10,220,098 B2
(45) Date of Patent: Mar. 5, 2019

(54) ARTIFICIALLY ENGINEERED PROTEIN HYDROGELS TO MIMIC NUCLEOPORIN SELECTIVE GATING

(71) Applicant: Massachusetts Institute of Technology, Cambridge, MA (US)

(72) Inventors: Minkyu Kim, Melrose, MA (US); Bradley D. Olsen, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/320,520

(22) PCT Filed: Jun. 19, 2015

(86) PCT No.: PCT/US2015/036739
§ 371 (c)(1),
(2) Date: Dec. 20, 2016

(87) PCT Pub. No.: WO2015/196101
PCT Pub. Date: Dec. 23, 2015

(65) Prior Publication Data
US 2017/0304457 A1  Oct. 26, 2017

Related U.S. Application Data

(60) Provisional application No. 62/015,012, filed on Jun. 20, 2014.

(51) Int. Cl.
*C07K 14/47* (2006.01)
*A61K 47/42* (2017.01)
*A61K 9/06* (2006.01)
*A61K 9/00* (2006.01)

(52) U.S. Cl.
CPC .............. *A61K 47/42* (2013.01); *A61K 9/06* (2013.01); *C07K 14/47* (2013.01); *A61K 9/0024* (2013.01)

(58) Field of Classification Search
None
See application file for complete search history.

(56) References Cited

PUBLICATIONS

Frey et al., Science, vol. 314, No. 3, pp. 815-817, Nov. 2006.*
Ngo et al. in The Protein Folding Problem and Tertiary Structure Prediction, 1994, Merz et al. (ed.), Birkhauser, Boston, MA, pp. 433 and 492-495.*
Kim et al. Advanced Materials, vol. 27, pp. 4207-4212, 2015.*
Olsen et al., Macromolecules vol. 43, pp. 9094-9099, 2010.*

* cited by examiner

*Primary Examiner* — Richard G Hutson
(74) *Attorney, Agent, or Firm* — Foley Hoag LLP

(57) ABSTRACT

Disclosed are synthetic polypeptides modeled after NspI nucleoporin which are useful for forming hydrogels characterized by selective permeability. The polypeptides and hydrogels formed from them include phenylalanine-glycine (FG) repeats, which are believed to participate in the selectivity of the nuclear pore complex. Also disclosed are filtering devices, drug delivery devices, and methods of separating or selectively filtering macromolecules using the hydrogels.

23 Claims, 16 Drawing Sheets
Specification includes a Sequence Listing.

Figure 7A – 7G
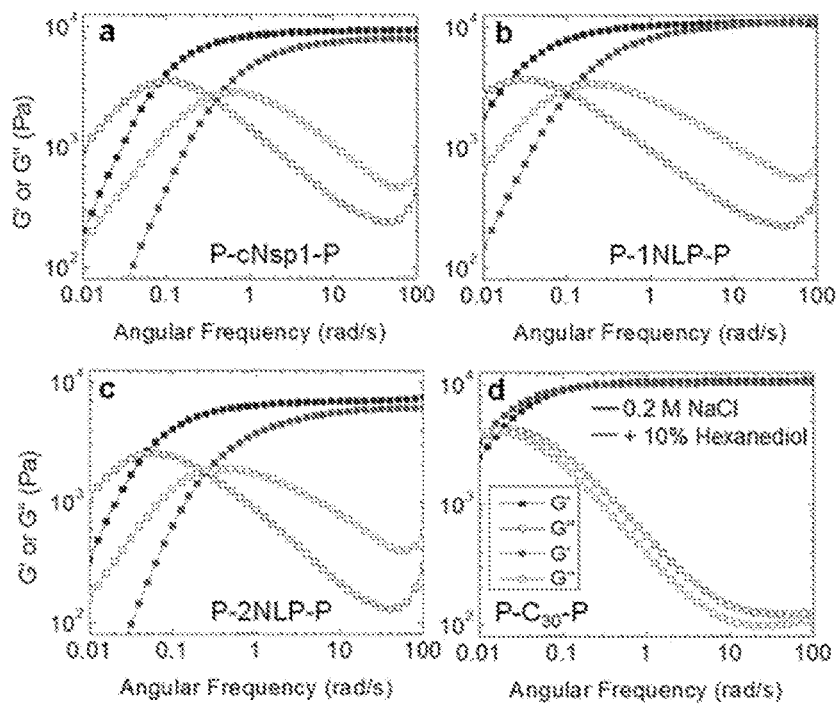
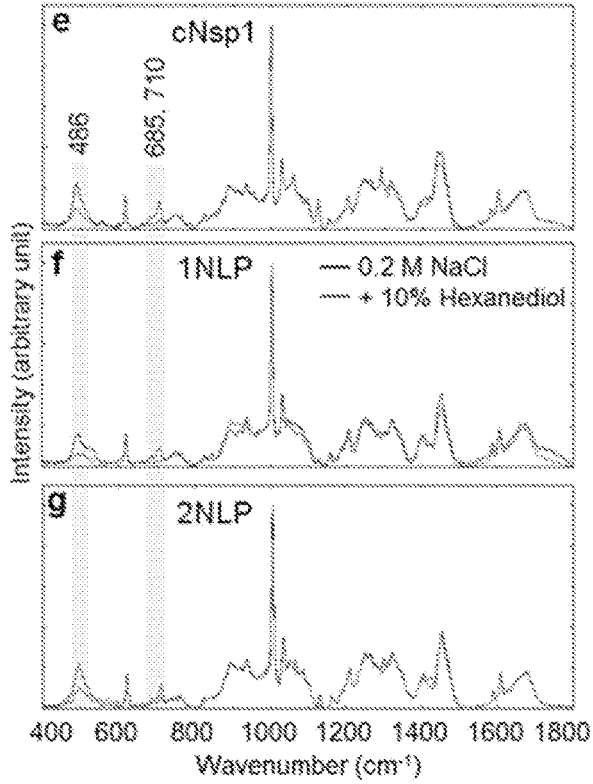

```
                        SEQUENCE LISTING

<160> NUMBER OF SEQ ID NOS: 30

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Ala Phe Ser Phe Gly Ala Lys Pro Asp Glu Lys Lys Asp Ser Asp
1               5                   10                  15

Thr Ser Lys

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Ala Phe Ser Phe Gly Ala Lys Pro Asp Glu Lys Lys Asp Asp Asp
1               5                   10                  15

Thr Ser Lys

<210> SEQ ID NO 3
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Pro Gln Met Leu Arg Glu Leu Gln Glu Thr Asn Ala Ala Leu Gln
```

```
                1               5                  10                 15
        Asp Val Arg Glu Leu Leu Arg Gln Gln Val Lys Glu Ile Thr Phe Leu
                        20                  25                 30

Lys Asn Thr Val Met Glu Ser Asp Ala Ser
                        35                  40

<210> SEQ ID NO 4
<211> LENGTH: 395
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Pro Gln Met Leu Arg Glu Leu Gln Glu Thr Asn Ala Ala Leu Gln
1               5                   10                  15

Asp Val Arg Glu Leu Leu Arg Gln Gln Val Lys Glu Ile Thr Phe Leu
            20                  25                  30

Lys Asn Thr Val Met Glu Ser Asp Ala Ser Gly Ala Ser Pro Ala Phe
        35                  40                  45

Ser Phe Gly Ala Lys Pro Asp Glu Lys Lys Asp Ser Asp Thr Ser Lys
    50                  55                  60

Pro Ala Phe Ser Phe Gly Ala Lys Pro Asp Glu Lys Lys Asp Ser Asp
65                  70                  75                  80

Thr Ser Lys Pro Ala Phe Ser Phe Gly Ala Lys Pro Asp Glu Lys Lys
                85                  90                  95

Asp Ser Asp Thr Ser Lys Pro Ala Phe Ser Phe Gly Ala Lys Pro Asp
            100                 105                 110

Glu Lys Lys Asp Ser Asp Thr Ser Lys Pro Ala Phe Ser Phe Gly Ala
        115                 120                 125

Lys Pro Asp Glu Lys Lys Asp Ser Asp Thr Ser Lys Pro Ala Phe Ser
    130                 135                 140

Phe Gly Ala Lys Pro Asp Glu Lys Lys Asp Ser Asp Thr Ser Lys Pro
145                 150                 155                 160

Ala Phe Ser Phe Gly Ala Lys Pro Asp Glu Lys Lys Asp Ser Asp Thr
                165                 170                 175

Ser Lys Pro Ala Phe Ser Phe Gly Ala Lys Pro Asp Glu Lys Lys Asp
            180                 185                 190

Ser Asp Thr Ser Lys Thr Ser Pro Ala Phe Ser Phe Gly Ala Lys Pro
        195                 200                 205

Asp Glu Lys Lys Asp Ser Asp Thr Ser Lys Pro Ala Phe Ser Phe Gly
    210                 215                 220

Ala Lys Pro Asp Glu Lys Lys Asp Ser Asp Thr Ser Lys Pro Ala Phe
225                 230                 235                 240

Ser Phe Gly Ala Lys Pro Asp Glu Lys Lys Asp Ser Asp Thr Ser Lys
                245                 250                 255

Pro Ala Phe Ser Phe Gly Ala Lys Pro Asp Glu Lys Lys Asp Ser Asp
            260                 265                 270

Thr Ser Lys Pro Ala Phe Ser Phe Gly Ala Lys Pro Asp Glu Lys Lys
        275                 280                 285

Asp Ser Asp Thr Ser Lys Pro Ala Phe Ser Phe Gly Ala Lys Pro Asp
    290                 295                 300

Glu Lys Lys Asp Ser Asp Thr Ser Lys Pro Ala Phe Ser Phe Gly Ala
305                 310                 315                 320
```

```
Lys Pro Asp Glu Lys Lys Asp Ser Asp Thr Ser Lys Pro Ala Phe Ser
            325                 330                 335

Phe Gly Ala Lys Pro Asp Glu Lys Lys Asp Ser Asp Thr Ser Lys Thr
            340                 345                 350

Ser Ala Pro Gln Met Leu Arg Glu Leu Gln Glu Thr Asn Ala Ala Leu
            355                 360                 365

Gln Asp Val Arg Glu Leu Leu Arg Gln Gln Val Lys Glu Ile Thr Phe
    370                 375                 380

Leu Lys Asn Thr Val Met Glu Ser Asp Ala Ser
385                 390                 395

<210> SEQ ID NO 5
<211> LENGTH: 395
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ala Pro Gln Met Leu Arg Glu Leu Gln Glu Thr Asn Ala Ala Leu Gln
1               5                   10                  15

Asp Val Arg Glu Leu Leu Arg Gln Gln Val Lys Glu Ile Thr Phe Leu
            20                  25                  30

Lys Asn Thr Val Met Glu Ser Asp Ala Ser Gly Ala Ser Pro Ala Phe
            35                  40                  45

Ser Phe Gly Ala Lys Pro Asp Glu Lys Lys Asp Asp Thr Ser Lys
    50                  55                  60

Pro Ala Phe Ser Phe Gly Ala Lys Pro Asp Glu Lys Lys Asp Asp
65                  70                  75                  80

Thr Ser Lys Pro Ala Phe Ser Phe Gly Ala Lys Pro Asp Glu Lys Lys
            85                  90                  95

Asp Asp Asp Thr Ser Lys Pro Ala Phe Ser Phe Gly Ala Lys Pro Asp
        100                 105                 110

Glu Lys Lys Asp Asp Asp Thr Ser Lys Pro Ala Phe Ser Phe Gly Ala
        115                 120                 125

Lys Pro Asp Glu Lys Lys Asp Asp Asp Thr Ser Lys Pro Ala Phe Ser
        130                 135                 140

Phe Gly Ala Lys Pro Asp Glu Lys Lys Asp Asp Asp Thr Ser Lys Pro
145                 150                 155                 160

Ala Phe Ser Phe Gly Ala Lys Pro Asp Glu Lys Lys Asp Asp Asp Thr
            165                 170                 175

Ser Lys Pro Ala Phe Ser Phe Gly Ala Lys Pro Asp Glu Lys Lys Asp
            180                 185                 190

Asp Asp Thr Ser Lys Thr Ser Pro Ala Phe Ser Phe Gly Ala Lys Pro
        195                 200                 205

Asp Glu Lys Lys Asp Asp Asp Thr Ser Lys Pro Ala Phe Ser Phe Gly
        210                 215                 220

Ala Lys Pro Asp Glu Lys Lys Asp Asp Asp Thr Ser Lys Pro Ala Phe
225                 230                 235                 240

Ser Phe Gly Ala Lys Pro Asp Glu Lys Lys Asp Asp Asp Thr Ser Lys
            245                 250                 255

Pro Ala Phe Ser Phe Gly Ala Lys Pro Asp Glu Lys Lys Asp Asp Asp
            260                 265                 270

Thr Ser Lys Pro Ala Phe Ser Phe Gly Ala Lys Pro Asp Glu Lys Lys
            275                 280                 285
```

```
Asp Asp Asp Thr Ser Lys Pro Ala Phe Ser Phe Gly Ala Lys Pro Asp
    290                 295                 300

Glu Lys Lys Asp Asp Asp Thr Ser Lys Pro Ala Phe Ser Phe Gly Ala
305                 310                 315                 320

Lys Pro Asp Glu Lys Asp Asp Asp Thr Ser Lys Pro Ala Phe Ser
            325                 330                 335

Phe Gly Ala Lys Pro Asp Glu Lys Lys Asp Asp Asp Thr Ser Lys Thr
            340                 345                 350

Ser Ala Pro Gln Met Leu Arg Glu Leu Gln Glu Thr Asn Ala Ala Leu
        355                 360                 365

Gln Asp Val Arg Glu Leu Leu Arg Gln Gln Val Lys Glu Ile Thr Phe
    370                 375                 380

Leu Lys Asn Thr Val Met Glu Ser Asp Ala Ser
385                 390                 395

<210> SEQ ID NO 6
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Pro Ser Phe Ser Phe Gly Ala Lys Ser Asp Glu Asn Lys Ala Gly Ala
1               5                   10                  15

Thr Ser Lys Pro Ala Phe Ser Phe Gly Ala Lys Pro Glu Glu Lys Lys
            20                  25                  30

Asp Asp Asn Ser Ser Lys Pro Ala Phe Ser Phe Gly Ala Lys Ser Asn
        35                  40                  45

Glu Asp Lys Gln Asp Gly Thr Ala Lys Pro Ala Phe Ser Phe Gly Ala
50                  55                  60

Lys Pro Ala Glu Lys Asn Asn Asn Glu Thr Ser Lys Pro Ala Phe Ser
65                  70                  75                  80

Phe Gly Ala Lys Ser Asp Glu Lys Lys Asp Gly Asp Ala Ser Lys Pro
            85                  90                  95

Ala Phe Ser Phe Gly Ala Lys Pro Asp Glu Asn Lys Ala Ser Ala Thr
        100                 105                 110

Ser Lys Pro Ala Phe Ser Phe Gly Ala Lys Pro Glu Glu Lys Lys Asp
        115                 120                 125

Asp Asn Ser Ser Lys Pro Ala Phe Ser Phe Gly Ala Lys Ser Asn Glu
130                 135                 140

Asp Lys Gln Asp Gly Thr Ala Lys Pro Ala Phe Ser Phe Gly Ala Lys
145                 150                 155                 160

Pro Ala Glu Lys Asn Asn Asn Glu Thr Ser Lys Pro Ala Phe Ser Phe
                165                 170                 175

Gly Ala Lys Ser Asp Glu Lys Lys Asp Gly Asp Ala Ser Lys Pro Ala
            180                 185                 190

Phe Ser Phe Gly Ala Lys Ser Asp Glu Lys Lys Asp Ser Asp Ser Ser
        195                 200                 205

Lys Pro Ala Phe Ser Phe Gly Thr Lys Ser Asn Glu Lys Lys Asp Ser
        210                 215                 220

Gly Ser Ser Lys Pro Ala Phe Ser Phe Gly Ala Lys Pro Asp Glu Lys
225                 230                 235                 240

Lys Asn Asp Glu Val Ser Lys Pro Ala Phe Ser Phe Gly Ala Lys Ala
```

```
                    245                 250                 255
Asn Glu Lys Lys Glu Ser Asp Glu Ser Lys Ser Ala Phe Ser Phe Gly
                260                 265                 270

Ser Lys Pro Thr Gly Lys Glu Glu Gly Asp Gly Ala Lys Ala Ala Ile
            275                 280                 285

Ser Phe Gly Ala Lys Pro Glu Glu Gln Lys Ser Ser Asp Thr Ser Lys
        290                 295                 300

<210> SEQ ID NO 7
<211> LENGTH: 407
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Pro Gln Met Leu Arg Glu Leu Gln Glu Thr Asn Ala Ala Leu Gln
1               5                   10                  15

Asp Val Arg Glu Leu Leu Arg Gln Gln Val Lys Glu Ile Thr Phe Leu
            20                  25                  30

Lys Asn Thr Val Met Glu Ser Asp Ala Ser Gly Ala Ser Asp Asn Lys
        35                  40                  45

Thr Thr Asn Thr Thr Pro Ser Phe Ser Phe Gly Ala Lys Ser Asp Glu
50                  55                  60

Asn Lys Ala Gly Ala Thr Ser Lys Pro Ala Phe Ser Phe Gly Ala Lys
65                  70                  75                  80

Pro Glu Glu Lys Lys Asp Asp Asn Ser Ser Lys Pro Ala Phe Ser Phe
                85                  90                  95

Gly Ala Lys Ser Asn Glu Asp Lys Gln Asp Gly Thr Ala Lys Pro Ala
            100                 105                 110

Phe Ser Phe Gly Ala Lys Pro Ala Glu Lys Asn Asn Asn Glu Thr Ser
        115                 120                 125

Lys Pro Ala Phe Ser Phe Gly Ala Lys Ser Asp Glu Lys Lys Asp Gly
    130                 135                 140

Asp Ala Ser Lys Pro Ala Phe Ser Phe Gly Ala Lys Pro Asp Glu Asn
145                 150                 155                 160

Lys Ala Ser Ala Thr Ser Lys Pro Ala Phe Ser Phe Gly Ala Lys Pro
                165                 170                 175

Glu Glu Lys Lys Asp Asp Asn Ser Ser Lys Pro Ala Phe Ser Phe Gly
            180                 185                 190

Ala Lys Ser Asn Glu Asp Lys Gln Asp Gly Thr Ala Lys Pro Ala Phe
        195                 200                 205

Ser Phe Gly Ala Lys Pro Ala Glu Lys Asn Asn Asn Glu Thr Ser Lys
    210                 215                 220

Pro Ala Phe Ser Phe Gly Ala Lys Ser Asp Glu Lys Lys Asp Gly Asp
225                 230                 235                 240

Ala Ser Lys Pro Ala Phe Ser Phe Gly Ala Lys Ser Asp Glu Lys Lys
                245                 250                 255

Asp Ser Asp Ser Ser Lys Pro Ala Phe Ser Phe Gly Thr Lys Ser Asn
            260                 265                 270

Glu Lys Lys Asp Ser Gly Ser Ser Lys Pro Ala Phe Ser Phe Gly Ala
        275                 280                 285

Lys Pro Asp Glu Lys Lys Asn Asp Glu Val Ser Lys Pro Ala Phe Ser
    290                 295                 300
```

-continued

```
Phe Gly Ala Lys Ala Asn Glu Lys Lys Glu Ser Asp Glu Ser Lys Ser
305                 310                 315                 320

Ala Phe Ser Phe Gly Ser Lys Pro Thr Gly Lys Glu Glu Gly Asp Gly
                325                 330                 335

Ala Lys Ala Ala Ile Ser Phe Gly Ala Lys Pro Glu Glu Gln Lys Ser
                340                 345                 350

Ser Asp Thr Ser Lys Pro Ala Phe Thr Phe Gly Thr Ser Ala Pro Gln
                355                 360                 365

Met Leu Arg Glu Leu Gln Glu Thr Asn Ala Ala Leu Gln Asp Val Arg
        370                 375                 380

Glu Leu Leu Arg Gln Gln Val Lys Glu Ile Thr Phe Leu Lys Asn Thr
385                 390                 395                 400

Val Met Glu Ser Asp Ala Ser
                405

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Gly Ala Gly Ala Gly Pro Glu Gly
1               5

<210> SEQ ID NO 9
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Pro Ser Phe Ser Phe Gly Ala Lys Ser Asp Glu Asn Lys Ala Gly Ala
1               5                   10                  15

Thr Ser Lys Pro Ala Phe Ser Phe Gly Ala Lys Pro Glu Glu Lys Lys
                20                  25                  30

Asp Asp Asn Ser Ser Lys Pro Ala Phe Ser Phe Gly Ala Lys Ser Asn
            35                  40                  45

Glu Asp Lys Gln Asp Gly Thr Ala Lys Pro Ala Phe Ser Phe Gly Ala
    50                  55                  60

Lys Pro Ala Glu Lys Asn Asn Asn Glu Thr Ser Lys Pro Ala Phe Ser
65                  70                  75                  80

Phe Gly Ala Lys Ser Asp Glu Lys Lys Asp Gly Asp Ala Ser Lys Pro
                85                  90                  95

Ala Phe Ser Phe Gly Ala Lys Pro Asp Glu Asn Lys Ala Ser Ala Thr
                100                 105                 110

Ser Lys Pro Ala Phe Ser Phe Gly Ala Lys Pro Glu Glu Lys Lys Asp
            115                 120                 125

Asp Asn Ser Ser Lys Pro Ala Phe Ser Phe Gly Ala Lys Ser Asn Glu
        130                 135                 140

Asp Lys Gln Asp Gly Thr Ala Lys Pro Ala Phe Ser Phe Gly Ala Lys
145                 150                 155                 160

Pro Ala Glu Lys Asn Asn Asn Glu Thr Ser Lys Pro Ala Phe Ser Phe
                165                 170                 175
```

```
Gly Ala Lys Ser Asp Glu Lys Asp Gly Ala Ser Lys Pro Ala
            180                 185                 190

Phe Ser Phe Gly Ala Lys Ser Asp Glu Lys Lys Asp Ser Asp Ser Ser
        195                 200                 205

Lys Pro Ala Phe Ser Phe Gly Thr Lys Ser Asn Glu Lys Lys Asp Ser
210                 215                 220

Gly Ser Ser Lys Pro Ala Phe Ser Phe Gly Ala Lys Pro Asp Glu Lys
225                 230                 235                 240

Lys Asn Asp Glu Val Ser Lys Pro Ala Phe Ser Phe Gly Ala Lys Ala
                245                 250                 255

Asn Glu Lys Lys Glu Ser Asp Glu Ser Lys Ser Ala Phe Ser Phe Gly
            260                 265                 270

Ser Lys Pro Thr Gly Lys Glu Glu Gly Asp Gly Ala Lys Ala Ala Ile
        275                 280                 285

Ser Phe Gly Ala Lys Pro Glu Glu Gln Lys Ser Ser Asp Thr Ser Lys
    290                 295                 300
```

<210> SEQ ID NO 10
<211> LENGTH: 584
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Met Asp Ile Gly Ile Asn Ser Asp Pro Ser Thr Gly Ala Gly Ala Phe
1               5                   10                  15

Gly Thr Gly Gln Ser Thr Phe Gly Phe Asn Asn Ser Ala Pro Asn Asn
            20                  25                  30

Thr Asn Asn Ala Asn Ser Ser Ile Thr Pro Ala Phe Gly Ser Asn Asn
        35                  40                  45

Thr Gly Asn Thr Ala Phe Gly Asn Ser Asn Pro Thr Ser Asn Val Phe
    50                  55                  60

Gly Ser Asn Asn Ser Thr Thr Asn Thr Phe Gly Ser Asn Ser Ala Gly
65                  70                  75                  80

Thr Ser Leu Phe Gly Ser Ser Ala Gln Gln Thr Lys Ser Asn Gly
                85                  90                  95

Thr Ala Gly Gly Asn Thr Phe Gly Ser Ser Ser Leu Phe Asn Asn Ser
            100                 105                 110

Thr Asn Ser Asn Thr Thr Lys Pro Ala Phe Gly Gly Leu Asn Phe Gly
        115                 120                 125

Gly Gly Asn Asn Thr Thr Pro Ser Ser Thr Gly Asn Ala Asn Thr Ser
    130                 135                 140

Asn Asn Leu Phe Gly Ala Thr Ala Asn Ala Lys Pro Ala Phe Ser
145                 150                 155                 160

Phe Gly Ala Thr Thr Asn Asp Asp Lys Lys Thr Glu Pro Asp Lys Pro
                165                 170                 175

Ala Phe Ser Phe Asn Ser Ser Val Gly Asn Lys Thr Asp Ala Gln Ala
            180                 185                 190

Pro Thr Thr Gly Phe Ser Phe Gly Ser Gln Leu Gly Gly Asn Lys Thr
        195                 200                 205

Val Asn Glu Ala Ala Lys Pro Ser Leu Ser Phe Gly Ser Gly Ser Ala
    210                 215                 220

Gly Ala Asn Pro Ala Gly Ala Ser Gln Pro Glu Pro Thr Thr Asn Glu
225                 230                 235                 240
```

Pro Ala Lys Pro Ala Leu Ser Phe Gly Thr Ala Ser Asp Asn Lys
                245                 250                 255

Thr Thr Asn Thr Thr Pro Ser Phe Ser Phe Gly Ala Lys Ser Asp Glu
            260                 265                 270

Asn Lys Ala Gly Ala Thr Ser Lys Pro Ala Phe Ser Phe Gly Ala Lys
                275                 280                 285

Pro Glu Glu Lys Lys Asp Asp Asn Ser Ser Lys Pro Ala Phe Ser Phe
            290                 295                 300

Gly Ala Lys Ser Asn Glu Asp Lys Gln Asp Gly Thr Ala Lys Pro Ala
305                 310                 315                 320

Phe Ser Phe Gly Ala Lys Pro Ala Glu Lys Asn Asn Asn Glu Thr Ser
                325                 330                 335

Lys Pro Ala Phe Ser Phe Gly Ala Lys Ser Asp Glu Lys Lys Asp Gly
                340                 345                 350

Asp Ala Ser Lys Pro Ala Phe Ser Phe Gly Ala Lys Pro Asp Glu Asn
                355                 360                 365

Lys Ala Ser Ala Thr Ser Lys Pro Ala Phe Ser Phe Gly Ala Lys Pro
            370                 375                 380

Glu Glu Lys Lys Asp Asp Asn Ser Ser Lys Pro Ala Phe Ser Phe Gly
385                 390                 395                 400

Ala Lys Ser Asn Glu Asp Lys Gln Asp Gly Thr Ala Lys Pro Ala Phe
                405                 410                 415

Ser Phe Gly Ala Lys Pro Ala Glu Lys Asn Asn Asn Glu Thr Ser Lys
                420                 425                 430

Pro Ala Phe Ser Phe Gly Ala Lys Ser Asp Glu Lys Lys Asp Gly Asp
            435                 440                 445

Ala Ser Lys Pro Ala Phe Ser Phe Gly Ala Lys Ser Asp Glu Lys Lys
            450                 455                 460

Asp Ser Asp Ser Ser Lys Pro Ala Phe Ser Phe Gly Thr Lys Ser Asn
465                 470                 475                 480

Glu Lys Lys Asp Ser Gly Ser Ser Lys Pro Ala Phe Ser Phe Gly Ala
                485                 490                 495

Lys Pro Asp Glu Lys Lys Asn Asp Glu Val Ser Lys Pro Ala Phe Ser
            500                 505                 510

Phe Gly Ala Lys Ala Asn Glu Lys Lys Glu Ser Asp Glu Ser Lys Ser
                515                 520                 525

Ala Phe Ser Phe Gly Ser Lys Pro Thr Gly Lys Glu Glu Gly Asp Gly
                530                 535                 540

Ala Lys Ala Ala Ile Ser Phe Gly Ala Lys Pro Glu Glu Gln Lys Ser
545                 550                 555                 560

Ser Asp Thr Ser Lys Pro Ala Phe Thr Phe Gly Lys Leu Ala Ala Ala
                565                 570                 575

Leu Glu His His His His His His
            580

<210> SEQ ID NO 11
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Asp Ile Gly Ile Asn Ser Asp Pro Gly Ser Gly Ser Gly Ala Ser

```
            1               5                   10                  15
        Asp Asn Lys Thr Thr Asn Thr Thr Pro Ser Phe Ser Phe Gly Ala Lys
                        20                  25                  30

Ser Asp Glu Asn Lys Ala Gly Ala Thr Ser Lys Pro Ala Phe Ser Phe
                        35                  40                  45

Gly Ala Lys Pro Glu Glu Lys Lys Asp Asp Asn Ser Ser Lys Pro Ala
                    50                  55                  60

Phe Ser Phe Gly Ala Lys Ser Asn Glu Asp Lys Gln Asp Gly Thr Ala
        65                  70                  75                  80

Lys Pro Ala Phe Ser Phe Gly Ala Lys Pro Ala Glu Lys Asn Asn Asn
                        85                  90                  95

Glu Thr Ser Lys Pro Ala Phe Ser Phe Gly Ala Lys Ser Asp Glu Lys
                        100                 105                 110

Lys Asp Gly Asp Ala Ser Lys Pro Ala Phe Ser Phe Gly Ala Lys Pro
                        115                 120                 125

Asp Glu Asn Lys Ala Ser Ala Thr Ser Lys Pro Ala Phe Ser Phe Gly
                        130                 135                 140

Ala Lys Pro Glu Glu Lys Lys Asp Asp Asn Ser Ser Lys Pro Ala Phe
        145                 150                 155                 160

Ser Phe Gly Ala Lys Ser Asn Glu Asp Lys Gln Asp Gly Thr Ala Lys
                        165                 170                 175

Pro Ala Phe Ser Phe Gly Ala Lys Pro Ala Glu Lys Asn Asn Asn Glu
                        180                 185                 190

Thr Ser Lys Pro Ala Phe Ser Phe Gly Ala Lys Ser Asp Glu Lys Lys
                        195                 200                 205

Asp Gly Asp Ala Ser Lys Pro Ala Phe Ser Phe Gly Ala Lys Ser Asp
                    210                 215                 220

Glu Lys Lys Asp Ser Asp Ser Ser Lys Pro Ala Phe Ser Phe Gly Thr
        225                 230                 235                 240

Lys Ser Asn Glu Lys Lys Asp Ser Gly Ser Ser Lys Pro Ala Phe Ser
                        245                 250                 255

Phe Gly Ala Lys Pro Asp Glu Lys Lys Asn Asp Glu Val Ser Lys Pro
                        260                 265                 270

Ala Phe Ser Phe Gly Ala Lys Ala Asn Glu Lys Lys Glu Ser Asp Glu
                        275                 280                 285

Ser Lys Ser Ala Phe Ser Phe Gly Ser Lys Pro Thr Gly Lys Glu Glu
                        290                 295                 300

Gly Asp Gly Ala Lys Ala Ala Ile Ser Phe Gly Ala Lys Pro Glu Glu
        305                 310                 315                 320

Gln Lys Ser Ser Asp Thr Ser Lys Pro Ala Phe Thr Phe Gly Thr Ser
                        325                 330                 335

Gly Ser Gly Lys Leu Ala Ala Ala Leu Glu His His His His His His
                        340                 345                 350

<210> SEQ ID NO 12
<211> LENGTH: 546
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Asp Ile Gly Ile Asn Ser Asp Pro Ala Pro Gln Met Leu Arg Glu
1               5                   10                  15
```

```
Leu Gln Glu Thr Asn Ala Ala Leu Gln Asp Val Arg Glu Leu Leu Arg
             20                  25                  30
Gln Gln Val Lys Glu Ile Thr Phe Leu Lys Asn Thr Val Met Glu Ser
         35                  40                  45
Asp Ala Ser Gly Ala Ser Ala Ile Ser Gly Asp Ser Leu Ile Ser Leu
50                  55                  60
Ala Ser Thr Gly Lys Arg Val Ser Ile Lys Asp Leu Leu Asp Glu Lys
65                  70                  75                  80
Asp Phe Glu Ile Trp Ala Ile Asn Glu Gln Thr Met Lys Leu Glu Ser
                 85                  90                  95
Ala Lys Val Ser Arg Val Phe Cys Thr Gly Lys Lys Leu Val Tyr Ile
             100                 105                 110
Leu Lys Thr Arg Leu Gly Arg Thr Ile Lys Ala Thr Ala Asn His Arg
         115                 120                 125
Phe Leu Thr Ile Asp Gly Trp Lys Arg Leu Asp Glu Leu Ser Leu Lys
130                 135                 140
Glu His Ile Ala Leu Pro Arg Lys Leu Glu Ser Ser Leu Gln Leu
145                 150                 155                 160
Ser Pro Glu Ile Glu Lys Leu Ser Gln Ser Asp Ile Tyr Trp Asp Ser
                 165                 170                 175
Ile Val Ser Ile Thr Glu Thr Gly Val Glu Glu Val Phe Asp Leu Thr
             180                 185                 190
Val Pro Gly Pro His Asn Phe Val Ala Asn Asp Ile Ile Val His Asn
         195                 200                 205
Ala Ser Asp Asn Lys Thr Thr Asn Thr Thr Pro Ser Phe Ser Phe Gly
210                 215                 220
Ala Lys Ser Asp Glu Asn Lys Ala Gly Ala Thr Ser Lys Pro Ala Phe
225                 230                 235                 240
Ser Phe Gly Ala Lys Pro Glu Glu Lys Lys Asp Asp Asn Ser Ser Lys
                 245                 250                 255
Pro Ala Phe Ser Phe Gly Ala Lys Ser Asn Glu Asp Lys Gln Asp Gly
             260                 265                 270
Thr Ala Lys Pro Ala Phe Ser Phe Gly Ala Lys Pro Ala Glu Lys Asn
         275                 280                 285
Asn Asn Glu Thr Ser Lys Pro Ala Phe Ser Phe Gly Ala Lys Ser Asp
290                 295                 300
Glu Lys Lys Asp Gly Asp Ala Ser Lys Pro Ala Phe Ser Phe Gly Ala
305                 310                 315                 320
Lys Pro Asp Glu Asn Lys Ala Ser Ala Thr Ser Lys Pro Ala Phe Ser
                 325                 330                 335
Phe Gly Ala Lys Pro Glu Glu Lys Lys Asp Asp Asn Ser Ser Lys Pro
             340                 345                 350
Ala Phe Ser Phe Gly Ala Lys Ser Asn Glu Asp Lys Gln Asp Gly Thr
         355                 360                 365
Ala Lys Pro Ala Phe Ser Phe Gly Ala Lys Pro Ala Glu Lys Asn Asn
370                 375                 380
Asn Glu Thr Ser Lys Pro Ala Phe Ser Phe Gly Ala Lys Ser Asp Glu
385                 390                 395                 400
Lys Lys Asp Gly Asp Ala Ser Lys Pro Ala Phe Ser Phe Gly Ala Lys
                 405                 410                 415
Ser Asp Glu Lys Lys Asp Ser Asp Ser Ser Lys Pro Ala Phe Ser Phe
             420                 425                 430
Gly Thr Lys Ser Asn Glu Lys Lys Asp Ser Gly Ser Ser Lys Pro Ala
```

```
                435                 440                 445
Phe Ser Phe Gly Ala Lys Pro Asp Glu Lys Asn Asp Glu Val Ser
450                 455                 460
Lys Pro Ala Phe Ser Phe Gly Ala Lys Ala Asn Glu Lys Lys Glu Ser
465                 470                 475                 480
Asp Glu Ser Lys Ser Ala Phe Ser Phe Gly Ser Lys Pro Thr Gly Lys
                485                 490                 495
Glu Glu Gly Asp Gly Ala Lys Ala Ala Ile Ser Phe Gly Ala Lys Pro
                500                 505                 510
Glu Glu Gln Lys Ser Ser Asp Thr Ser Lys Pro Ala Phe Thr Phe Gly
                515                 520                 525
Thr Ser Gly Ser Gly Lys Leu Ala Ala Ala Leu Glu His His His His
530                 535                 540
His His
545

<210> SEQ ID NO 13
<211> LENGTH: 338
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Asp Ile Gly Ile Asn Ser Asp Pro Gly Ser Gly Ala Ser Pro Ala
1               5                   10                  15
Phe Ser Phe Gly Ala Lys Pro Asp Glu Lys Lys Asp Asp Asp Thr Ser
                20                  25                  30
Lys Pro Ala Phe Ser Phe Gly Ala Lys Pro Asp Glu Lys Lys Asp Asp
            35                  40                  45
Asp Thr Ser Lys Pro Ala Phe Ser Phe Gly Ala Lys Pro Asp Glu Lys
50                  55                  60
Lys Asp Asp Asp Thr Ser Lys Pro Ala Phe Ser Phe Gly Ala Lys Pro
65                  70                  75                  80
Asp Glu Lys Lys Asp Asp Asp Thr Ser Lys Pro Ala Phe Ser Phe Gly
                85                  90                  95
Ala Lys Pro Asp Glu Lys Lys Asp Asp Asp Thr Ser Lys Pro Ala Phe
            100                 105                 110
Ser Phe Gly Ala Lys Pro Asp Glu Lys Lys Asp Asp Asp Thr Ser Lys
        115                 120                 125
Pro Ala Phe Ser Phe Gly Ala Lys Pro Asp Glu Lys Lys Asp Asp Asp
        130                 135                 140
Thr Ser Lys Pro Ala Phe Ser Phe Gly Ala Lys Pro Asp Glu Lys Lys
145                 150                 155                 160
Asp Asp Asp Thr Ser Lys Thr Ser Pro Ala Phe Ser Phe Gly Ala Lys
                165                 170                 175
Pro Asp Glu Lys Lys Asp Asp Asp Thr Ser Lys Pro Ala Phe Ser Phe
            180                 185                 190
Gly Ala Lys Pro Asp Glu Lys Lys Asp Asp Asp Thr Ser Lys Pro Ala
        195                 200                 205
Phe Ser Phe Gly Ala Lys Pro Asp Glu Lys Lys Asp Asp Asp Thr Ser
    210                 215                 220
Lys Pro Ala Phe Ser Phe Gly Ala Lys Pro Asp Glu Lys Lys Asp Asp
225                 230                 235                 240
```

Asp Thr Ser Lys Pro Ala Phe Ser Phe Gly Ala Lys Pro Asp Glu Lys
            245                 250                 255

Lys Asp Asp Asp Thr Ser Lys Pro Ala Phe Ser Phe Gly Ala Lys Pro
        260                 265                 270

Asp Glu Lys Lys Asp Asp Asp Thr Ser Lys Pro Ala Phe Ser Phe Gly
    275                 280                 285

Ala Lys Pro Asp Glu Lys Lys Asp Asp Asp Thr Ser Lys Pro Ala Phe
290                 295                 300

Ser Phe Gly Ala Lys Pro Asp Glu Lys Lys Asp Asp Thr Ser Lys
305                 310                 315                 320

Thr Ser Gly Ser Gly Lys Leu Ala Ala Ala Leu Glu His His His His
                325                 330                 335

His His

<210> SEQ ID NO 14
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Asp Ile Gly Ile Asn Ser Asp Pro Gly Ser Gly Ala Ser Pro Ala
1               5                   10                  15

Phe Ser Phe Gly Ala Lys Pro Asp Glu Lys Lys Asp Ser Asp Thr Ser
                20                  25                  30

Lys Pro Ala Phe Ser Phe Gly Ala Lys Pro Asp Glu Lys Lys Asp Ser
            35                  40                  45

Asp Thr Ser Lys Pro Ala Phe Ser Phe Gly Ala Lys Pro Asp Glu Lys
        50                  55                  60

Lys Asp Ser Asp Thr Ser Lys Pro Ala Phe Ser Phe Gly Ala Lys Pro
65                  70                  75                  80

Asp Glu Lys Lys Asp Ser Asp Thr Ser Lys Pro Ala Phe Ser Phe Gly
                85                  90                  95

Ala Lys Pro Asp Glu Lys Lys Asp Ser Asp Thr Ser Lys Pro Ala Phe
            100                 105                 110

Ser Phe Gly Ala Lys Pro Asp Glu Lys Lys Asp Ser Asp Thr Ser Lys
        115                 120                 125

Pro Ala Phe Ser Phe Gly Ala Lys Pro Asp Glu Lys Lys Asp Ser Asp
    130                 135                 140

Thr Ser Lys Pro Ala Phe Ser Phe Gly Ala Lys Pro Asp Glu Lys Lys
145                 150                 155                 160

Asp Ser Asp Thr Ser Lys Thr Ser Pro Ala Phe Ser Phe Gly Ala Lys
                165                 170                 175

Pro Asp Glu Lys Lys Asp Ser Asp Thr Ser Lys Pro Ala Phe Ser Phe
            180                 185                 190

Gly Ala Lys Pro Asp Glu Lys Lys Asp Ser Asp Thr Ser Lys Pro Ala
        195                 200                 205

Phe Ser Phe Gly Ala Lys Pro Asp Glu Lys Lys Asp Ser Asp Thr Ser
    210                 215                 220

Lys Pro Ala Phe Ser Phe Gly Ala Lys Pro Asp Glu Lys Lys Asp Ser
225                 230                 235                 240

Asp Thr Ser Lys Pro Ala Phe Ser Phe Gly Ala Lys Pro Asp Glu Lys
                245                 250                 255

```
Lys Asp Ser Asp Thr Ser Lys Pro Ala Phe Ser Phe Gly Ala Lys Pro
            260                 265                 270

Asp Glu Lys Lys Asp Ser Asp Thr Ser Lys Pro Ala Phe Ser Phe Gly
        275                 280                 285

Ala Lys Pro Asp Glu Lys Lys Asp Ser Asp Thr Ser Lys Pro Ala Phe
    290                 295                 300

Ser Phe Gly Ala Lys Pro Asp Glu Lys Lys Asp Ser Asp Thr Ser Lys
305                 310                 315                 320

Thr Ser Lys Thr Ser Gly Ser Gly Lys Leu Ala Ala Ala Leu Glu His
                325                 330                 335

His His His His His
            340

<210> SEQ ID NO 15
<211> LENGTH: 430
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Asp Ile Gly Ile Asn Ser Asp Pro Ala Pro Gln Met Leu Arg Glu
1               5                   10                  15

Leu Gln Glu Thr Asn Ala Ala Leu Gln Asp Val Arg Glu Leu Leu Arg
            20                  25                  30

Gln Gln Val Lys Glu Ile Thr Phe Leu Lys Asn Thr Val Met Glu Ser
        35                  40                  45

Asp Ala Ser Gly Ala Ser Asp Asn Lys Thr Thr Asn Thr Thr Pro Ser
    50                  55                  60

Phe Ser Phe Gly Ala Lys Ser Asp Glu Asn Lys Ala Gly Ala Thr Ser
65                  70                  75                  80

Lys Pro Ala Phe Ser Phe Gly Ala Lys Pro Glu Glu Lys Lys Asp Asp
            85                  90                  95

Asn Ser Ser Lys Pro Ala Phe Ser Phe Gly Ala Lys Ser Asn Glu Asp
        100                 105                 110

Lys Gln Asp Gly Thr Ala Lys Pro Ala Phe Ser Phe Gly Ala Lys Pro
    115                 120                 125

Ala Glu Lys Asn Asn Asn Glu Thr Ser Lys Pro Ala Phe Ser Phe Gly
    130                 135                 140

Ala Lys Ser Asp Glu Lys Lys Asp Gly Asp Ala Ser Lys Pro Ala Phe
145                 150                 155                 160

Ser Phe Gly Ala Lys Pro Asp Glu Asn Lys Ala Ser Ala Thr Ser Lys
            165                 170                 175

Pro Ala Phe Ser Phe Gly Ala Lys Pro Glu Lys Lys Asp Asp Asn
        180                 185                 190

Ser Ser Lys Pro Ala Phe Ser Phe Gly Ala Lys Ser Asn Glu Asp Lys
        195                 200                 205

Gln Asp Gly Thr Ala Lys Pro Ala Phe Ser Phe Gly Ala Lys Pro Ala
    210                 215                 220

Glu Lys Asn Asn Asn Glu Thr Ser Lys Pro Ala Phe Ser Phe Gly Ala
225                 230                 235                 240

Lys Ser Asp Glu Lys Lys Asp Gly Asp Ala Ser Lys Pro Ala Phe Ser
            245                 250                 255

Phe Gly Ala Lys Ser Asp Glu Lys Lys Asp Ser Asp Ser Ser Lys Pro
        260                 265                 270
```

```
Ala Phe Ser Phe Gly Thr Lys Ser Asn Glu Lys Lys Asp Ser Gly Ser
            275                 280                 285

Ser Lys Pro Ala Phe Ser Phe Gly Ala Lys Pro Asp Glu Lys Lys Asn
        290                 295                 300

Asp Glu Val Ser Lys Pro Ala Phe Ser Phe Gly Ala Lys Ala Asn Glu
305                 310                 315                 320

Lys Lys Glu Ser Asp Glu Ser Lys Ser Ala Phe Ser Phe Gly Ser Lys
                325                 330                 335

Pro Thr Gly Lys Glu Glu Gly Asp Gly Ala Lys Ala Ala Ile Ser Phe
            340                 345                 350

Gly Ala Lys Pro Glu Glu Gln Lys Ser Ser Asp Thr Ser Lys Pro Ala
        355                 360                 365

Phe Thr Phe Gly Thr Ser Ala Pro Gln Met Leu Arg Glu Leu Gln Glu
    370                 375                 380

Thr Asn Ala Ala Leu Gln Asp Val Arg Glu Leu Leu Arg Gln Gln Val
385                 390                 395                 400

Lys Glu Ile Thr Phe Leu Lys Asn Thr Val Met Glu Ser Asp Ala Ser
                405                 410                 415

Gly Lys Leu Ala Ala Ala Leu Glu His His His His His His
            420                 425                 430

<210> SEQ ID NO 16
<211> LENGTH: 419
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Asp Ile Gly Ile Asn Ser Asp Pro Ala Pro Gln Met Leu Arg Glu
1               5                   10                  15

Leu Gln Glu Thr Asn Ala Ala Leu Gln Asp Val Arg Glu Leu Leu Arg
            20                  25                  30

Gln Gln Val Lys Glu Ile Thr Phe Leu Lys Asn Thr Val Met Glu Ser
        35                  40                  45

Asp Ala Ser Gly Ala Ser Pro Ala Phe Ser Phe Gly Ala Lys Pro Asp
    50                  55                  60

Glu Lys Lys Asp Asp Asp Thr Ser Lys Pro Ala Phe Ser Phe Gly Ala
65                  70                  75                  80

Lys Pro Asp Glu Lys Lys Asp Asp Asp Thr Ser Lys Pro Ala Phe Ser
                85                  90                  95

Phe Gly Ala Lys Pro Asp Glu Lys Lys Asp Asp Asp Thr Ser Lys Pro
            100                 105                 110

Ala Phe Ser Phe Gly Ala Lys Pro Asp Glu Lys Lys Asp Asp Asp Thr
        115                 120                 125

Ser Lys Pro Ala Phe Ser Phe Gly Ala Lys Pro Asp Glu Lys Lys Asp
    130                 135                 140

Asp Asp Thr Ser Lys Pro Ala Phe Ser Phe Gly Ala Lys Pro Asp Glu
145                 150                 155                 160

Lys Lys Asp Asp Asp Thr Ser Lys Pro Ala Phe Ser Phe Gly Ala Lys
                165                 170                 175

Pro Asp Glu Lys Lys Asp Asp Asp Thr Ser Lys Pro Ala Phe Ser Phe
            180                 185                 190

Gly Ala Lys Pro Asp Glu Lys Lys Asp Asp Asp Thr Ser Lys Thr Ser
```

```
                195                 200                 205
Pro Ala Phe Ser Phe Gly Ala Lys Pro Asp Glu Lys Lys Asp Asp
210                 215                 220

Thr Ser Lys Pro Ala Phe Ser Phe Gly Ala Lys Pro Asp Glu Lys Lys
225                 230                 235                 240

Asp Asp Asp Thr Ser Lys Pro Ala Phe Ser Phe Gly Ala Lys Pro Asp
                245                 250                 255

Glu Lys Lys Asp Asp Asp Thr Ser Lys Pro Ala Phe Ser Phe Gly Ala
            260                 265                 270

Lys Pro Asp Glu Lys Lys Asp Asp Asp Thr Ser Lys Pro Ala Phe Ser
        275                 280                 285

Phe Gly Ala Lys Pro Asp Glu Lys Lys Asp Asp Asp Thr Ser Lys Pro
    290                 295                 300

Ala Phe Ser Phe Gly Ala Lys Pro Asp Glu Lys Lys Asp Asp Asp Thr
305                 310                 315                 320

Ser Lys Pro Ala Phe Ser Phe Gly Ala Lys Pro Asp Glu Lys Lys Asp
                325                 330                 335

Asp Asp Thr Ser Lys Pro Ala Phe Ser Phe Gly Ala Lys Pro Asp Glu
            340                 345                 350

Lys Lys Asp Asp Asp Thr Ser Lys Thr Ser Ala Pro Gln Met Leu Arg
        355                 360                 365

Glu Leu Gln Glu Thr Asn Ala Ala Leu Gln Asp Val Arg Glu Leu Leu
    370                 375                 380

Arg Gln Gln Val Lys Glu Ile Thr Phe Leu Lys Asn Thr Val Met Glu
385                 390                 395                 400

Ser Asp Ala Ser Gly Gly Lys Leu Ala Ala Ala Leu Glu His His His
                405                 410                 415

His His His

<210> SEQ ID NO 17
<211> LENGTH: 419
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Asp Ile Gly Ile Asn Ser Asp Pro Ala Pro Gln Met Leu Arg Glu
1               5                   10                  15

Leu Gln Glu Thr Asn Ala Ala Leu Gln Asp Val Arg Glu Leu Leu Arg
                20                  25                  30

Gln Gln Val Lys Glu Ile Thr Phe Leu Lys Asn Thr Val Met Glu Ser
            35                  40                  45

Asp Ala Ser Gly Ala Ser Pro Ala Phe Ser Phe Gly Ala Lys Pro Asp
        50                  55                  60

Glu Lys Lys Asp Ser Asp Thr Ser Lys Pro Ala Phe Ser Phe Gly Ala
65                  70                  75                  80

Lys Pro Asp Glu Lys Lys Asp Ser Asp Thr Ser Lys Pro Ala Phe Ser
                85                  90                  95

Phe Gly Ala Lys Pro Asp Glu Lys Lys Asp Ser Asp Thr Ser Lys Pro
            100                 105                 110

Ala Phe Ser Phe Gly Ala Lys Pro Asp Glu Lys Lys Asp Ser Asp Thr
        115                 120                 125

Ser Lys Pro Ala Phe Ser Phe Gly Ala Lys Pro Asp Glu Lys Lys Asp
```

Ser Asp Thr Ser Lys Pro Ala Phe Ser Phe Gly Ala Lys Pro Asp Glu
145                 150                 155                 160

Lys Lys Asp Ser Asp Thr Ser Lys Pro Ala Phe Ser Phe Gly Ala Lys
                165                 170                 175

Pro Asp Glu Lys Lys Asp Ser Asp Thr Ser Lys Pro Ala Phe Ser Phe
            180                 185                 190

Gly Ala Lys Pro Asp Glu Lys Lys Asp Ser Asp Thr Ser Lys Thr Ser
        195                 200                 205

Pro Ala Phe Ser Phe Gly Ala Lys Pro Asp Glu Lys Lys Asp Ser Asp
210                 215                 220

Thr Ser Lys Pro Ala Phe Ser Phe Gly Ala Lys Pro Asp Glu Lys Lys
225                 230                 235                 240

Asp Ser Asp Thr Ser Lys Pro Ala Phe Ser Phe Gly Ala Lys Pro Asp
                245                 250                 255

Glu Lys Lys Asp Ser Asp Thr Ser Lys Pro Ala Phe Ser Phe Gly Ala
            260                 265                 270

Lys Pro Asp Glu Lys Lys Asp Ser Asp Thr Ser Lys Pro Ala Phe Ser
        275                 280                 285

Phe Gly Ala Lys Pro Asp Glu Lys Lys Asp Ser Asp Thr Ser Lys Pro
290                 295                 300

Ala Phe Ser Phe Gly Ala Lys Pro Asp Glu Lys Lys Asp Ser Asp Thr
305                 310                 315                 320

Ser Lys Pro Ala Phe Ser Phe Gly Ala Lys Pro Asp Glu Lys Lys Asp
                325                 330                 335

Ser Asp Thr Ser Lys Pro Ala Phe Ser Phe Gly Ala Lys Pro Asp Glu
            340                 345                 350

Lys Lys Asp Ser Asp Thr Ser Lys Thr Ser Ala Pro Gln Met Leu Arg
        355                 360                 365

Glu Leu Gln Glu Thr Asn Ala Ala Leu Gln Asp Val Arg Glu Leu Leu
370                 375                 380

Arg Gln Gln Val Lys Glu Ile Thr Phe Leu Lys Asn Thr Val Met Glu
385                 390                 395                 400

Ser Asp Ala Ser Gly Gly Lys Leu Ala Ala Ala Leu Glu His His His
                405                 410                 415

His His His

<210> SEQ ID NO 18
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gcgccgcaga tgctgcgcga actgcaggaa accaacgcgg cgctgcagga tgtgcgcgaa      60
ctgctgcgcc agcaggtgaa agaaattacc tttctgaaaa acaccgtgat ggaaagcgat     120
gcgagcggcg cgagcccggc gtttagcttt ggcgcgaaac cggatgaaaa aaaagatagc     180
gataccagca aaccggcgtt tagctttggc gcgaaaccgg atgaaaaaaa agatagcgat     240
accagcaaac cggcgtttag ctttggcgcg aaaccggatg aaaaaaaaga tagcgatacc     300
agcaaaccgg cgtttagctt tggcgcgaaa ccggatgaaa aaaagatag cgataccagc     360 aaaccggcgt ttagctttgg cgcgaaaccg gatgaaaaaa aagatagcga taccagcaaa     420

```
ccggcgttta gctttggcgc gaaaccggat gaaaaaaaag atagcgatac cagcaaaccg      480
gcgtttagct ttggcgcgaa accggatgaa aaaaagata gcgataccag caaaccggcg      540
tttagctttg gcgcgaaacc ggatgaaaaa aagatagcg ataccagcaa aaccagcccg      600
gcgtttagct ttggcgcgaa accggatgaa aaaaagata gcgataccag caaaccggcg      660
tttagctttg gcgcgaaacc ggatgaaaaa aagatagcg ataccagcaa accggcgttt      720
agctttggcg cgaaaccgga tgaaaaaaaa gatagcgata ccagcaaacc ggcgtttagc      780
tttggcgcga aaccggatga aaaaaagat agcgatacca gcaaaccggc gtttagcttt      840
ggcgcgaaac cggatgaaaa aaagatagc gataccagca aaccggcgtt tagctttggc      900
gcgaaaccgg atgaaaaaaa agatagcgat accagcaaac cggcgtttag ctttggcgcg      960
aaaccggatg aaaaaaaaga tagcgatacc agcaaaccgg cgtttagctt tggcgcgaaa     1020
ccggatgaaa aaaagatag cgataccagc aaaaccagcg cgccgcagat gctgcgcgaa     1080
ctgcaggaaa ccaacgcggc gctgcaggat gtgcgcgaac tgctgcgcca gcaggtgaaa     1140
gaaattacct ttctgaaaaa caccgtgatg gaaagcgatg cgagc                     1185
```

<210> SEQ ID NO 19
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
gcgccgcaga tgctgcgcga actgcaggaa ccaacgcggc gctgcagga tgtgcgcgaa       60 ctgctgcgcc agcaggtgaa agaaattacc tttctgaaaa acaccgtgat ggaaagcgat      120
gcgagcggcg cgagcccggc gtttagcttt ggcgcgaaac cggatgaaaa aaagatgat      180 gataccagca aaccggcgtt tagctttggc gcgaaaccgg atgaaaaaaa agatgatgat      240
accagcaaac cggcgtttag ctttggcgcg aaaccggatg aaaaaaaaga tgatgatacc      300
agcaaaccgg cgtttagctt tggcgcgaaa ccggatgaaa aaaaagatga tgataccagc      360
aaaccggcgt ttagctttgg cgcgaaaccg gatgaaaaaa agatgatga taccagcaaa      420 ccggcgttta gctttggcgc gaaaccggat gaaaaaaaag atgatgatac cagcaaaccg      480
gcgtttagct ttggcgcgaa accggatgaa aaaaagatg atgataccag caaaccggcg      540
tttagctttg gcgcgaaacc ggatgaaaaa aagatgatg ataccagcaa aaccagcccg      600
gcgtttagct ttggcgcgaa accggatgaa aaaaagatg atgataccag caaaccggcg      660
tttagctttg gcgcgaaacc ggatgaaaaa aagatgatg ataccagcaa accggcgttt      720
agctttggcg cgaaaccgga tgaaaaaaaa gatgatgata ccagcaaacc ggcgtttagc      780
tttggcgcga aaccggatga aaaaaagat gatgatacca gcaaaccggc gtttagcttt      840
ggcgcgaaac cggatgaaaa aaagatgat gataccagca aaccggcgtt tagctttggc      900
gcgaaaccgg atgaaaaaaa agatgatgat accagcaaac cggcgtttag ctttggcgcg      960
aaaccggatg aaaaaaaaga tgatgatacc agcaaaccgg cgtttagctt tggcgcgaaa     1020
ccggatgaaa aaaagatga tgataccagc aaaaccagcg cgccgcagat gctgcgcgaa     1080
ctgcaggaaa ccaacgcggc gctgcaggat gtgcgcgaac tgctgcgcca gcaggtgaaa     1140
gaaattacct ttctgaaaaa caccgtgatg gaaagcgatg cgagc                     1185
```

```
<210> SEQ ID NO 20
<211> LENGTH: 912
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
ccgagcttta gctttggcgc gaaaagcgat gaaaacaaag cgggcgcgac cagcaaaccg      60
gcgtttagct ttggcgcgaa accggaagaa aaaaagatg ataacagcag caaaccggcg     120
tttagctttg gcgcgaaaag caacgaagat aaacaggatg gcaccgcgaa accggcgttt     180
agctttggcg cgaaaccggc ggaaaaaaac aacgaaa ccagcaaacc ggcgtttagc       240
tttggcgcga aaagcgatga aaaaaagat ggcgatgcga gcaaaccggc gtttagcttt       300
ggcgcgaaac cggatgaaaa caaagcgagc gcgaccagca aaccggcgtt tagctttggc     360
gcgaaaccgg aagaaaaaaa agatgataac agcagcaaac cggcgtttag ctttggcgcg     420
aaaagcaacg aagataaaca ggatggcacc gcgaaaccgg cgtttagctt tggcgcgaaa     480
ccggcggaaa aaacaacaa cgaaaccagc aaaccggcgt ttagctttgg cgcgaaaagc       540
gatgaaaaaa aagatggcga tgcgagcaaa ccggcgttta gctttggcgc gaaaagcgat     600
gaaaaaaaag atagcgatag cagcaaaccg gcgtttagct ttggcaccaa agcaacgaa      660 aaaaagata gcggcagcag caaaccggcg tttagctttg gcgcgaaacc ggatgaaaaa      720 aaaacgatg aagtgagcaa accggcgttt agctttggcg cgaaagcgaa cgaaaaaaaa       780
gaaagcgatg aaagcaaaag cgcgtttagc tttggcagca accgaccgg caagaagaa        840 ggcgatggcg cgaaagcggc gattagcttt ggcgcgaaac cggaagaaca gaaaagcagc     900
gataccagca aa                                                         912

<210> SEQ ID NO 21
<211> LENGTH: 1221
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
gcgccgcaga tgctgcgcga actgcaggaa accaacgcgg cgctgcagga tgtgcgcgaa      60
ctgctgcgcc agcaggtgaa agaaattacc tttctgaaaa acaccgtgat ggaaagcgat     120
gcgagcggcg cgagcgataa caaaaccacc aacaccaccc cgagctttag ctttggcgcg     180 aaagcgatg aaaacaaagc gggcgcgacc agcaaaccgg cgtttagctt tggcgcgaaa     240
ccggaagaaa aaaagatga taacagcagc aaaccggcgt ttagctttgg cgcgaaaagc     300
aacgaagata acaggatgg caccgcgaaa ccggcgttta gctttggcgc gaaaccggcg     360
gaaaaaaaca acaacgaaac cagcaaaccg gcgtttagct ttggcgcgaa aagcgatgaa     420 aaaaagatg gcgatgcgag caaaccggcg tttagctttg gcgcgaaacc ggatgaaaac     480
aaagcgagcg cgaccagcaa accggcgttt agctttggcg cgaaaccgga agaaaaaaaa      540
gatgataaca gcagcaaacc ggcgtttagc tttggcgcga aaagcaacga agataaacag     600
gatggcaccg cgaaaccggc gtttagcttt ggcgcgaaac cggcggaaaa aacaacaac      660 gaaaccagca aaccggcgtt tagctttggc gcgaaaagcg atgaaaaaaa agatggcgat     720
gcgagcaaac cggcgtttag ctttggcgcg aaaagcgatg aaaaaaaaga tagcgatagc     780
```

```
agcaaaccgg cgtttagctt tggcaccaaa agcaacgaaa aaaagatag cggcagcagc      840 aaaccggcgt ttagctttgg cgcgaaaccg gatgaaaaaa aaaacgatga agtgagcaaa     900
ccggcgttta gctttggcgc gaaagcgaac gaaaaaaaag aaagcgatga agcaaaagc     960 gcgtttagct ttggcagcaa accgaccggc aaagaagaag gcgatggcgc gaaagcggcg    1020
attagctttg gcgcgaaacc ggaagaacag aaaagcagcg ataccagcaa accggcgttt    1080 accttttggca ccagcgcgcc gcagatgctg cgcgaactgc aggaaaccaa cgcggcgctg   1140
caggatgtgc gcgaactgct gcgccagcag gtgaaagaaa ttaccttttct gaaaaacacc   1200 gtgatggaaa gcgatgcgag c                                               1221
```

<210> SEQ ID NO 22
<211> LENGTH: 1752
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
atggatattg gcattaacag cgatccgagc accggcgcgg gcgcgtttgg caccggccag     60
agcacctttg gctttaacaa cagcgcgccg aacaacacca caacgcgaaa cagcagcatt    120
accccggcgt ttggcagcaa caacaccggc aacaccgcgt ttggcaacag caacccgacc    180
agcaacgtgt ttgcagcaa caacagcacc accaacacct tggcagcaa cagcgcgggc     240 accagcctgt ttggcagcag cagcgcgcag cagaccaaaa gcaacggcac cgcgggcggc   300 aacaccttg gcagcagcag cctgtttaac aacagcacca cagcaacac caccaaaccg    360 gcgtttggcg gcctgaactt tggcggcggc aacaacacca cccccgagcag caccggcaac   420 gcgaacacca gcaacaacct gtttggcgcg accgcgaacg cgaacaaacc ggcgtttagc   480
tttggcgcga ccaccaacga tgataaaaaa accgaaccgg ataaaccggc gtttagctt   540 aacagcagcg tgggcaacaa aaccgatgcg caggcgccga ccaccggctt tagctttggc   600
agccagctgg gcggcaacaa aaccgtgaac gaagcggcga accccgagcct gagctttggc   660 agcggcagcg cgggcgcgaa cccggcgggc gcgagccagc cggaaccgac caccaacgaa   720
ccggcgaaac cggcgctgag ctttggcacc gcgaccagcg ataacaaaac caccaacacc    780
accccgagct ttagctttgg cgcgaaaagc gatgaaaaca agcgggcgc gaccagcaaa    840 ccggcgttta gctttggcgc gaaaccggaa gaaaaaaaag atgataacag cagcaaaccg    900
gcgtttagct ttggcgcgaa agcaacgaaa gataaacagg atggcaccgc gaaaccggcg    960
tttagctttg gcgcgaaacc ggcggaaaaa aacaacaacg aaaccagcaa accggcgttt    1020
agctttggcc gaaaagcga tgaaaaaaaa gatggcgatg cgagcaaacc ggcgtttagc    1080
tttggcgcga accggatga aaacaaagcg agcgcgacca gcaaaccggc gtttagcttt    1140
ggcgcgaaac cggaagaaaa aaaagatgat aacagcagca accggcgtt tagctttggc    1200 gcgaaaagca cgaagataa acaggatggc accgcgaaac cggcgtttag ctttggcgcg    1260
aaaccggcgg aaaaaacaa caacgaaacc agcaaaccgg cgtttagctt tggcgcgaaa    1320
agcgatgaaa aaaagatgg cgatgcgagc aaaccggcgt ttagctttgg cgcgaaaagc    1380
gatgaaaaaa aagatagcga tagcagcaaa ccggcgttta gctttggcac caaaagcaac    1440
gaaaaaaaag atagcggcag cagcaaaccg gcgtttagct ttggcgcgaa accggatgaa    1500
aaaaaaaacg atgaagtgag caaaccggcg tttagctttg gcgcgaaagc gaacgaaaaa    1560
```

| | |
|---|---|
| aaagaaagcg atgaaagcaa aagcgcgttt agctttggca gcaaaccgac cggcaaagaa | 1620 |
| gaaggcgatg gcgcgaaagc ggcgattagc tttggcgcga aaccggaaga acagaaaagc | 1680 |
| agcgatacca gcaaaccggc gtttaccttt ggcaaactgg cggcggcgct ggaacatcat | 1740 |
| catcatcatc at | 1752 |

<210> SEQ ID NO 23
<211> LENGTH: 1056
<212> TYPE: DNA
<213> ORGANISM: Artificial Sequence
<220> FEATURE:
<223> OTHER INFORMATION: Description of Artificial Sequence: Synthetic
   polynucleotide

<400> SEQUENCE: 23

| | |
|---|---|
| atggatattg gcattaacag cgatccgggc agcggcagcg gcgcgagcga taacaaaacc | 60 |
| accaacacca ccccgagctt tagctttggc gcgaaaagcg atgaaaacaa agcgggcgcg | 120 |
| accagcaaac cggcgtttag ctttggcgcg aaaccggaag aaaaaaaaga tgataacagc | 180 |
| agcaaaccgg cgtttagctt tggcgcgaaa gcaacgaag ataaacagga tggcaccgcg | 240 |
| aaaccggcgt ttagctttgg cgcgaaaccg cggaaaaaa acaacaacga aaccagcaaa | 300 |
| ccggcgttta gctttggcgc gaaaagcgat gaaaaaaaag atggcgatgc gagcaaaccg | 360 |
| gcgtttagct ttggcgcgaa accggatgaa acaaagcga gcgcgaccag caaaccggcg | 420 |
| tttagctttg gcgcgaaacc ggaagaaaaa aaagatgata cagcagcaa accggcgttt | 480 |
| agctttggcg cgaaaagcaa cgaagataaa caggatggca ccgcgaaacc ggcgtttagc | 540 |
| tttggcgcga aaccggcgga aaaaacaac aacgaaacca gcaaaccggc gtttagcttt | 600 |
| ggcgcgaaaa gcgatgaaaa aaaagatggc gatgcgagca accggcgtt tagctttggc | 660 |
| gcgaaaagcg atgaaaaaaa agatagcgat agcagcaaac cggcgtttag ctttggcacc | 720 |
| aaaagcaacg aaaaaaaaga tagcggcagc agcaaaccgg cgtttagctt tggcgcgaaa | 780 |
| ccggatgaaa aaaaaacga tgaagtgagc aaaccggcgt ttagctttgg cgcgaaagcg | 840 |
| aacgaaaaaa agaaagcga tgaaagcaaa agcgcgttta gctttggcag caaaccgacc | 900 |
| ggcaaagaag aaggcgatgg cgcgaaagcg gcgattagct ttggcgcgaa accggaagaa | 960 |
| cagaaaagca gcgataccag caaaccggcg tttacctttg gcaccagcgg cagcggcaaa | 1020 |
| ctggcggcgg cgctggaaca tcatcatcat catcat | 1056 |

<210> SEQ ID NO 24
<211> LENGTH: 1638
<212> TYPE: DNA
<213> ORGANISM: Artificial Sequence
<220> FEATURE:
<223> OTHER INFORMATION: Description of Artificial Sequence: Synthetic
   polynucleotide

<400> SEQUENCE: 24

| | |
|---|---|
| atggatattg gcattaacag cgatccggcg ccgcagatgc tgcgcgaact gcaggaaacc | 60 |
| aacgcggcgc tgcaggatgt gcgcgaactg ctgcgccagc aggtgaaaga aattaccttt | 120 |
| ctgaaaaaca ccgtgatgga aagcgatgcg agcggcgcga gcgcgattag cggcgatagc | 180 |
| ctgattagcc tggcgagcac cggcaaacgc gtgagcatta aagatctgct ggatgaaaaa | 240 |
| gattttgaaa tttgggcgat taacgaacag accatgaaac tggaaagcgc gaaagtgagc | 300 |
| cgcgtgtttt gcaccggcaa aaaactggtg tatattctga aaaccgcct gggccgcacc | 360 |
| attaaagcga ccgcgaacca tcgctttctg accattgatg gctggaaacg cctggatgaa | 420 |

```
ctgagcctga agaacatat tgcgctgccg cgcaaactgg aaagcagcag cctgcagctg      480
agcccggaaa ttgaaaaact gagccagagc gatatttatt gggatagcat tgtgagcatt      540
accgaaaccg gcgtggaaga agtgtttgat ctgaccgtgc cgggcccgca taactttgtg      600
gcgaacgata ttattgtgca taacgcgagc gataacaaaa ccaccaacac caccccgagc      660
tttagctttg gcgcgaaaag cgatgaaaac aaagcgggcg cgaccagcaa accggcgttt      720
agctttggcg cgaaaccgga agaaaaaaaa gatgataaca gcagcaaacc ggcgtttagc      780
tttggcgcga aaagcaacga agataaacag gatggcaccg cgaaaccggc gtttagcttt      840
ggcgcgaaac cggcggaaaa aacaacaac gaaaccagca accggcgtt tagctttggc       900 gcgaaaagcg atgaaaaaaa agatggcgat gcgagcaaac cggcgtttag ctttggcgcg      960
aaaccggatg aaaacaaagc gagcgcgacc agcaaaccgg cgtttagctt tggcgcgaaa     1020
ccggaagaaa aaaagatga taacagcagc aaaccggcgt ttagctttgg cgcgaaaagc     1080
aacgaagata acaggatgg caccgcgaaa ccggcgttta gctttggcgc gaaaccggcg     1140
gaaaaaaaca acaacgaaac cagcaaaccg gcgtttagct ttggcgcgaa aagcgatgaa     1200
aaaaaagatg gcgatgcgag caaaccggcg tttagctttg gcgcgaaaag cgatgaaaaa     1260
aaagatagcg atagcagcaa accggcgttt agctttggca ccaaaagcaa cgaaaaaaaa     1320
gatagcggca gcagcaaacc ggcgtttagc tttggcgcga aaccggatga aaaaaaaaac     1380
gatgaagtga gcaaaccggc gtttagcttt ggcgcgaaag cgaacgaaaa aaagaaagc      1440 gatgaaagca aagcgcgtt tagctttggc agcaaaccga ccggcaaaga agaaggcgat      1500
ggcgcgaaag cggcgattag ctttggcgcg aaaccggaag aacagaaaag cagcgatacc     1560
agcaaaccgg cgtttaccctt tggcaccagc ggcagcggca aactggcggc ggcgctggaa     1620
catcatcatc atcatcat                                                   1638
```

<210> SEQ ID NO 25
<211> LENGTH: 1014
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

```
atggatattg gcattaacag cgatccgggc agcggcgcga gcccggcgtt tagctttggc        60
gcgaaaccgg atgaaaaaaa agatgatgat accagcaaac cggcgtttag ctttggcgcg       120
aaaccggatg aaaaaaaaga tgatgatacc agcaaaccgg cgtttagctt tggcgcgaaa       180
ccggatgaaa aaaagatga tgataccagc aaaccggcgt ttagctttgg cgcgaaaccg       240
gatgaaaaaa aagatgatga taccagcaaa ccggcgttta gctttggcgc gaaaccggat       300
gaaaaaaaag atgatgatac cagcaaaccg gcgtttagct ttggcgcgaa accggatgaa       360
aaaaaagatg atgataccag caaaccggcg tttagctttg gcgcgaaacc ggatgaaaaa       420
aaagatgatg ataccagcaa accggcgttt agctttggcg cgaaaccgga tgaaaaaaaa       480
gatgatgata ccagcaaaac cagcccggcg tttagctttg gcgcgaaacc ggatgaaaaa       540
aaagatgatg ataccagcaa accggcgttt agctttggcg cgaaaccgga tgaaaaaaaa       600
gatgatgata ccagcaaacc ggcgtttagc tttggcgcga aaccggatga aaaaaaagat       660
gatgatacca gcaaaccggc gtttagcttt ggcgcgaaac cggatgaaaa aaaagatgat       720
gataccagca aaccggcgtt tagctttggc gcgaaaccgg atgaaaaaaa agatgatgat       780
```

```
accagcaaac cggcgtttag ctttggcgcg aaaccggatg aaaaaaaaga tgatgatacc        840
agcaaaccgg cgtttagctt tggcgcgaaa ccggatgaaa aaaagatga tgataccagc        900 aaaccggcgt ttagctttgg cgcgaaaccg gatgaaaaaa agatgatga taccagcaaa        960 accagcggca gcggcaaact ggcggcggcg ctggaacatc atcatcatca tcat             1014
```

<210> SEQ ID NO 26
<211> LENGTH: 1023
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
atggatattg gcattaacag cgatccgggc agcggcgcga gcccggcgtt tagctttggc        60
gcgaaaccgg atgaaaaaaa agatagcgat accagcaaac cggcgtttag ctttggcgcg       120
aaaccggatg aaaaaaaaga tagcgatacc agcaaaccgg cgtttagctt tggcgcgaaa       180
ccggatgaaa aaaagatag cgataccagc aaaccggcgt ttagctttgg cgcgaaaccg        240
gatgaaaaaa agatagcga taccagcaaa ccggcgttta gctttggcgc gaaaccggat        300 gaaaaaaag atagcgatac cagcaaaccg gcgtttagct ttggcgcgaa accggatgaa        360 aaaaagata gcgataccag caaaccggcg tttagctttg gcgcgaaacc ggatgaaaaa        420
aaagatagcg ataccagcaa accggcgttt agctttggcg cgaaaccgga tgaaaaaaaa       480
gatagcgata ccagcaaaac cagcccggcg tttagctttg gcgcgaaacc ggatgaaaaa       540
aaagatagcg ataccagcaa accggcgttt agctttggcg cgaaaccgga tgaaaaaaaa       600
gatagcgata ccagcaaacc ggcgtttagc tttggcgcga accggatga aaaaaaagat        660 agcgatacca gcaaaccggc gtttagcttt ggcgcgaaac cggatgaaaa aaagatagc        720 gataccagca aaccggcgtt tagctttggc gcgaaaccgg atgaaaaaaa agatagcgat       780
accagcaaac cggcgtttag ctttggcgcg aaaccggatg aaaaaaaaga tagcgatacc       840
agcaaaccgg cgtttagctt tggcgcgaaa ccggatgaaa aaaagatagc gataccagc        900 aaaccggcgt ttagctttgg cgcgaaaccg gatgaaaaaa agatagcga taccagcaaa        960 accagcaaaa ccagcggcag cggcaaactg gcggcggcgc tggaacatca tcatcatcat      1020
cat                                                                    1023
```

<210> SEQ ID NO 27
<211> LENGTH: 1290
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
atggatattg gcattaacag cgatccggcg ccgcagatgc tgcgcgaact gcaggaaacc        60
aacgcggcgc tgcaggatgt gcgcgaactg ctgcgccagc aggtgaaaga aattaccttt       120
ctgaaaaaca ccgtgatgga aagcgatgcg agcggcgcga gcgataacaa aaccaccaac       180
accaccccga gctttagctt tggcgcgaaa agcgatgaaa caaagcgggg cgcgaccagc       240
aaaccggcgt ttagctttgg cgcgaaaccg gaagaaaaaa aagatgataa cagcagcaaa       300
ccggcgttta gctttggcgc gaaaagcaac gaagataaac aggatggcac cgcgaaaccg       360
```

```
gcgtttagct ttggcgcgaa accggcggaa aaaaacaaca acgaaaccag caaaccggcg      420
tttagctttg gcgcgaaaag cgatgaaaaa aaagatggcg atgcgagcaa accggcgttt      480
agctttggcg cgaaaccgga tgaaaacaaa gcgagcgcga ccagcaaacc ggcgtttagc      540
tttggcgcga aaccggaaga aaaaaaagat gataacagca gcaaaccggc gtttagcttt      600
ggcgcgaaaa gcaacgaaga taaacaggat ggcaccgcga aaccggcgtt tagctttggc      660
gcgaaaccgg cggaaaaaaa caacaacgaa accagcaaac cggcgtttag ctttggcgcg      720
aaaagcgatg aaaaaaaaga tggcgatgcg agcaaaccgg cgtttagctt tggcgcgaaa      780
agcgatgaaa aaaagatag cgatagcagc aaaccggcgt ttagctttgg caccaaaagc      840
aacgaaaaaa aagatagcgg cagcagcaaa ccggcgttta gctttggcgc gaaaccggat      900 gaaaaaaaa acgatgaagt gagcaaaccg gcgtttagct ttggcgcgaa agcgaacgaa      960 aaaaagaaa gcgatgaaag caaaagcgcg tttagctttg gcagcaaacc gaccggcaaa     1020
gaagaaggcg atggcgcgaa agcggcgatt agctttggcg cgaaaccgga gaacagaaa     1080 agcagcgata ccagcaaacc ggcgtttacc tttggcacca gcgcgccgca gatgctgcgc     1140
gaactgcagg aaaccaacgc ggcgctgcag gatgtgcgcg aactgctgcg ccagcaggtg     1200
aaagaaatta cctttctgaa aaacaccgtg atggaaagcg atgcgagcgg caaactggcg     1260
gcggcgctgg aacatcatca tcatcatcat                                      1290
```

<210> SEQ ID NO 28
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
atggatattg gcattaacag cgatccggcg ccgcagatgc tgcgcgaact gcaggaaacc       60
aacgcggcgc tgcaggatgt gcgcgaactg ctgcgccagc aggtgaaaga aattaccttt      120
ctgaaaaaca ccgtgatgga aagcgatgcg agcggcgcga gcccggcgtt tagctttggc      180
gcgaaaccgg atgaaaaaaa agatgatgat accagcaaac cggcgtttag ctttggcgcg      240
aaaccggatg aaaaaaaaga tgatgatacc agcaaaccgg cgtttagctt tggcgcgaaa      300
ccggatgaaa aaaagatga tgataccagc aaaccggcgt ttagctttgg cgcgaaaccg      360
gatgaaaaaa aagatgatga taccagcaaa ccggcgttta gctttggcgc gaaaccggat      420
gaaaaaaaag atgatgatac cagcaaaccg gcgtttagct ttggcgcgaa accggatgaa      480 aaaaagatg atgataccag caaaccggcg tttagctttg gcgcgaaacc ggatgaaaaa      540
aaagatgatg ataccagcaa accggcgttt agctttggcg cgaaaccgga tgaaaaaaaa      600
gatgatgata ccagcaaaac cagcccggcg tttagctttg gcgcgaaacc ggatgaaaaa      660
aaagatgatg ataccagcaa accggcgttt agctttggcg cgaaaccgga tgaaaaaaaa      720
gatgatgata ccagcaaacc ggcgtttagc tttggcgcga accggatga aaaaaaagat       780 gatgatacca gcaaaccggc gtttagctttt ggcgcgaaac cggatgaaaa aaagatgat      840 gataccagca accggcgtt tagctttggc gcgaaaccgg atgaaaaaaa agatgatgat      900
accagcaaac cggcgtttag ctttggcgcg aaaccggatg aaaaaaaaga tgatgatacc      960
agcaaaccgg cgtttagctt tggcgcgaaa ccggatgaaa aaaagatga tgataccagc     1020 aaaccggcgt ttagctttgg cgcgaaaccg gatgaaaaaa aagatgatga taccagcaaa     1080
```

```
accagcgcgc cgcagatgct gcgcgaactg caggaaacca acgcggcgct gcaggatgtg      1140
cgcgaactgc tgcgccagca ggtgaaagaa attacctttc tgaaaaacac cgtgatggaa      1200
agcgatgcga gcggcggcaa actggcggcg gcgctggaac atcatcatca tcatcat         1257
```

<210> SEQ ID NO 29
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
atggatattg cattaacag cgatccggcg ccgcagatgc tgcgcgaact gcaggaaacc        60
aacgcggcgc tgcaggatgt gcgcgaactg ctgcgccagc aggtgaaaga aattaccttt      120
ctgaaaaaca ccgtgatgga aagcgatgcg agcggcgcga gcccggcgtt tagctttggc      180
gcgaaaccgg atgaaaaaaa agatagcgat accagcaaac cggcgtttag ctttggcgcg      240
aaaccggatg aaaaaaaaga tagcgatacc agcaaaccgg cgtttagctt tggcgcgaaa      300
ccggatgaaa aaaagatag cgataccagc aaaccggcgt ttagctttgg cgcgaaaccg       360
gatgaaaaaa aagatagcga taccagcaaa ccggcgttta gctttggcgc gaaaccggat      420
gaaaaaaaag atagcgatac cagcaaaccg gcgtttagct ttggcgcgaa accggatgaa      480 aaaaagata gcgataccag caaaccggcg tttagctttg gcgcgaaacc ggatgaaaaa       540
aaagatagcg ataccagcaa accggcgttt agctttggcg cgaaaccgga tgaaaaaaaa      600
gatagcgata ccagcaaaac cagcccggcg tttagctttg gcgcgaaacc ggatgaaaaa      660
aaagatagcg ataccagcaa accggcgttt agctttggcg cgaaaccgga tgaaaaaaaa      720
gatagcgata ccagcaaacc ggcgtttagc tttggcgcga accggatgaa aaaaaagat       780 agcgatacca gcaaaccggc gtttagctttt ggcgcgaaac cggatgaaaa aaaagatagc     840
gataccagca aaccggcgtt tagctttggc gcgaaaccgg atgaaaaaaa agatagcgat      900
accagcaaac cggcgtttag cttttggcgcg aaaccggatg aaaaaaaaga tagcgatacc     960
agcaaaccgg cgtttagctt tggcgcgaaa ccggatgaaa aaaagatag cgataccagc      1020 aaaccggcgt ttagctttgg cgcgaaaccg gatgaaaaaa aagatagcga taccagcaaa     1080
accagcgcgc cgcagatgct gcgcgaactg caggaaacca acgcggcgct gcaggatgtg     1140
cgcgaactgc tgcgccagca ggtgaaagaa attacctttc tgaaaaacac cgtgatggaa     1200
agcgatgcga gcggcggcaa actggcggcg gcgctggaac atcatcatca tcatcat        1257
```

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 30

```
His His His His His His
1               5
```

ARTIFICIALLY ENGINEERED PROTEIN HYDROGELS TO MIMIC NUCLEOPORIN SELECTIVE GATING

RELATED APPLICATIONS

This application is the U.S. National Stage of PCT/US2015/036739, filed Jun. 19, 2015, which claims benefit of priority to U.S. Provisional Patent Application No. 62/015,012, filed Jun. 20, 2014.

GOVERNMENT SUPPORT

This application is the U.S. National Stage of PCT/US2015/036739, filed Jun. 19, 2015, which claims benefit of priority to U.S. Provisional Patent Application No. 62/015,012, filed Jun. 20, 2014.

SEQUENCE LISTING

The instant application contains a Sequence Listing which has been submitted electronically in ASCII format and is hereby incorporated by reference in its entirety. Said ASCII copy, created on Jun. 22, 2017, is named MTV-15601_SL.txt and is 69,998 bytes in size.

BACKGROUND OF THE INVENTION

The entry and exit of large molecules from the eukaryotic cell nucleus is tightly controlled by nuclear pore complexes (NPCs). Although small molecules can enter and exit the nucleus without regulation, macromolecules such as RNA, mRNA, ribosomal proteins, DNA polymerase, lamins, carbohydrates, signaling molecules, and lipids require association with karyopherins called importins to enter the nucleus and exportins to exit.

Nuclear pore complexes are large protein complexes that span the nuclear envelope, which is the double membrane surrounding the eukaryotic cell nucleus. The proteins that make up the nuclear pore complex are known as nucleoporins.

Nucleoporins are only required for the transport of large hydrophilic molecules above 40 kDa, as smaller molecules pass through nuclear pores via passive diffusion. For example, nucleoporins play an important role in the transport of mRNA from the nucleus to the cytoplasm after transcription. Depending on their function, certain nucleoporins are localized to a single side of the nuclear pore complex, either cytosolic or nucleoplasmic. Other nucleoporins may be found on both faces.

There are three distinct types of nucleoporins, each having a unique structure and function. These three types are structural nucleoporins, membrane nucleoporins, and FG-nucleoporins.

Structural nucleoporins form the ring portion of the NPC. They span the membrane of the nuclear envelope and are often referred to as the scaffolding of a nuclear pore. Structural nucleoporins come together to form Y-complexes that are composed of seven nucleoporins. Each nuclear pore contains sixteen Y-complexes for a total of 112 structural nucleoporins.

Membrane nucleoporins are localized to the curvature of a nuclear pore. These proteins are embedded within the nuclear membrane at the region where the inner and outer leaflets connect.

FG-nucleoporins are so named because they contain repeats of the amino acid residues phenylalanine (F) and glycine (G). FG repeats are small hydrophobic segments that break up long stretches of hydrophilic amino acids. These FG-repeat segments are found in long random-coil portions of the protein which stretch into the channel of nuclear pores and are believed to be primarily responsible for the selective exclusivity of nuclear pore complexes. These segments of FG-nucleoporins form a mass of chains which allow smaller molecules to diffuse through but exclude large hydrophilic macromolecules. These macromolecules are only able to cross a nuclear pore if they are associated with a transport molecule (karyopherin) that temporarily interacts with a nucleoporin's FG-repeat segments. FG-nucleoporins also contain a globular portion that serves as an anchor for attachment to the nuclear pore complex.

Karyopherins and their cargo are passed between FG-repeats until they diffuse down their concentration gradient and through the nuclear pore complex. The release of their cargo from karyopherins is driven by Ran, a G protein. Ran is small enough that it can diffuse through nuclear pores down its concentration gradient without interacting with nucleoporins. Ran binds to either GTP or GDP and has the ability to change a karyopherin's affinity for its cargo. Inside the nucleus, RanGTP causes an importin karyopherin to change conformation, allowing its cargo to be released. RanGTP can also bind to exportin karyopherins and pass through the nuclear pore. Once it has reached the cytosol, RanGTP can be hydrolyzed to RanGDP, allowing the exportin's cargo to be released.

Adapting artificially engineered protein polymers from consensus repeats of natural proteins is an attractive approach to mimic the unprecedented performance of natural materials. Tough silk-like polypeptides, thermoresponsive elastin-like polypeptides, and resilient and elastic resilin-like polypeptides have been synthesized to mimic the functions of natural materials. Important design principles have been developed for these artificial biopolymers that enable rational control over their thermodynamic, structural, and mechanical properties. The simplified repeat allows for a detailed understanding of sequence-structure-property relationships to be developed, and these tailor-made materials open up opportunities for applications such as drug delivery, tissue engineering, photonic films and smart responsive devices.

An additional natural material that has interesting engineering properties is the protein matrix which fills the nuclear pore complex (NPC) in the nuclear envelope and controls transport into the nucleus. It allows passage of less than 0.1% of all proteins while translocating over 1,000 molecules per pore per second. Ribbeck K et al., *EMBO J* 20: 1320 (2001); Yang W D et al., *Proc Natl Acad Sci USA* 101: 12887 (2004). The protein matrix is composed of nucleoporins, proteins containing Phe-Gly (FG) repeat sequences which contribute to specific binding of the nuclear transport receptors (NTRs) that facilitate transport of a specific subset of biological molecules into the matrix.

Individual nucleoporins can form hydrogels in vitro that recapitulate the enhanced permeability of selectively-labeled macromolecules into the gel, similar to the intact NPC, with varying degrees of passive diffusion of inert molecules. Labokha A A et al., *EMBO J* 32: 204 (2013); Jovanovic-Talisman T et al., *Nature* 457: 1023 (2009). This selectivity is rare in synthetic polymer hydrogels, making these natural materials an intriguing model for new filtration technologies. In spite of the advanced filtering function of natural nucleoporin hydrogels, until now a fundamental understanding of the sequence-structure-property relationships needed for materials engineering has been lacking, due to the complex sequence of the proteins and the inability to synthesize them recombinantly in high yields.

SUMMARY OF THE INVENTION

To adapt the function of nucleoporin hydrogels in a biosynthetic material, artificially engineered protein polymers were designed that can replicate the biological selective transport of the hydrogel in a synthetic mimic using a consensus repeat adapted from a well-investigated nucleoporin, Nsp1. Frey S et al., *Science* 314: 815 (2006); Ader C et al., *Proc Natl Acad Sci USA* 107: 6281 (2010); Frey S et al., *Cell* 130: 512 (2007). The polymers provide a valuable tool for material engineering and an opportunity to tune the selectivity, transport rates, and barrier function of nucleoporin-inspired materials through rational repeat sequence design.

As described in detail herein, designed peptides 1NLP and 2NLP, extracted from partial NspI nucleoporin, are useful for the preparation of nucleoporin-based hydrogels characterized by selective filtering capability.

As described herein, recombinant nucleoporin-like polypeptides P-1NLP-P, P-2NLP-P, and P-cNspI-P are useful for the preparation of hydrogels characterized by selective filtering capability.

As described in detail herein, hydrogels of the invention are useful as selectively permeable barriers.

Also as described in detail herein, hydrogels of the invention are useful for sequestration of compounds, including macromolecules.

Additionally, hydrogels of the invention find use as models for the nuclear pore in assays for nuclear permeability of drugs, biomaterials, nanoparticles, and other compounds.

As described in detail herein, various nuclear transport receptors, such as importin β and NTF2, can be used as carriers which can selectively bring target molecules into P-1NLP-P, P-2NLP-P, and P-cNspI-P hydrogels.

Also as described in detail herein, hydrogels of the invention are useful for collecting selected target molecules into hydrogel with nuclear transport receptor associated with target molecule-specific binding tag.

An aspect of the invention is a polypeptide comprising a plurality of contiguous instances of a subsequence represented by PAFSFGAKPDEKKDSDTSK (SEQ ID NO:1).

In certain embodiments, the polypeptide comprises 16 contiguous instances of the subsequence represented by SEQ ID NO:1.

In certain embodiments, the polypeptide consists of 16 contiguous instances of the subsequence represented by SEQ ID NO:1.

In certain embodiments, the polypeptide further comprises a first leucine zipper domain endblock flanking the N-terminal end of the plurality of contiguous instances of the subsequence represented by SEQ ID NO:1; and a second leucine zipper domain endblock flanking the C-terminal end of the plurality of contiguous instances of the subsequence represented by SEQ ID NO:1.

In certain embodiments, the leucine zipper domain endblock consists of a P domain.

In certain embodiments, the P domain consists of the peptide represented by APQMLRELQETNAALQD-VRELLRQQVKEITFLKNTVMESDAS (SEQ ID NO:3).

In certain embodiments, the polypeptide comprises the sequence represented by APQMLRELQETNAALQD-VRELLRQQVKEITFLKNTVMESDASGASPAFSFGAK-PDE KKDSDTSKPAFSFGAKPDEKKDSDTSKPAFSF-GAKPDEKKDSDTSKPAFSFGAKPD EKKDSDTSKPAFSFGAKPDEKKDSDTSKPAFSFGAK-PDEKKDSDTSKPAFSFGAKP DEKKDSDTSKPAFSF-GAKPDEKKDSDTSKTSPAFSFGAKPDEKKDSDTSK-PAFSFGA KPDEKKDSDTSKPAFSFGAKPDEKKDSDTSKPAFSF-GAKPDEKKDSDTSKPAFSFG AKPDEKKDSDTSK-PAFSFGAKPDEKKDSDTSKPAFSFGAKPDEKKDS-DTSKPAFSF GAKPDEKKDSDTSKTSAPQMLRELQETNAALQD-VRELLRQQVKEITFLKNTVMES DAS (SEQ ID NO:4).

An aspect of the invention is a polypeptide comprising a plurality of contiguous instances of a subsequence represented by PAFSFGAKPDEKKDDDTSK (SEQ ID NO:2).

In certain embodiments, the polypeptide comprises 16 contiguous instances of the subsequence represented by SEQ ID NO:2.

In certain embodiments, the polypeptide consists of 16 contiguous instances of the subsequence represented by SEQ ID NO:2.

In certain embodiments, the polypeptide further comprises a first leucine zipper domain endblock flanking the N-terminal end of the plurality of contiguous instances of the subsequence represented by SEQ ID NO:2; and a second leucine zipper domain endblock flanking the C-terminal end of the plurality of contiguous instances of the subsequence represented by SEQ ID NO:2.

In certain embodiments, the leucine zipper domain endblock consists of a P domain.

In certain embodiments, the P domain consists of the peptide represented by APQMLRELQETNAALQD-VRELLRQQVKEITFLKNTVMESDAS (SEQ ID NO:3).

In certain embodiments, the polypeptide comprises the sequence represented by APQMLRELQETNAALQD-VRELLRQQVKEITFLKNTVMESDASGASPAFSFGAK-PDE KKDDDTSKPAFSFGAKPDEKKDDDTSKPAFSF-GAKPDEKKDDDTSKPAFSFGAKPD EKKDDDTSKPAFSFGAKPDEKKDDDTSKPAFSFGAK-PDEKKDDDTSKPAFSFGAKP DEKKDDDTSKPAFSF-GAKPDEKKDDDTSKTSPAFSFGAKPDEKKDDDTSK-PAFSFG AKPDEKKDDDTSKPAFSFGAKPDEKKDDDTSK-PAFSFGAKPDEKKDDDTSKPAFSF GAKP-DEKKDDDTSKPAFSFGAKPDEKKDDDTSKPAFSF-GAKPDEKKDDDTSKPAF SFGAKPDEKKDDDTSKTSAPQMLRELQETNAALQD-VRELLRQQVKEITFLKNTVM ESDAS (SEQ ID NO:5).

An aspect of the invention is a polypeptide comprising a core sequence represented by PSFSFGAKSDENKA-GATSKPAFSFGAKPEEKKDDNSSKPAFSFGAKSNED-KQDGTA KPAFSFGAKPAEKNNNETSKPAFSFGAKS-DEKKDGDASKPAFSFGAKPDENKASAT SKPAFSFGAKPEEKKDDNSSKPAFSFGAKSNED-KQDGTAKPAFSFGAKPAEKNNNE TSKPAFSFGAKS-DEKKDGDASKPAFSFGAKSDEKKDSDSSKPAFSF-GTKSNEKKDS GSSKPAFSFGAKPDEKKNDEVSKPAFSFGAKANEK-KESDESKSAFSFGSKPTGKEE GDGAKAAISFGAKPE-EQKSSDTSK (SEQ ID NO:6); and a first leucine zipper domain endblock flanking the N-terminal end or the C-terminal end of the core sequence.

In certain embodiments, the first leucine zipper domain endblock flanks the N-terminal end of the core sequence.

In certain embodiments, the polypeptide further comprises a second zipper domain endblock flanking the C-terminal end of the core sequence.

In certain embodiments, the leucine zipper domain endblock consists of a P domain.

In certain embodiments, the P domain consists of the peptide represented by APQMLRELQETNAALQD-VRELLRQQVKEITFLKNTVMESDAS (SEQ ID NO:3).

In certain embodiments, the polypeptide comprises the sequence represented by APQMLRELQETNAALQD-VRELLRQQVKEITFLKNTVMESDASGASDNK-TTNTTPSF SFGAKSDENKAGATSKPAFSFGAKPEEK-KDDNSSKPAFSFGAKSNEDKQDGTAKP AFSFGAKPAEKNNNETSKPAFSFGAKSDEKKDG-DASKPAFSFGAKPDENKASATSK PAFSFGAKPEEK-KDDNSSKPAFSFGAKSNEDKQDGTAKPAFSFGAK-PAEKNNNETS KPAFSFGAKSDEKKDGDASKPAFSFGAKS-DEKKDSDSSKPAFSFGTKSNEKKDSGS SKPAFSF-GAKPDEKKNDEVSKPAFSFGAKANEKKESDESK-SAFSFGSKPTGKEEGD GAKAAISFGAKPEEQKSSDTSKPAFTFGTSAPQML-RELQETNAALQDVRELLRQQV KEITFLKNTVMES-DAS (SEQ ID NO:7).

An aspect of the invention is a nucleic acid molecule encoding a polypeptide of the invention.

An aspect of the invention is an expression vector comprising a nucleic acid molecule of the invention.

An aspect of the invention is a cell, comprising an expression vector of the invention.

An aspect of the invention is a hydrogel, comprising a polypeptide of the invention.

An aspect of the invention is a filtering device, comprising a hydrogel of the invention; and a housing or support for the hydrogel.

An aspect of the invention is a drug delivery device, comprising a drug; and a hydrogel of the invention.

An aspect of the invention is a method of separating or selectively filtering macromolecules, comprising contacting a source of macromolecules with a hydrogel of the invention.

In certain embodiments, the macromolecule is selected from the group consisting of RNA, mRNA, DNA, proteins, glycoproteins, carbohydrates, lipids, toxins, and any combination thereof.

BRIEF DESCRIPTION OF THE DRAWINGS

FIG. 7A is a graph depicting frequency sweep, linear oscillatory shear rheology of 20 w/v % P-cNsp1-P hydrogels in the absence (blue curves) or presence (red curves) of 10% 1,6 hexanediol. The gel modulus and the crossover frequency in the absence of hexanediol are 9.3 kPa and 0.08 rad/s.

FIG. 7B is a graph depicting frequency sweep, linear oscillatory shear rheology of 20 w/v % P-1NLP-P hydrogels in the absence (blue curves) or presence (red curves) of 10% 1,6 hexanediol. The gel modulus and the crossover frequency in the absence of hexanediol are 10.7 kPa and 0.02 rad/s.

FIG. 7C is a graph depicting frequency sweep, linear oscillatory shear rheology of 20 w/v % P-2NLP-P hydrogels in the absence (blue curves) or presence (red curves) of 10% 1,6 hexanediol. The gel modulus and the crossover frequency in the absence of hexanediol are 7.5 kPa and 0.04 rad/s.

FIG. 7D is a graph depicting frequency sweep, linear oscillatory shear rheology of 20 w/v % P-$C_{30}$-P gel, which lacks FG repeats in its midblock. C is a peptide having amino acid sequence AGAGAGPEG (SEQ ID NO:8).

FIG. 7E is a graph depicting Raman spectra of 20 w/v % cNsp1 midblocks, measured in buffer containing 50 mM Tris/HCl (pH 7.5) and 200 mM NaCl (blue curve) and with the addition of 10% hexanediol (red curve). The shaded boxes highlight Raman bands of 486, 685 and 710 $cm^{-1}$ that decrease in intensity with the addition of hexanediol.

FIG. 7F is a graph depicting Raman spectra of 20 w/v % 1NLP midblocks, measured in buffer containing 50 mM Tris/HCl (pH 7.5) and 200 mM NaCl (blue curve) and with the addition of 10% hexanediol (red curve). The shaded boxes highlight Raman bands of 486, 685 and 710 $cm^{-1}$ that decrease in intensity with the addition of hexanediol.

FIG. 7G is a graph depicting Raman spectra of 20 w/v % 2NLP midblocks, measured in buffer containing 50 mM Tris/HCl (pH 7.5) and 200 mM NaCl (blue curve) and with the addition of 10% hexanediol (red curve). The shaded boxes highlight Raman bands of 486, 685 and 710 cm$^{-1}$ that decrease in intensity with the addition of hexanediol.

DETAILED DESCRIPTION OF THE INVENTION

Recent in vitro results indicate that the recombinant Nsp1$^{2-601}$ can be divided into an N-terminal sequence Nsp1$^{2-277}$ and a C-terminal sequence Nsp1$^{274-601}$. Ader C et al., *Proc Natl Acad Sci USA* 107: 6281 (2010). In Nsp1, the C-terminal sequence contributes to selective transport of NTR-cargo complexes and less non-specific binding of inert molecules, core functions for selective transport. However, the C-terminal sequence alone forms a liquid that cannot restrict the passage of inert molecules. The N-terminal sequence is critical for gelation, suggesting that network formation is required for a fully functional selective transport system.

To prepare synthetic gels, the N-terminal sequence of Nsp1, which gels slowly over a period of hours, was replaced with well-investigated pentameric (P) coiled-coil domains flanking the C-terminal sequence (cNsp1). Petka W A et al., *Science* 281: 389 (1998); Shen W et al., *Nat Mater* 5: 153 (2006); Olsen B D et al., *Macromolecules* 43: 9094 (2010). This triblock protein construct, P-cNsp1-P, gels in minutes, and the transient interactions of the P domains allow network relaxation that is thought to be critical to transport. Ribbeck K et al., *EMBO J* 20: 1320 (2001).

Analysis of the cNsp1 consensus sequence ($Nsp1^{282-585}$) allows reduction of the protein to a polymer of short repeating segments. $Nsp1^{282-585}$ is composed of 16 repeats of a 19-amino acid Phe-Gly (FG)-containing sequence, with a high consensus at each position except position 15, where equal numbers of Asp (D) and Ser (S) are observed. To elucidate the 16 consecutive 19-amino acid segments, the 304-amino acid sequence of $Nsp1^{282-585}$ (SEQ ID NO:9) can be written thus:

PSFSFGAKSDENKAGATSK

PAFSFGAKPEEKKDDNSSK

PAFSFGAKSNEDKQDGTAK

PAFSFGAKPAEKNNNETSK

PAFSFGAKSDEKKDGDASK

PAFSFGAKPDENKASATSK

PAFSFGAKPEEKKDDNSSK

PAFSFGAKSNEDKQDGTAK

PAFSFGAKPAEKNNNETSK

```
-continued
PAFSFGAKSDEKKDGDASK

PAFSFGAKSDEKKDSDSSK

PAFSFGTKSNEKKDSGSSK

PAFSFGAKPDEKKNDEVSK

PAFSFGAKANEKKESDESK

SAFSFGSKPTGKEEGDGAK

AAISFGAKPEEQKSSDTSK
``` where the repeating FG sequences and the D and S residues at position 15 are shown in bold.

Figure 1A:
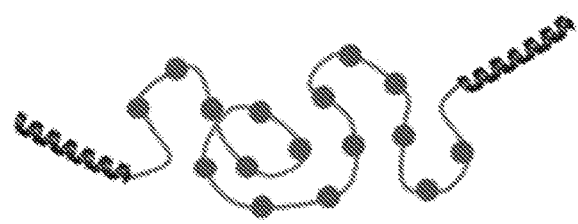
FIG. 1A depicts design of synthetic protein polymers, P-cNsp1-P and P-NLPs-P, which gel by association of pentameric (P) coiled-coil endblock domains (coils). Filled circles represent Phe-Gly (FG) sequences.
Figure 1B:
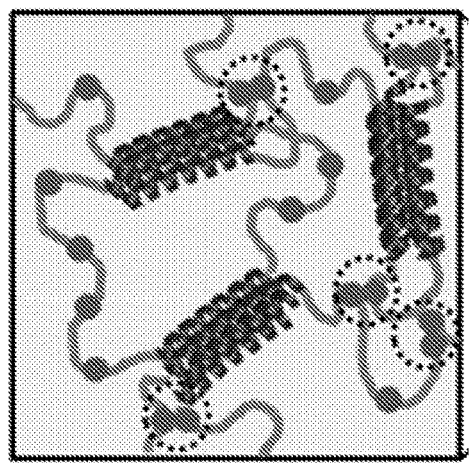
FIG. 1B depicts 3D gel network formed from assembly of designed artificially engineered proteins. Black dotted circles highlight Phe-mediated interactions within synthetic hydrogels.

To capture the highest frequency of occurrence in all positions of cNsp1, two separate repeat units were designed: one where position 15 was Asp (D) (PAFSFGAKP-DEKKDDDTSK; SEQ ID NO:2), and another where position 15 was Ser (S) (PAFSFGAKPDEKKDSDTSK; SEQ ID NO:1). These sequences were cloned to form an artificial protein polymer of 16 such units, producing two nucleoporin-like polypeptides (NLPs) denoted 1NLP and 2NLP, respectively. Both NLPs were genetically fused with P domain endblocks (P-1NLP-P and P-2NLP-P, FIG. 1A) to construct polymers that form gels due to coiled-coil physical association (FIG. 1B). Since these simplified NLP polymers can mimic the properties of natural cNsp1, the polymers represent a valuable tool for material engineering and an opportunity to tune the selectivity, transport rates and barrier function of nucleoporin-inspired materials through rational repeat sequence design.

Compounds of the Invention

2NLP

An aspect of the invention is a polypeptide comprising a plurality of contiguous instances of a subsequence represented by PAFSFGAKPDEKKDSDTSK (SEQ ID NO:1).

In certain embodiments, the polypeptide consists of a plurality of contiguous instances of a subsequence represented by SEQ ID NO:1.

In certain embodiments, the polypeptide comprises 16 contiguous instances of the subsequence represented by SEQ ID NO:1.

In certain embodiments, the polypeptide consists of 16 contiguous instances of the subsequence represented by SEQ ID NO:1.

In certain embodiments, the polypeptide further comprises a first leucine zipper domain endblock flanking the N-terminal end of the plurality of contiguous instances of the subsequence represented by SEQ ID NO:1.

In certain embodiments, the polypeptide further comprises a first leucine zipper domain endblock flanking the C-terminal end of the plurality of contiguous instances of the subsequence represented by SEQ ID NO:1.

In certain embodiments, the first leucine zipper domain endblock comprises a pentameric coiled-coil domain (P domain).

In certain embodiments, the first leucine zipper domain endblock consists of a pentameric coiled-coil domain (P domain).

In certain embodiments, the P domain comprises the peptide represented by APQMLRELQETNAALQD-VRELLRQQVKEITFLKNTVMESDAS (SEQ ID NO:3).

In certain embodiments, the P domain consists of the peptide represented by APQMLRELQETNAALQD-VRELLRQQVKEITFLKNTVMESDAS (SEQ ID NO:3).

In certain embodiments, the polypeptide further comprises a first leucine zipper domain endblock flanking the N-terminal end of the plurality of contiguous instances of the subsequence represented by SEQ ID NO:1; and a second leucine zipper domain endblock flanking the C-terminal end of the plurality of contiguous instances of the subsequence represented by SEQ ID NO:1.

In certain embodiments, the first leucine zipper domain endblock comprises a P domain.

In certain embodiments, the first leucine zipper domain endblock consists of a P domain.

In certain embodiments, the first leucine zipper domain endblock P domain comprises the peptide represented by APQMLRELQETNAALQDVRELLRQQVKEITFLKNT-VMESDAS (SEQ ID NO:3).

In certain embodiments, the first leucine zipper domain endblock P domain consists of the peptide represented by APQMLRELQETNAALQDVRELLRQQVKEITFLKNT-VMESDAS (SEQ ID NO:3).

In certain embodiments, the second leucine zipper domain endblock comprises a P domain.

In certain embodiments, the second leucine zipper domain endblock consists of a P domain.

In certain embodiments, the second leucine zipper domain endblock P domain comprises the peptide represented by APQMLRELQETNAALQDVRELLRQQVKEITFLKNT-VMESDAS (SEQ ID NO:3).

In certain embodiments, the second leucine zipper domain endblock P domain consists of the peptide represented by APQMLRELQETNAALQDVRELLRQQVKEITFLKNT-VMESDAS (SEQ ID NO:3).

In certain embodiments, the first leucine zipper domain endblock comprises a P domain; and the second leucine zipper domain endblock comprises a P domain.

In certain embodiments, the first leucine zipper domain endblock comprises a P domain; and the second leucine zipper domain endblock consists of a P domain.

In certain embodiments, the first leucine zipper domain endblock consists of a P domain; and the second leucine zipper domain endblock comprises a P domain.

In certain embodiments, the first leucine zipper domain endblock consists of a P domain; and the second leucine zipper domain endblock consists of a P domain.

In certain embodiments, the first leucine zipper domain endblock P domain comprises the peptide represented by SEQ ID NO:3; and the second leucine zipper domain endblock P domain comprises the peptide represented by SEQ ID NO:3.

In certain embodiments, the first leucine zipper domain endblock P domain comprises the peptide represented by SEQ ID NO:3; and the second leucine zipper domain endblock P domain consists of the peptide represented by SEQ ID NO:3.

In certain embodiments, the first leucine zipper domain endblock P domain consists of the peptide represented by SEQ ID NO:3; and the second leucine zipper domain endblock P domain comprises the peptide represented by SEQ ID NO:3.

In certain embodiments, the first leucine zipper domain endblock P domain consists of the peptide represented by SEQ ID NO:3; and the second leucine zipper domain endblock P domain consists of the peptide represented by SEQ ID NO:3.

In certain embodiments, the polypeptide comprises the sequence represented by APQMLRELQETNAALQD-VRELLRQQVKEITFLKNTVMESDASGASPAFSFGAK-PDE KKDSDTSKPAFSFGAKPDEKKDSDTSKPAFSF- GAKPDEKKDSDTSKPAFSFGAKPD EKKDSDTSKPAFSFGAKPDEKKDSDTSKPAFSFGAK-PDEKKDSDTSKPAFSFGAKP DEKKDSDTSKPAFSF-GAKPDEKKDSDTSKTSPAFSFGAKPDEKKDSDTSK-PAFSFGA KPDEKKDSDTSKPAFSFGAKPDEKKDSDTSKPAFSF-GAKPDEKKDSDTSKPAFSFG AKPDEKKDSDTSK-PAFSFGAKPDEKKDSDTSKPAFSFGAKPDEKKDS-DTSKPAFSF GAKPDEKKDSDTSKTSAPQMLRELQETNAALQD-VRELLRQQVKEITFLKNTVMES DAS (SEQ ID NO:4).

In certain embodiments, the polypeptide consists of the sequence represented by APQMLRELQETNAALQD-VRELLRQQVKEITFLKNTVMESDASGASPAFSFGAK-PDE KKDSDTSKPAFSFGAKPDEKKDSDTSKPAFSF-GAKPDEKKDSDTSKPAFSFGAKPD EKKDSDTSKPAFSFGAKPDEKKDSDTSKPAFSFGAK-PDEKKDSDTSKPAFSFGAKP DEKKDSDTSKPAFSF-GAKPDEKKDSDTSKTSPAFSFGAKPDEKKDSDTSK-PAFSFGA KPDEKKDSDTSKPAFSFGAKPDEKKDSDTSKPAFSF-GAKPDEKKDSDTSKPAFSFG AKPDEKKDSDTSK-PAFSFGAKPDEKKDSDTSKPAFSFGAKPDEKKDS-DTSKPAFSF GAKPDEKKDSDTSKTSAPQMLRELQETNAALQD-VRELLRQQVKEITFLKNTVMES DAS (SEQ ID NO:4).
1NLP An aspect of the invention is a polypeptide comprising a plurality of contiguous instances of a subsequence represented by PAFSFGAKPDEKKDDDTSK (SEQ ID NO:2).

In certain embodiments, the polypeptide consists of a plurality of contiguous instances of a subsequence represented by SEQ ID NO:2.

In certain embodiments, the polypeptide comprises 16 contiguous instances of the subsequence represented by SEQ ID NO:2.

In certain embodiments, the polypeptide consists of 16 contiguous instances of the subsequence represented by SEQ ID NO:2.

In certain embodiments, the polypeptide further comprises a first leucine zipper domain endblock flanking the N-terminal end of the plurality of contiguous instances of the subsequence represented by SEQ ID NO:2.

In certain embodiments, the polypeptide further comprises a first leucine zipper domain endblock flanking the C-terminal end of the plurality of contiguous instances of the subsequence represented by SEQ ID NO:2.

In certain embodiments, the first leucine zipper domain endblock comprises a pentameric coiled-coil domain (P domain).

In certain embodiments, the first leucine zipper domain endblock consists of a pentameric coiled-coil domain (P domain).

In certain embodiments, the P domain comprises the peptide represented by APQMLRELQETNAALQD-VRELLRQQVKEITFLKNTVMESDAS (SEQ ID NO:3).

In certain embodiments, the P domain consists of the peptide represented by APQMLRELQETNAALQD-VRELLRQQVKEITFLKNTVMESDAS (SEQ ID NO:3).

In certain embodiments, the polypeptide further comprises a first leucine zipper domain endblock flanking the N-terminal end of the plurality of contiguous instances of the subsequence represented by SEQ ID NO:2; and a second leucine zipper domain endblock flanking the C-terminal end of the plurality of contiguous instances of the subsequence represented by SEQ ID NO:2.

In certain embodiments, the first leucine zipper domain endblock comprises a P domain.

In certain embodiments, the first leucine zipper domain endblock consists of a P domain.

In certain embodiments, the first leucine zipper domain endblock P domain comprises the peptide represented by APQMLRELQETNAALQDVRELLRQQVKEITFLKNT-VMESDAS (SEQ ID NO:3).

In certain embodiments, the first leucine zipper domain endblock P domain consists of the peptide represented by APQMLRELQETNAALQDVRELLRQQVKEITFLKNT-VMESDAS (SEQ ID NO:3).

In certain embodiments, the second leucine zipper domain endblock comprises a P domain.

In certain embodiments, the second leucine zipper domain endblock consists of a P domain.

In certain embodiments, the second leucine zipper domain endblock P domain comprises the peptide represented by APQMLRELQETNAALQDVRELLRQQVKEITFLKNT-VMESDAS (SEQ ID NO:3).

In certain embodiments, the second leucine zipper domain endblock P domain consists of the peptide represented by APQMLRELQETNAALQDVRELLRQQVKEITFLKNT-VMESDAS (SEQ ID NO:3).

In certain embodiments, the first leucine zipper domain endblock comprises a P domain; and the second leucine zipper domain endblock comprises a P domain.

In certain embodiments, the first leucine zipper domain endblock comprises a P domain; and the second leucine zipper domain endblock consists of a P domain.

In certain embodiments, the first leucine zipper domain endblock consists of a P domain; and the second leucine zipper domain endblock comprises a P domain.

In certain embodiments, the first leucine zipper domain endblock consists of a P domain; and the second leucine zipper domain endblock consists of a P domain.

In certain embodiments, the first leucine zipper domain endblock P domain comprises the peptide represented by SEQ ID NO:3; and the second leucine zipper domain endblock P domain comprises the peptide represented by SEQ ID NO:3.

In certain embodiments, the first leucine zipper domain endblock P domain comprises the peptide represented by SEQ ID NO:3; and the second leucine zipper domain endblock P domain consists of the peptide represented by SEQ ID NO:3.

In certain embodiments, the first leucine zipper domain endblock P domain consists of the peptide represented by SEQ ID NO:3; and the second leucine zipper domain endblock P domain comprises the peptide represented by SEQ ID NO:3.

In certain embodiments, the first leucine zipper domain endblock P domain consists of the peptide represented by SEQ ID NO:3; and the second leucine zipper domain endblock P domain consists of the peptide represented by SEQ ID NO:3.

In certain embodiments, the polypeptide comprises the sequence represented by APQMLRELQETNAALQD-VRELLRQQVKEITFLKNTVMESDASGASPAFSFGAK-PDE KKDDDTSKPAFSFGAKPDEKKDDDTSKPAFSF-GAKPDEKKDDDTSKPAFSFGAKPD EKKDDDTSKPAFSFGAKPDEKKDDDTSKPAFSFGAK-PDEKKDDDTSKPAFSFGAKP DEKKDDDTSKPAFSF-GAKPDEKKDDDTSKTSPAFSFGAKPDEKKDDDTSK-PAFSFG AKPDEKKDDDTSKPAFSFGAKPDEKKDDDTSK-PAFSFGAKPDEKKDDDTSKPAFSF GAKP- DEKKDDDTSKPAFSFGAKPDEKKDDDTSKPAFSF-
GAKPDEKKDDDTSKPAF
SFGAKPDEKKDDDTSKTSAPQMLRELQETNAALQD-
VRELLRQQVKEITFLKNTVM ESDAS (SEQ ID NO:5).

In certain embodiments, the polypeptide consists of the sequence represented by APQMLRELQETNAALQD-VRELLRQQVKEITFLKNTVMESDASGASPAFSFGAK-PDE KKDDDTSKPAFSFGAKPDEKKDDDTSKPAFSF-GAKPDEKKDDDTSKPAFSFGAKPD EKKDDDTSKPAFSFGAKPDEKKDDDTSKPAFSFGAK-PDEKKDDDTSKPAFSFGAKP DEKKDDDTSKPAFSF-GAKPDEKKDDDTSKTSPAFSFGAKPDEKKDDDTSK-PAFSFG AKPDEKKDDDTSKPAFSFGAKPDEKKDDDTSK-PAFSFGAKPDEKKDDDTSKPAFSF GAKP-DEKKDDDTSKPAFSFGAKPDEKKDDDTSKPAFSF-GAKPDEKKDDDTSKPAF SFGAKPDEKKDDDTSKTSAPQMLRELQETNAALQD-VRELLRQQVKEITFLKNTVM ESDAS (SEQ ID NO:5).

cNsp1

An aspect of the invention is a polypeptide comprising a core sequence represented by PSFSFGAKSDENKA-GATSKPAFSFGAKPEEKKDDNSSKPAFSFGAKSNED-KQDGTA KPAFSFGAKPAEKNNNETSKPAFSFGAKS-DEKKDGDASKPAFSFGAKPDENKASAT SKPAFSFGAKPEEKKDDNSSKPAFSFGAKSNED-KQDGTAKPAFSFGAKPAEKNNNE TSKPAFSFGAKS-DEKKDGDASKPAFSFGAKSDEKKDSDSSKPAFSF-GTKSNEKKDS GSSKPAFSFGAKPDEKKNDEVSKPAFSFGAKANEK-KESDESKSAFSFGSKPTGKEE GDGAKAAISFGAKPE-EQKSSDTSK (SEQ ID NO:6); and a first leucine zipper domain endblock flanking the N-terminal end or the C-terminal end of the core sequence.

In certain embodiments, the polypeptide consists of a core sequence represented by PSFSFGAKSDENKAGATSK-PAFSFGAKPEEKKDDNSSKPAFSFGAKSNED-KQDGTA KPAFSFGAKPAEKNNNETSKPAFSFGAKS-DEKKDGDASKPAFSFGAKPDENKASAT SKPAFSFGAKPEEKKDDNSSKPAFSFGAKSNED-KQDGTAKPAFSFGAKPAEKNNNE TSKPAFSFGAKS-DEKKDGDASKPAFSFGAKSDEKKDSDSSKPAFSF-GTKSNEKKDS GSSKPAFSFGAKPDEKKNDEVSKPAFSFGAKANEK-KESDESKSAFSFGSKPTGKEE GDGAKAAISFGAKPE-EQKSSDTSK (SEQ ID NO:6); and a first leucine zipper domain endblock flanking the N-terminal end or the C-terminal end of the core sequence.

In certain embodiments, the first leucine zipper domain endblock flanks the N-terminal end of the core sequence.

In certain embodiments, the first leucine zipper domain endblock flanks the C-terminal end of the core sequence.

In certain embodiments, the first leucine zipper domain endblock comprises a pentameric coiled-coil domain (P domain).

In certain embodiments, the first leucine zipper domain endblock consists of a pentameric coiled-coil domain (P domain).

In certain embodiments, the first leucine zipper domain endblock P domain comprises the peptide represented by APQMLRELQETNAALQDVRELLRQQVKEITFLKNT-VMESDAS (SEQ ID NO:3).

In certain embodiments, the first leucine zipper domain endblock P domain consists of the peptide represented by APQMLRELQETNAALQDVRELLRQQVKEITFLKNT-VMESDAS (SEQ ID NO:3).

In certain embodiments, the polypeptide comprises the core domain, the first leucine zipper domain endblock flanking the N-terminal end of the core sequence, and a second leucine zipper domain endblock flanking the C-terminal end of the core sequence.

In certain embodiments, the polypeptide consists of the core domain, the first leucine zipper domain endblock flanking the N-terminal end of the core sequence, and a second leucine zipper domain endblock flanking the C-terminal end of the core sequence.

In certain embodiments, the first leucine zipper domain endblock P domain comprises the peptide represented by SEQ ID NO:3; and the second leucine zipper domain endblock P domain comprises the peptide represented by SEQ ID NO:3.

In certain embodiments, the first leucine zipper domain endblock P domain comprises the peptide represented by SEQ ID NO:3; and the second leucine zipper domain endblock P domain consists of the peptide represented by SEQ ID NO:3.

In certain embodiments, the first leucine zipper domain endblock P domain consists of the peptide represented by SEQ ID NO:3; and the second leucine zipper domain endblock P domain comprises the peptide represented by SEQ ID NO:3.

In certain embodiments, the first leucine zipper domain endblock P domain consists of the peptide represented by SEQ ID NO:3; and the second leucine zipper domain endblock P domain consists of the peptide represented by SEQ ID NO:3.

In certain embodiments, the polypeptide comprises the sequence represented by APQMLRELQETNAALQD-VRELLRQQVKEITFLKNTVMESDASGASDNK-TTNTTPSF SFGAKSDENKAGATSKPAFSFGAKPEEK-KDDNSSKPAFSFGAKSNEDKQDGTAKP AFSFGAKPAEKNNNETSKPAFSFGAKSDEKKDG-DASKPAFSFGAKPDENKASATSK PAFSFGAKPEEK-KDDNSSKPAFSFGAKSNEDKQDGTAKPAFSFGAK-PAEKNNNETS KPAFSFGAKSDEKKDGDASKPAFSFGAKS-DEKKDSDSSKPAFSFGTKSNEKKDSGS SKPAFSF-GAKPDEKKNDEVSKPAFSFGAKANEKKESDESK-SAFSFGSKPTGKEEGD GAKAAISFGAKPEEQKSSDTSKPAFTFGTSAPQML-RELQETNAALQDVRELLRQQV KEITFLKNTVMES-DAS (SEQ ID NO:7).

In certain embodiments, the polypeptide consists of the sequence represented by APQMLRELQETNAALQD-VRELLRQQVKEITFLKNTVMESDASGASDNK-TTNTTPSF SFGAKSDENKAGATSKPAFSFGAKPEEK-KDDNSSKPAFSFGAKSNEDKQDGTAKP AFSFGAKPAEKNNNETSKPAFSFGAKSDEKKDG-DASKPAFSFGAKPDENKASATSK PAFSFGAKPEEK-KDDNSSKPAFSFGAKSNEDKQDGTAKPAFSFGAK-PAEKNNNETS KPAFSFGAKSDEKKDGDASKPAFSFGAKS-DEKKDSDSSKPAFSFGTKSNEKKDSGS SKPAFSF-GAKPDEKKNDEVSKPAFSFGAKANEKKESDESK-SAFSFGSKPTGKEEGD GAKAAISFGAKPEEQKSSDTSKPAFTFGTSAPQML-RELQETNAALQDVRELLRQQV KEITFLKNTVMES-DAS (SEQ ID NO:7).

An aspect of the invention is a nucleic acid molecule encoding a polypeptide of the invention.

In one embodiment, the nucleic acid molecule encodes a polypeptide represented by SEQ ID NO:4. For example, in one embodiment, a DNA sequence encoding SEQ ID NO:4 is:

(SEQ ID NO: 18)
gcgccgcagatgctgcgcgaactgcaggaaaccaacgcggcgctgcagga tgtgcgcgaactgctgcgccagcaggtgaaagaaattacctttctgaaaa acaccgtgatggaaagcgatgcgagcggcgcgagcccggcgtttagctttt ggcgcgaaaccggatgaaaaaaaagatagcgataccagcaaaccggcgtt tagctttggcgcgaaaccggatgaaaaaaaagatagcgataccagcaaac cggcgtttagctttggcgcgaaaccggatgaaaaaaaagatagcgatacc agcaaaccggcgtttagctttggcgcgaaaccggatgaaaaaaaagatag cgataccagcaaaccggcgtttagctttggcgcgaaaccggatgaaaaaa aagatagcgataccagcaaaccggcgtttagctttggcgcgaaaccggat gaaaaaaaagatagcgataccagcaaaccggcgtttagctttggcgcgaa accggatgaaaaaaaagatagcgataccagcaaaccggcgtttagctttg gcgcgaaaccggatgaaaaaaaagatagcgataccagcaaaaccagcccg gcgtttagctttggcgcgaaaccggatgaaaaaaaagatagcgataccag caaaccggcgtttagctttggcgcgaaaccggatgaaaaaaaagatagcg ataccagcaaaccggcgtttagctttggcgcgaaaccggatgaaaaaaaa gatagcgataccagcaaaccggcgtttagctttggcgcgaaaccggatga aaaaaaagatagcgataccagcaaaccggcgtttagctttggcgcgaaac cggatgaaaaaaaagatagcgataccagcaaaccggcgtttagctttggc gcgaaaccggatgaaaaaaaagatagcgataccagcaaaccggcgtttag ctttggcgcgaaaccggatgaaaaaaaagatagcgataccagcaaaccgg cgtttagctttggcgcgaaaccggatgaaaaaaaagatagcgataccagc aaaaccagcgcgccgcagatgctgcgcgaactgcaggaaaccaacgcggc gctgcaggatgtgcgcgaactgctgcgccagcaggtgaaagaaattacct ttctgaaaaacaccgtgatggaaagcgatgcgagc.

In one embodiment, the nucleic acid molecule encodes a polypeptide represented by SEQ ID NO:5. For example, in one embodiment, a DNA sequence encoding SEQ ID NO:5 is:

(SEQ ID NO: 19)
gcgccgcagatgctgcgcgaactgcaggaaaccaacgcggcgctgcagga tgtgcgcgaactgctgcgccagcaggtgaaagaaattacctttctgaaaa acaccgtgatggaaagcgatgcgagcggcgcgagcccggcgtttagctttt ggcgcgaaaccggatgaaaaaaaagatgatgataccagcaaaccggcgtt tagctttggcgcgaaaccggatgaaaaaaaagatgatgataccagcaaac cggcgtttagctttggcgcgaaaccggatgaaaaaaaagatgatgatacc agcaaaccggcgtttagctttggcgcgaaaccggatgaaaaaaaagatga tgataccagcaaaccggcgtttagctttggcgcgaaaccggatgaaaaaa aagatgatgataccagcaaaccggcgtttagctttggcgcgaaaccggat gaaaaaaaagatgatgataccagcaaaccggcgtttagctttggcgcgaa accggatgaaaaaaaagatgatgataccagcaaaccggcgtttagctttg gcgcgaaaccggatgaaaaaaaagatgatgataccagcaaaaccagcccg gcgtttagctttggcgcgaaaccggatgaaaaaaaagatgatgataccag caaaccggcgtttagctttggcgcgaaaccggatgaaaaaaaagatgatg ataccagcaaaccggcgtttagctttggcgcgaaaccggatgaaaaaaaa gatgatgataccagcaaaccggcgtttagctttggcgcgaaaccggatga aaaaaaagatgatgataccagcaaaccggcgtttagctttggcgcgaaac cggatgaaaaaaaagatgatgataccagcaaaccggcgtttagctttggc gcgaaaccggatgaaaaaaaagatgatgataccagcaaaccggcgtttag ctttggcgcgaaaccggatgaaaaaaaagatgatgataccagcaaaccgg cgtttagctttggcgcgaaaccggatgaaaaaaaagatgatgataccagc aaaaccagcgcgccgcagatgctgcgcgaactgcaggaaaccaacgcggc gctgcaggatgtgcgcgaactgctgcgccagcaggtgaaagaaattacct ttctgaaaaacaccgtgatggaaagcgatgcgagc.

In one embodiment, the nucleic acid molecule encodes a polypeptide represented by SEQ ID NO:6. For example, in one embodiment, a DNA sequence encoding SEQ ID NO:6 is:

(SEQ ID NO: 20)
ccgagctttagctttggcgcgaaaagcgatgaaaacaaagcgggcgcgac cagcaaaccggcgtttagctttggcgcgaaaccggaagaaaaaaaagatg ataacagcagcaaaccggcgtttagctttggcgcgaaaagcaacgaagat aaacaggatggcaccgcgaaaccggcgtttagctttggcgcgaaaccggc ggaaaaaaacaacaacgaaaccagcaaaccggcgtttagctttggcgcga aaagcgatgaaaaaaaagatggcgatgcgagcaaaccggcgtttagcttt ggcgcgaaaccggatgaaaacaaagcgagcgcgaccagcaaaccggcgtt tagctttggcgcgaaaccggaagaaaaaaaagatgataacagcagcaaac cggcgtttagctttggcgcgaaaagcaacgaagataaacaggatggcacc gcgaaaccggcgtttagctttggcgcgaaaccggcggaaaaaaacaacaa cgaaaccagcaaaccggcgtttagctttggcgcgaaaagcgatgaaaaaa aagatggcgatgcgagcaaaccggcgtttagctttggcgcgaaaagcgat gaaaaaaaagatagcgatagcagcaaaccggcgtttagctttggcaccaa aagcaacgaaaaaaaagatagcggcagcagcaaaccggcgtttagctttg gcgcgaaaccggatgaaaaaaaaacgatgaagtgagcaaaccggcgttt agctttggcgcgaaagcgaacgaaaaaaaagaaagcgatgaaagcaaag cgcgtttagctttggcagcaaaccgaccggcaaagaagaaggcgatggcg cgaaagcggcgattagctttggcgcgaaaccggaagaacagaaaagcagc gataccagcaaa.

In one embodiment, the nucleic acid molecule encodes a polypeptide represented by SEQ ID NO:7. For example, in one embodiment, a DNA sequence encoding SEQ ID NO: 7 is:

```
                                            (SEQ ID NO: 21)
gcgccgcagatgctgcgcgaactgcaggaaaccaacgcggcgctgcagga tgtgcgcgaactgctgcgccagcaggtgaaagaaattacctttctgaaaa acaccgtgatggaaagcgatgcgagcggcgcgagcgataacaaaaccacc aacaccaccccgagctttagctttggcgcgaaaagcgatgaaaacaaagc gggcgcgaccagcaaaccggcgtttagctttggcgcgaaaccggaagaaa aaaaagatgataacagcagcaaaccggcgtttagctttggcgcgaaaagc aacgaagataaacaggatggcaccgcgaaaccggcgtttagctttggcgc gaaaccggcggaaaaaacaacaacgaaaccagcaaaccggcgtttagct ttggcgcgaaaagcgatgaaaaaaagatggcgatgcgagcaaaccggcg tttagctttggcgcgaaaccggatgaaaacaaagcgagcgcgaccagcaa accggcgtttagctttggcgcgaaaccggaagaaaaaaaagatgataaca gcagcaaaccggcgtttagctttggcgcgaaaagcaacgaagataaacag gatggcaccgcgaaaccggcgtttagctttggcgcgaaaccggcggaaaa aaacaacaacgaaaccagcaaaccggcgtttagctttggcgcgaaaagcg atgaaaaaaagatggcgatgcgagcaaaccggcgtttagctttggcgcg aaaagcgatgaaaaaaagatagcgatagcagcaaaccggcgtttagctt tggcaccaaaagcaacgaaaaaaaagatagcggcagcagcaaaccggcgt ttagctttggcgcgaaaccggatgaaaaaaaaacgatgaagtgagcaaa ccggcgtttagctttggcgcgaaaagcgaacgaaaaaaaagaaagcgatga agcaaaagcgcgtttagctttggcagcaaaccgaccggcaaagaagaag gcgatggcgcgaaagcggcgattagctttggcgcgaaaccggaagaacag aaaagcagcgataccagcaaaccggcgtttacctttggcaccagcgcgcc gcagatgctgcgcgaactgcaggaaaccaacgcggcgctgcaggatgtgc gcgaactgctgcgccagcaggtgaaagaaattacctttctgaaaaacacc gtgatggaaagcgatgcgagc.
```

In one embodiment, the nucleic acid molecule encodes a polypeptide represented by SEQ ID NO:10 (see below). For example, in one embodiment, a DNA sequence encoding SEQ ID NO:10 is:

```
                                            (SEQ ID NO: 22)
atggatattggcattaacagcgatccgagcaccggcgcgggcgcgtttgg caccggccagagcacctttggctttaacaacagcgcgccgaacaacacca caacgcgaacagcagcattaccccggcgtttggcagcaacaacaccggc aacaccgcgtttggcaacagcaacccgaccagcaacgtgtttggcagcaa caacagcaccaccaacacctttggcagcaacagcgcgggcaccagcctgt tggcagcagcagcgcgcagcagaccaaaagcaacggcaccgcgggcggc aacaccttggcagcagcagcctgtttaacaacagcaccaacagcaacac caccaaaccggcgtttggcggcctgaactttggcggcggcaacaacacca ccccgagcagcaccggcaacgcgaacaccagcaacaacctgtttggcgcg accgcgaacgcgaacaaaccggcgtttagctttggcgcgaccaccaacga tgataaaaaaaccgaaccggataaaccggcgtttagctttaacagcagcg
```

```
-continued
tgggcaacaaaaccgatgcgcaggcgccgaccaccggctttagctttggc agccagctgggcggcaacaaaaccgtgaacgaagcggcgaaaccgagcct gagctttggcagcggcagcgcgggcgcgaacccggcgggcgcgagccagc cggaaccgaccaccaacgaaccggcgaaaccggcgctgagctttggcacc gcgaccagcgataacaaaaccaccaacaccaccccgagctttagctttgg cgcgaaaagcgatgaaaacaaagcgggcgcgaccagcaaaccggcgttta gctttggcgcgaaaccggaagaaaaaaaagatgataacagcagcaaaccg gcgtttagctttggcgcgaaaagcaacgaagataaacaggatggcaccgc gaaaccggcgtttagctttggcgcgaaaccggcggaaaaaaacaacaacg aaaccagcaaaccggcgtttagctttggcgcgaaaagcgatgaaaaaaaa gatggcgatgcgagcaaaccggcgtttagctttggcgcgaaaccggatga aaacaaagcgagcgcgaccagcaaaccggcgtttagctttggcgcgaaac cggaagaaaaaaaagatgataacagcagcaaaccggcgtttagctttggc gcgaaaagcaacgaagataaacaggatggcaccgcgaaaccggcgtttag ctttggcgcgaaaccggcggaaaaaaacaacaacgaaaccagcaaaccgg cgtttagctttggcgcgaaaagcgatgaaaaaaagatggcgatgcgagc aaaccggcgtttagctttggcgcgaaaagcgatgaaaaaaagatagcga tagcagcaaaccggcgtttagctttggcaccaaaagcaacgaaaaaaaag atagcggcagcagcaaaccggcgtttagctttggcgcgaaaccggatgaa aaaaaaacgatgaagtgagcaaaccggcgtttagctttggcgcgaaagc gaacgaaaaaaagaaagcgatgaaagcaaaagcgcgtttagctttggca gcaaaccgaccggcaaagaagaaggcgatggcgcgaaagcggcgattagc tttggcgcgaaaccggaagaacagaaaagcagcgataccagcaaaccggc gtttacctttggcaaactggcggcggcgctggaacatcatcatcatcatc at.
```

In one embodiment, the nucleic acid molecule encodes a polypeptide represented by SEQ ID NO:11 (see below). For example, in one embodiment, a DNA sequence encoding SEQ ID NO:11 is:

```
                                            (SEQ ID NO: 23)
atggatattggcattaacagcgatccgggcagcggcagcggcgcgagcg ataacaaaaccaccaacaccaccccgagctttagctttggcgcgaaaag cgatgaaaacaaagcgggcgcgaccagcaaaccggcgtttagctttggc gcgaaaccggaagaaaaaaaagatgataacagcagcaaaccggcgttta gctttggcgcgaaaagcaacgaagataaacaggatggcaccgcgaaacc ggcgtttagctttggcgcgaaaccggcggaaaaaaacaacaacgaaacc agcaaaccggcgtttagctttggcgcgaaaagcgatgaaaaaaagatg gcgatgcgagcaaaccggcgtttagctttggcgcgaaaccggatgaaaa caaagcgagcgcgaccagcaaaccggcgtttagctttggcgcgaaaccg gaagaaaaaaaagatgataacagcagcaaaccggcgtttagctttggcg cgaaaagcaacgaagataaacaggatggcaccgcgaaaccggcgtttag ctttggcgcgaaaccggcggaaaaaaacaacaacgaaaccagcaaaccg
```

-continued

```
gcgtttagattggcgcgaaaagcgatgaaaaaaaagatggcgatgcgag caaaccggcgtttagattggcgcgaaaagcgatgaaaaaaagatagcg atagcagcaaaccggcgtttagattggcaccaaaagcaacgaaaaaaa gatagcggcagcagcaaaccggcgtttagctttggcgcgaaaccggatg aaaaaaaaaacgatgaagtgagcaaaccggcgtttagctttggcgcgaa agcgaacgaaaaaaagaaagcgatgaaagcaaagcgcgtttagcttt ggcagcaaaccgaccggcaaagaagaaggcgatggcgaaagcggcga ttagattggcgcgaaaccggaagaacagaaaagcagcgataccagcaaa ccggcgtttacctttggcaccagcggcagcggcaaactggcggcggcgc tggaacatcatcatcatcatcat.
```

In one embodiment, the nucleic acid molecule encodes a polypeptide represented by SEQ ID NO:12 (see below). For example, in one embodiment, a DNA sequence encoding SEQ ID NO:12 is:

```
                                      (SEQ ID NO: 24)
atggatattggcattaacagcgatccggcgccgcagatgctgcgcgaact gcaggaaaccaacgcggcgctgcaggatgtgcgcgaactgctgcgccagc aggtgaaagaaattacctttctgaaaaacaccgtgatggaaagcgatgcg agcggcgcgagcgcgattagcggcgatagcctgattagcctggcgagcac cggcaaacgcgtgagcattaaagatctgctggatgaaaaagattttgaaa tttggcgattaacgaacagaccatgaaactggaaagcgcgaaagtgagc cgcgtgttttgcaccggcaaaaaactggtgtatattctgaaaacccgcct gggccgcaccattaaagcgaccgcgaaccatcgctttctgaccattgatg gctggaaacgcctggatgaactgagcctgaaagaacatattgcgctgccg cgcaaactggaaagcagcagcctgcagctgagcccggaaattgaaaact gagccagagcgatatttattgggatagcattgtgagcattaccgaaaccg gcgtggaagaagtgtttgatctgaccgtgccgggccgcataactttgtg gcgaacgatattattgtgcataacgcgagcgataacaaaaccaccaacac caccccgagctttagctttggcgcgaaaagcgatgaaaacaaagcgggcg cgaccagcaaaccggcgtttagctttggcgcgaaaccggaagaaaaaaa gatgataacagcagcaaaccggcgtttagctttggcgcgaaaagcaacga agataaacaggatggcaccgcgaaaccggcgtttagctttggcgcgaaac cggcggaaaaaacaacaacgaaaccagcaaaccggcgtttagctttggc gcgaaaagcgatgaaaaaaaagatggcgatgcgagcaaaccggcgtttag ctttggcgcgaaaccggatgaaaacaaagcgagcgcgaccagcaaaccgg cgtttagctttggcgcgaaaccggatgaaaaaaaagatgataacagcagc aaaccggcgtttagctttggcgcgaaaagcaacgaagataaacaggatgg caccgcgaaaccggcgtttagctttggcgcgaaaccggcggaaaaaaaca acaacgaaaccagcaaaccggcgtttagctttggcgcgaaaagcgatgaa aaaaaagatggcgatgcgagcaaaccggcgtttagctttggcgcgaaaag cgatgaaaaaaaagatagcgatagcagcaaaccggcgtttagctttggca
```

-continued

```
ccaaaagcaacgaaaaaaaagatagcggcagcagcaaaccggcgtttagc tttggcgcgaaaccggatgaaaaaaaaacgatgaagtgagcaaaccggc gtttagctttggcgcgaaagcgaacgaaaaaaagaaagcgatgaaagca aaagcgcgtttagctttggcagcaaaccgaccggcaaagaagaaggcgat ggcgcgaaagcggcgattagctttggcgcgaaaccggaagaacagaaaag cagcgataccagcaaaccggcgtttacctttggcaccagcggcagcggca aactggcggcggcgctggaacatcatcatcatcat.
```

In one embodiment, the nucleic acid molecule encodes a polypeptide represented by SEQ ID NO:13 (see below). For example, in one embodiment, a DNA sequence encoding SEQ ID NO:13 is:

```
                                      (SEQ ID NO: 25)
atggatattggcattaacagcgatccgggcagcggcgcgagcccggcgtt tagctttggcgcgaaaccggatgaaaaaaaagatgatgataccagcaaac cggcgtttagctttggcgcgaaaccggatgaaaaaaaagatgatgatacc agcaaaccggcgtttagctttggcgcgaaaccggatgaaaaaaaagatga tgataccagcaaaccggcgtttagctttggcgcgaaaccggatgaaaaaa aagatgatgataccagcaaaccggcgtttagctttggcgcgaaaccggat gaaaaaaaagatgatgataccagcaaaccggcgtttagctttggcgcgaa accggatgaaaaaaaagatgatgataccagcaaaccggcgtttagctttg gcgcgaaaccggatgaaaaaaaagatgatgataccagcaaaccggcgttt agctttggcgcgaaaccggatgaaaaaaaagatgatgataccagcaaaac cagcccggcgtttagctttggcgcgaaaccggatgaaaaaaaagatgatg ataccagcaaaccggcgtttagctttggcgcgaaaccggatgaaaaaaaa gatgatgataccagcaaaccggcgtttagctttggcgcgaaaccggatga aaaaaaagatgatgataccagcaaaccggcgtttagctttggcgcgaaac cggatgaaaaaaaagatgatgataccagcaaaccggcgtttagctttggc gcgaaaccggatgaaaaaaaagatgatgataccagcaaaccggcgtttag ctttggcgcgaaaccggatgaaaaaaaagatgatgataccagcaaaccgg cgtttagctttggcgcgaaaccggatgaaaaaaaagatgatgataccagc aaaccggcgtttagctttggcgcgaaaccggatgaaaaaaaagatgatga taccagcaaaaccagcggcagcggcaaactggcggcggcgctggaacatc atcatcatcat.
```

In one embodiment, the nucleic acid molecule encodes a polypeptide represented by SEQ ID NO:14 (see below). For example, in one embodiment, a DNA sequence encoding SEQ ID NO:14 is:

```
                                      (SEQ ID NO: 26)
atggatattggcattaacagcgatccgggcagcggcgcgagcccggcgtt tagctttggcgcgaaaccggatgaaaaaaaagatagcgataccagcaaac cggcgtttagctttggcgcgaaaccggatgaaaaaaaagatagcgatacc agcaaaccggcgtttagctttggcgcgaaaccggatgaaaaaaaagatag cgataccagcaaaccggcgtttagctttggcgcgaaaccggatgaaaaaa
``` aagatagcgataccagcaaaccggcgtttagctttggcgcgaaaccggat
gaaaaaaaagatagcgataccagcaaaccggcgtttagctttggcgcgaa
accggatgaaaaaaaagatagcgataccagcaaaccggcgtttagctttg
gcgcgaaaccggatgaaaaaaaagatagcgataccagcaaaccggcgttt
agctttggcgcgaaaccggatgaaaaaaaagatagcgataccagcaaaac
cagcccggcgtttagctttggcgcgaaaccggatgaaaaaaaagatagcg
ataccagcaaaccggcgtttagctttggcgcgaaaccggatgaaaaaaaa
gatagcgataccagcaaaccggcgtttagctttggcgcgaaaccggatga
aaaaaaagatagcgataccagcaaaccggcgtttagctttggcgcgaaac
cggatgaaaaaaaagatagcgataccagcaaaccggcgtttagctttggc
gcgaaaccggatgaaaaaaaagatagcgataccagcaaaccggcgtttag
ctttggcgcgaaaccggatgaaaaaaaagatagcgataccagcaaaccgg
cgtttagattggcgcgaaaccggatgaaaaaaaagatagcgataccagca
aaccggcgtttagctttggcgcgaaaccggatgaaaaaaaagatagcgat
accagcaaaaccagcaaaccagcggcagcggcaaactggcggcggcgct
ggaacatcatcatcatcatcat.

In one embodiment, the nucleic acid molecule encodes a polypeptide represented by SEQ ID NO:15 (see below). For example, in one embodiment, a DNA sequence encoding SEQ ID NO:15 is:

(SEQ ID NO: 27)
atggatattggcattaacagcgatccggcgccgcagatgctgcgcgaact
gcaggaaaccaacgcggcgctgcaggatgtgcgcgaactgctgcgccagc
aggtgaaagaaattacctttctgaaaaacaccgtgatggaaagcgatgcg
agcggcgcgagcgataacaaaaccaccaacaccaccccgagctttagctt
tggcgcgaaaagcgatgaaaacaaagcgggcgcgaccagcaaaccggcgt
ttagctttggcgcgaaaccggaagaaaaaaaagatgataacagcagcaaa
ccggcgtttagctttggcgcgaaaagcaacgaagatataaacaggatggcac
cgcgaaaccggcgtttagctttggcgcgaaaccggcggaaaaaaacaaca
acgaaaccagcaaaccggcgtttagctttggcgcgaaaagcgatgaaaaa
aaagatggcgatgcgagcaaaccggcgtttagctttggcgcgaaaaccgga
tgaaaacaaagcgagcgcgaccagcaaaccggcgtttagctttggcgcga
aaccggaagaaaaaaaagatgataacagcagcaaaccggcgtttagattg
gcgcgaaaagcaacgaagatataacaggatggcaccgcgaaaccggcgttt
agctttggcgcgaaaccggcggaaaaaaacaacaacgaaaccagcaaacc
ggcgtttagctttggcgcgaaaagcgatgaaaaaaaagatggcgatgcga
gcaaaccggcgtttagctttggcgcgaaaagcgatgaaaaaaaagatagc
gatagcagcaaaccggcgtttagctttggcaccaaaagcaacgaaaaaaa
agatagcggcagcagcaaaccggcgtttagctttggcgcgaaaccggatg
aaaaaaaaaacgatgaagtgagcaaaccggcgtttagctttggcgcgaaa
gcgaacgaaaaaaaagaaagcgatgaaagcaaaagcgcgtttagctttgg cagcaaaccgaccggcaaagaagaaggcgatggcgcgaaagcggcgatta
gctttggcgcgaaaccggaagaacagaaaagcagcgataccagcaaaccg
gcgtttacctttggcaccagcgcgccgcagatgctgcgcgaactgcagga
aaccaacgcggcgctgcaggatgtgcgcgaactgctgcgccagcaggtga
aagaaattacctttctgaaaaacaccgtgatggaaagcgatgcgagcggc
aaactggcggcggcgctggaacatcatcatcatcatcat.

In one embodiment, the nucleic acid molecule encodes a polypeptide represented by SEQ ID NO:16 (see below). For example, in one embodiment, a DNA sequence encoding SEQ ID NO:16 is:

(SEQ ID NO: 28)
atggatattggcattaacagcgatccggcgccgcagatgctgcgcgaact
gcaggaaaccaacgcggcgctgcaggatgtgcgcgaactgctgcgccagc
aggtgaaagaaattacctttctgaaaaacaccgtgatggaaagcgatgcg
agcggcgcgagcccggcgtttagctttggcgcgaaaccggatgaaaaaaa
agatgatgataccagcaaaccggcgtttagctttggcgcgaaaccggatg
aaaaaaaagatgatgataccagcaaaccggcgtttagctttggcgcgaaa
ccggatgaaaaaaaagatgatgataccagcaaaccggcgtttagctttgg
cgcgaaaccggatgaaaaaaaagatgatgataccagcaaaccggcgttta
gctttggcgcgaaaccggatgaaaaaaaagatgatgataccagcaaaccg
gcgtttagctttggcgcgaaaccggatgaaaaaaaagatgatgataccag
caaaccggcgtttagctttggcgcgaaaccggatgaaaaaaaagatgatg
ataccagcaaaccggcgtttagctttggcgcgaaaccggatgaaaaaaaa
gatgatgataccagcaaaccagcccggcgtttagctttggcgcgaaacc
ggatgaaaaaaaagatgatgataccagcaaaccggcgtttagctttggcg
cgaaaccggatgaaaaaaaagatgatgataccagcaaaccggcgtttagc
tttggcgcgaaaccggatgaaaaaaaagatgatgataccagcaaaccggc
gtttagctttggcgcgaaaccggatgaaaaaaaagatgatgataccagca
aaccggcgtttagctttggcgcgaaaccggatgaaaaaaaagatgatgat
accagcaaaccggcgtttagctttggcgcgaaaccggatgaaaaaaaaga
tgatgataccagcaaaccggcgtttagctttggcgcgaaaccggatgaaa
aaaaagatgatgataccagcaaaccggcgtttagctttggcgcgaaaccg
gatgaaaaaaaagatgatgataccagcaaaccagcgcgccgcagatgct
gcgcgaactgcaggaaaccaacgcggcgctgcaggatgtgcgcgaactgc
tgcgccagcaggtgaaagaaattacctttctgaaaaacaccgtgatggaa
agcgatgcgagcggcggcaaactggcggcggcgctggaacatcatcatca
tcatcat.

In one embodiment, the nucleic acid molecule encodes a polypeptide represented by SEQ ID NO:17 (see below). For example, in one embodiment, a DNA sequence encoding SEQ ID NO:17 is:

(SEQ ID NO: 29)
atggatattggcattaacagcgatccggcgccgcagatgctgcgcgaact gcaggaaaccaacgcggcgctgcaggatgtgcgcgaactgctgcgccagc aggtgaaagaaattacctttctgaaaaacaccgtgatggaaagcgatgcg agcggcgcgagcccggcgtttagctttggcgcgaaaccggatgaaaaaaa agatagcgataccagcaaaccggcgtttagctttggcgcgaaaccggatg aaaaaaagatagcgataccagcaaaccggcgtttagctttggcgcgaaa ccggatgaaaaaaagatagcgataccagcaaaccggcgtttagctttgg cgcgaaaccggatgaaaaaaagatagcgataccagcaaaccggcgttta gctttggcgcgaaaccggatgaaaaaaagatagcgataccagcaaaccg gcgtttagctttggcgcgaaaccggatgaaaaaaagatagcgataccag caaaccggcgtttagctttggcgcgaaaccggatgaaaaaaagatagcg ataccagcaaaccggcgtttagctttggcgcgaaaccggatgaaaaaaa gatagcgataccagcaaaccagcccggcgtttagattggcgcgaaaccg gatgaaaaaaagatagcgataccagcaaaccggcgtttagctttggcgc gaaaccggatgaaaaaaagatagcgataccagcaaaccggcgtttagct ttggcgcgaaaccggatgaaaaaaagatagcgataccagcaaaccggcg tttagattggcgcgaaaccggatgaaaaaaagatagcgataccagcaaa ccggcgtttagctttggcgcgaaaccggatgaaaaaaagatagcgatac cagcaaaccggcgtttagctttggcgcgaaaccggatgaaaaaaagata gcgataccagcaaaccggcgtttagctttggcgcgaaaccggatgaaaa aaagatagcgataccagcaaaccggcgtttagctttggcgcgaaaccgga tgaaaaaaagatagcgataccagcaaaccagcgcgccgcagatgctgc gcgaactgcaggaaaccaacgcggcgctgcaggatgtgcgcgaactgctg cgccagcaggtgaaagaaattacctttctgaaaaacaccgtgatggaag cgatgcgagcggcggcaaactggcggcggcgctggaacatcatcatcatc atcat.

An aspect of the invention is an expression vector comprising a nucleic acid molecule of the invention.

As used herein, the term "vector" refers to a nucleic acid molecule capable of transporting another nucleic acid to which it has been linked. One type of vector is a plasmid, which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including proteins or polypeptides, encoded by nucleic acids as described herein.

The recombinant expression vectors for use in the invention can be designed for expression of a polypeptide of the invention in prokaryotic (e.g., *E. coli*) or eukaryotic cells (e.g., insect cells (using baculovirus expression vectors), yeast cells, or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion E. coli expression vectors include pTrc (Amann et al., 1988, Gene 69:301-315) and pET 11d (Studier et al., p. 60-89, In Gene Expression Technology: Methods in Enzymology vol. 185, Academic Press, San Diego, Calif., 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in E. coli is to express the protein in a host bacterium with an impaired capacity to proteolytically cleave the recombinant protein (Gottesman, p. 119-128, In Gene Expression Technology: Methods in Enzymology vol. 185, Academic Press, San Diego, Calif., 1990). Another strategy is to alter the nucleic acid sequence of the nucleic acid to be inserted into an expression vector so that the individual codons for each amino acid are those preferentially utilized in E. coli (Wada et al., 1992, Nucleic Acids Res. 20:2111-2118). Such alteration of nucleic acid sequences of the invention can be carried out by standard DNA synthesis techniques.

In another embodiment, the expression vector is a yeast expression vector. Examples of vectors for expression in yeast S. cerevisiae include pYepSec1 (Baldari et al., 1987, EMBO J. 6:229-234), pMFa (Kurjan and Herskowitz, 1982, Cell 30:933-943), pJRY88 (Schultz et al., 1987, Gene 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, Mol. Cell Biol. 3:2156-2165) and the pVL series (Lucklow and Summers, 1989, Virology 170:31-39).

In yet another embodiment, a nucleic acid of the invention is expressed in mammalian cells using a mammalian expression vector. Examples of mammalian expression vectors include pCDM8 (Seed, 1987, Nature 329:840) and pMT2PC (Kaufman et al., 1987, EMBO J. 6:187-195). When used in mammalian cells, the expression vector's control functions are often provided by viral regulatory elements. For example, commonly used promoters are derived from polyoma, Adenovirus 2, cytomegalovirus, and Simian Virus 40 (SV40). For other suitable expression systems for both prokaryotic and eukaryotic cells see chapters 16 and 17 of Sambrook et al., ed., Molecular Cloning: A Laboratory Manual, 2nd ed., Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, Genes Dev. 1:268-277), lymphoid-specific promoters (Calame and Eaton, 1988, Adv. Immunol. 43:235-275), in particular promoters of T cell receptors (Winoto and Baltimore, 1989, EMBO J. 8:729-733) and immunoglobulins (Banerji et al., 1983, Cell 33:729-740; Queen and Baltimore, 1983, Cell 33:741-748), neuron-specific promoters (e.g., the neurofilament promoter; Byrne and Ruddle, 1989, Proc. Natl. Acad. Sci. USA 86:5473-5477), pancreas-specific promoters (Edlund et al., 1985, Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, Science 249:374-379) and the α-fetoprotein promoter (Camper and Tilghman, 1989, Genes Dev. 3:537-546).

In certain embodiments, the expression vector is a prokaryotic expression vector.

In certain embodiments, the expression vector is a eukaryotic expression vector.

An aspect of the invention is a cell comprising an expression vector of the invention.

In certain embodiments, the expression vector is a prokaryotic expression vector, and the cell is a prokaryotic cell, e.g., E. coli.

In certain embodiments, the expression vector is a eukaryotic expression vector, and the cell is a eukaryotic cell, e.g., a yeast cell, an insect cell, or a mammalian cell.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

Compositions of the Invention

An aspect of the invention is a hydrogel, comprising a polypeptide of the invention.

An aspect of the invention is a filtering device, comprising a hydrogel of the invention; and a housing or support for the hydrogel. In certain embodiments, the hydrogel is disposed within a housing. In certain embodiments, the hydrogel is disposed within and is in contact with the housing. The housing can be configured in any suitable manner for the intended use of the filtering device, e.g., as a plate, a cone, a manifold, a cartridge, an open-ended tube, a closed-end tube (e.g., a centrifuge tube), etc. The housing optionally can include a fitting, e.g., a screw- or compression-Luer lock fitting, to facilitate connection of the filtering device to a fluid path. In certain embodiments, the hydrogel is disposed upon a support. In certain embodiments, the hydrogel is disposed upon and is in contact with the support. The support can be configured in any suitable manner for the intended use of the filtering device, e.g., as a frame, a perforated plate, a mesh, a fabric, a filter, etc.

In certain embodiments, the support, together with the hydrogel, can be fitted or placed into a housing which is configured and arranged to receive the support.

An aspect of the invention is a drug delivery device, comprising a drug; and a hydrogel of the invention.

In certain embodiments, the drug is a macromolecule.
In certain embodiments, the drug is a nucleic acid.
In certain embodiments, the drug is an RNA.
In certain embodiments, the drug is a DNA.
In certain embodiments, the drug is a polymer.
In certain embodiments, the drug is a polypeptide.
In certain embodiments, the drug is a protein.
In certain embodiments, the drug is a fusion protein.
In certain embodiments, the drug is an antibody or an antigen-binding fragment of an antibody.
In certain embodiments, the drug is a cytokine.
In certain embodiments, the drug is a glycoprotein.
In certain embodiments, the drug is a carbohydrate.
In certain embodiments, the drug is a lipid.
In certain embodiments, the drug is a toxin.
In certain embodiments, the drug is a steroid.
In certain embodiments, the drug is a hormone, e.g., an estrogen or a progestogen.
In certain embodiments, the drug is dispersed within the hydrogel.

In certain embodiments, the drug is effectively enveloped by the hydrogel. For example, the drug can be enclosed within a housing, wherein at least a portion of the housing is open to the environment but for the presence of the hydrogel.

In certain embodiments, the drug is enveloped by the hydrogel. For example, the drug can be present as a core which is completely surrounded by the hydrogel; the core can include more than a single active agent, and there can be one or more additional layers present between the drug or core and the hydrogel. In certain embodiments, there can be one or more additional layers external to the hydrogel.

Methods of the Invention

An aspect of the invention is a method of separating or selectively filtering macromolecules, comprising contacting a source of macromolecules with a hydrogel of the invention. For example, a solution comprising a macromolecule can be contacted with a hydrogel of the invention.

As used herein, the term "macromolecule" refers to any molecule having a molecular weight greater than about 1500 Da. In certain embodiments, a macromolecule has a molecular weight greater than or equal to about 10,000 Da. In certain embodiments, a macromolecule has a molecular weight greater than or equal to about 20,000 Da. In certain embodiments, a macromolecule has a molecular weight greater than or equal to about 30,000 Da. In certain embodiments, a macromolecule has a molecular weight greater than or equal to about 40,000 Da. In certain embodiments, a macromolecule has a molecular weight greater than or equal to about 50,000 Da. In certain embodiments, a macromolecule has a molecular weight greater than or equal to about 60,000 Da. In certain embodiments, a macromolecule has a molecular weight greater than or equal to about 70,000 Da. In certain embodiments, a macromolecule has a molecular weight greater than or equal to about 80,000 Da. In certain embodiments, a macromolecule has a molecular weight greater than or equal to about 90,000 Da. In certain embodiments, a macromolecule has a molecular weight greater than or equal to about 100,000 Da.

In certain embodiments, the macromolecule is a naturally occurring macromolecule. In certain embodiments, the macromolecule is a synthetic or semi-synthetic macromolecule. In certain embodiments, the macromolecule is present as part of a complex or conjugate with another molecule, e.g., a karyopherin.

In certain embodiments, the macromolecule is selected from the group consisting of RNA, mRNA, DNA, proteins, glycoproteins, carbohydrates, lipids, toxins, and any combination thereof.

In certain embodiments, the macromolecule is RNA.
In certain embodiments, the macromolecule is mRNA.
In certain embodiments, the macromolecule is DNA.
In certain embodiments, the macromolecule is a protein.
In certain embodiments, the macromolecule is a glycoprotein.
In certain embodiments, the macromolecule is a carbohydrate.
In certain embodiments, the macromolecule is a lipid.
In certain embodiments, the macromolecule is a toxin.

Having described the present invention in detail, the same will be more clearly understood by reference to the following examples, which are included herewith for purposes of illustration only and are not intended to be limiting of the invention.

EXAMPLES

Materials and Methods

DNA engineering:

The $Nsp1^{30-591}$ gene from the Chait group was amplified by polymerase chain reaction (PCR) to prepare BamHI (B)-NheI (N)-$Nsp1^{30-591}$-SpeI (S)-HindIII (H) and B-N-cNsp1 ($Nsp1^{282-585}$)-S-H. Then, both DNA fragments were subcloned into the pET22b expression plasmid (C-terminal 6×His tag (SEQ ID NO: 30)) using BamHI and HindIII restriction sites. The pET22b vector was chosen due to the C-terminal 6×His tag (SEQ ID NO: 30) which allows isolation of full length proteins by metal affinity chromatography. B-N-1NLP-S-H, B-N-2NLP-S-H, B-P-EcoRI-intein-N-cNsp1-S-H, B-P domain (P)-N-cNsp1-S-P-H, B-P-N-1NLP-S-P-H and B-P-N-2NLP-S-P-H were also prepared. Gene sequences of B-P domain (P)-N-1NLP$_{1/2}$-S-P-H and B-P-N-2NLP$_{1/2}$-S-P-H were purchased (GenScript, USA) and subcloned into the pET22b expression plasmid using BamHI and HindIII restriction sites. To prepare P-1NLP-P and P-2NLP-P, N-1NLP$_{1/2}$-S and N-2NLP$_{1/2}$-S were subcloned into pET22b-B-P-N-1NLP$_{1/2}$-S—P-H and pET22b-B-P-N-2NLP$_{1/2}$-S-P-H plasmids using the SpeI restriction enzyme site. P-cNsp1-P was prepared by subcloning N-cNsp1-S into the pET22b-B-P-N-1NLP$_{1/2}$-S-P-H plasmid using NheI and SpeI restriction sites. 1NLP and 2NLP were prepared by subcloning N-1NLP-S and N-2NLP-S from pET22b-B-P-N-1NLP-S-P-H and pET22b-B-P-N-2NLP-S-P-H plasmids into pET22b-B-P-N-1NLP$_{1/2}$-S-P-H and pET22b-B-P-N-2NLP$_{1/2}$-S-P-H plasmids using NheI and SpeI restriction enzyme sites. B-P-EcoRI-intein-N sequences were purchased (Integrated DNA Technologies, USA) and subcloned into the pET22b-B-N-cNsp1-S-H plasmid using BamHI and NheI restriction enzyme sites. Sequences of all plasmids were confirmed by gene sequencing (Genewiz, USA). Prepared protein sequences are as follows.

$Nsp1^{30-591}$ (SEQ ID NO: 10)
MDIGINSDPSTGAGAFGTGQSTFGFNNSAPNNTNNANSSITPAFGSNNTG

NTAFGNSNPTSNVFGSNNSTTNTFGSNSAGTSLFGSSSAQQTKSNGTAGG

NTFGSSSLFNNSTNSNTTKPAFGGLNFGGGNNTTPSSTGNANTSNNLFGA

-continued

```
TANANKPAFSFGATTNDDKKTEPDKPAFSFNSSVGNKTDAQAPTTGFSFG

SQLGGNKTVNEAAKPSLSFGSGSAGANPAGASQPEPTTNEPAKPALSFGT

ATSDNKTTNTTPSFSFGAKSDENKAGATSKPAFSFGAKPEEKKDDNSSKP

AFSFGAKSNEDKQDGTAKPAFSFGAKPAEKNNNETSKPAFSFGAKSDEKK

DGDASKPAFSFGAKPDENKASATSKPAFSFGAKPEEKKDDNSSKPAFSFG

AKSNEDKQDGTAKPAFSFGAKPAEKNNNETSKPAFSFGAKSDEKKDGDAS

KPAFSFGAKSDEKKDSDSSKPAFSFGTKSNEKKDSGSSKPAFSFGAKPDE

KKNDEVSKPAFSFGAKANEKKESDESKSAFSFGSKPTGKEEGDGAKAAIS

FGAKPEEQKSSDTSKPAFTFGKLAAALEHHHHHH
``` cNsp1
(SEQ ID NO: 11)
```
MDIGINSDPGSGSGASDNKTTNTTPSFSFGAKSDENKAGATSKPAFSFGA

KPEEKKDDNSSKPAFSFGAKSNEDKQDGTAKPAFSFGAKPAEKNNNETSK

PAFSFGAKSDEKKDGDASKPAFSFGAKPDENKASATSKPAFSFGAKPEEK

KDDNSSKPAFSFGAKSNEDKQDGTAKPAFSFGAKPAEKNNNETSKPAFSF

GAKSDEKKDGDASKPAFSFGAKSDEKKDSDSSKPAFSFGTKSNEKKDSGS

SKPAFSFGAKPDEKKNDEVSKPAFSFGAKANEKKESDESKSAFSFGSKPT

GKEEGDGAKAAISFGAKPEEQKSSDTSKPAFTFGTSGSGKLAAALEHHHH

HH
```

P-Intein-cNsp1
(SEQ ID NO: 12)
```
MDIGINSDPAPQMLRELQETNAALQDVRELLRQQVKEITFLKNTVMESDA

SGASAISGDSLISLASTGKRVSIKDLLDEKDFEIWAINEQTMKLESAKVS

RVFCTGKKLVYILKTRLGRTIKATANHRFLTIDGWKRLDELSLKEHIALP

RKLESSSLQLSPEIEKLSQSDIYWDSIVSITETGVEEVFDLTVPGPHNFV

ANDIIVHNASDNKTTNTTPSFSFGAKSDENKAGATSKPAFSFGAKPEEKK

DDNSSKPAFSFGAKSNEDKQDGTAKPAFSFGAKPAEKNNNETSKPAFSFG

AKSDEKKDGDASKPAFSFGAKPDENKASATSKPAFSFGAKPEEKKDDNSS

KPAFSFGAKSNEDKQDGTAKPAFSFGAKPAEKNNNETSKPAFSFGAKSDE

KKDGDASKPAFSFGAKSDEKKDSDSSKPAFSFGTKSNEKKDSGSSKPAFS

FGAKPDEKKNDEVSKPAFSFGAKANEKKESDESKSAFSFGSKPTGKEEGD

GAKAAISFGAKPEEQKSSDTSKPAFTFGTSGSGKLAAALEHHHHHH
```

1NLP
(SEQ ID NO: 13)
```
MDIGINSDPGSGASPAFSFGAKPDEKKDDDTSKPAFSFGAKPDEKKDDDT

SKPAFSFGAKPDEKKDDDTSKPAFSFGAKPDEKKDDDTSKPAFSFGAKPD

EKKDDDTSKPAFSFGAKPDEKKDDDTSKPAFSFGAKPDEKKDDDTSKPAF

SFGAKPDEKKDDDTSKTSPAFSFGAKPDEKKDDDTSKPAFSFGAKPDEKK

DDDTSKPAFSFGAKPDEKKDDDTSKPAFSFGAKPDEKKDDDTSKPAFSFG

AKPDEKKDDDTSKPAFSFGAKPDEKKDDDTSKPAFSFGAKPDEKKDDDTS

KPAFSFGAKPDEKKDDDTSKTSGSGKLAAALEHHHHHH
```

2NLP
(SEQ ID NO: 14)
```
MDIGINSDPGSGASPAFSFGAKPDEKKDSDTSKPAFSFGAKPDEKKDSDT

SKPAFSFGAKPDEKKDSDTSKPAFSFGAKPDEKKDSDTSKPAFSFGAKPD

EKKDSDTSKPAFSFGAKPDEKKDSDTSKPAFSFGAKPDEKKDSDTSKPAF

SFGAKPDEKKDSDTSKTSPAFSFGAKPDEKKDSDTSKPAFSFGAKPDEKK

DSDTSKPAFSFGAKPDEKKDSDTSKPAFSFGAKPDEKKDSDTSKPAFSFG

AKPDEKKDSDTSKPAFSFGAKPDEKKDSDTSKPAFSFGAKPDEKKDSDTS

KPAFSFGAKPDEKKDSDTSKTSKTSGSGKLAAALEHHHHHH
```

P-cNsp1-P
(SEQ ID NO: 15)
```
MDIGINSDPAPQMLRELQETNAALQDVRELLRQQVKEITFLKNTVMESDA

SGASDNKTTNTTPSFSFGAKSDENKAGATSKPAFSFGAKPEEKKDDNSSK

PAFSFGAKSNEDKQDGTAKPAFSFGAKPAEKNNNETSKPAFSFGAKSDEK

KDGDASKPAFSFGAKPDENKASATSKPAFSFGAKPEEKKDDNSSKPAFSF

GAKSNEDKQDGTAKPAFSFGAKPAEKNNNETSKPAFSFGAKSDEKKDGDA

SKPAFSFGAKSDEKKDSDSSKPAFSFGTKSNEKKDSGSSKPAFSFGAKPD

EKKNDEVSKPAFSFGAKANEKKESDESKSAFSFGSKPTGKEEGDGAKAAI

SFGAKPEEQKSSDTSKPAFTFGTSAPQMLRELQETNAALQDVRELLRQQV

KEITFLKNTVMESDASGKLAAALEHHHHHH
```

P-1NLP-P
(SEQ ID NO: 16)
```
MDIGINSDPAPQMLRELQETNAALQDVRELLRQQVKEITFLKNTVMESDA

SGASPAFSFGAKPDEKKDDDTSKPAFSFGAKPDEKKDDDTSKPAFSFGAK

PDEKKDDDTSKPAFSFGAKPDEKKDDDTSKPAFSFGAKPDEKKDDDTSKP

AFSFGAKPDEKKDDDTSKPAFSFGAKPDEKKDDDTSKPAFSFGAKPDEKK

DDDTSKTSPAFSFGAKPDEKKDDDTSKPAFSFGAKPDEKKDDDTSKPAFS

FGAKPDEKKDDDTSKPAFSFGAKPDEKKDDDTSKPAFSFGAKPDEKKDDD

TSKPAFSFGAKPDEKKDDDTSKPAFSFGAKPDEKKDDDTSKPAFSFGAKP

DEKKDDDTSKTSAPQMLRELQETNAALQDVRELLRQQVKEITFLKNTVME

SDASGGKLAAALEHHHHHH
```

P-2NLP-P
(SEQ ID NO: 17)
```
MDIGINSDPAPQMLRELQETNAALQDVRELLRQQVKEITFLKNTVMESDA

SGASPAFSFGAKPDEKKDSDTSKPAFSFGAKPDEKKDSDTSKPAFSFGAK

PDEKKDSDTSKPAFSFGAKPDEKKDSDTSKPAFSFGAKPDEKKDSDTSKP

AFSFGAKPDEKKDSDTSKPAFSFGAKPDEKKDSDTSKPAFSFGAKPDEKK

DSDTSKTSPAFSFGAKPDEKKDSDTSKPAFSFGAKPDEKKDSDTSKPAFS

FGAKPDEKKDSDTSKPAFSFGAKPDEKKDSDTSKPAFSFGAKPDEKKDSD

TSKPAFSFGAKPDEKKDSDTSKPAFSFGAKPDEKKDSDTSKPAFSFGAKP

DEKKDSDTSKTSAPQMLRELQETNAALQDVRELLRQQVKEITFLKNTVME

SDASGGKLAAALEHHHHHH
```

Figure 2A:
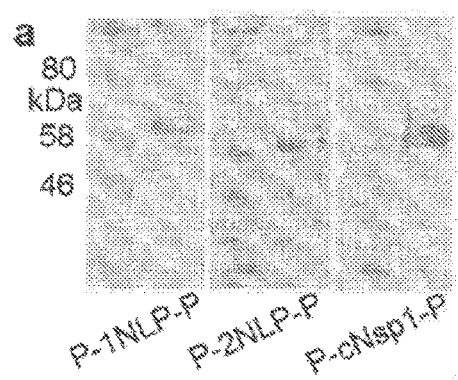
FIG. 2A depicts a series of three western blots SDS-PAGE of indicated lyophilized protein samples.
Figure 2B:
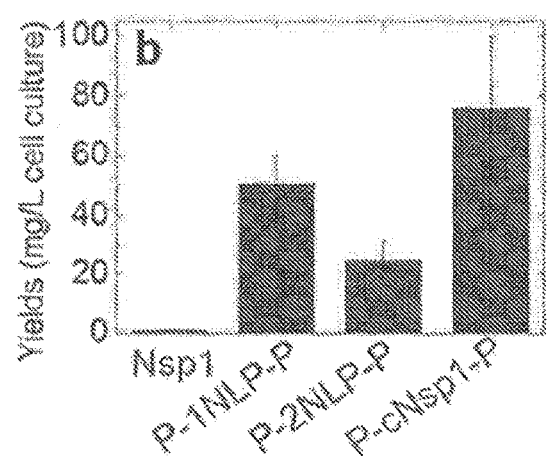
FIG. 2B is a graph depicting yields of designed proteins flanked by P domains.
Figure 3A:
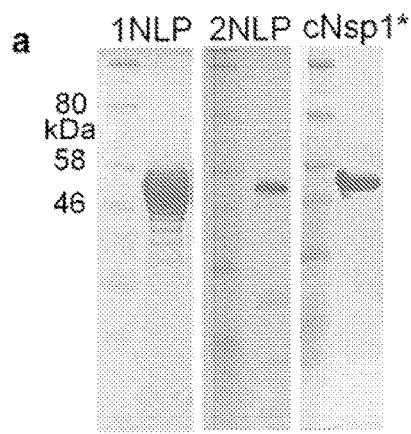
FIG. 3A is a panel of three western blots depicting expression levels of 1NLP, 2NLP, and cNsp1*, where cNsp1* was obtained as a product from P-intein-cNsp1.
Figure 3B:
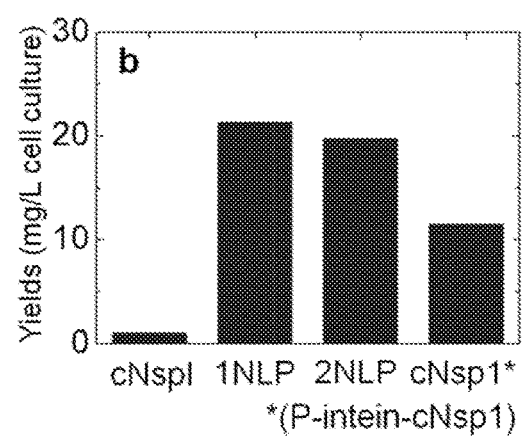
FIG. 3B is a bar graph depicting expression levels of cNsp1, 1NLP, 2NLP, and cNsp1*, where cNsp1* was obtained as a product from P-intein-cNsp1.

Protein Expression and Purification:

All prepared genes were transformed into *E. coli* OverExpress C41(DE3) cells (Lucigen, USA). For expression, a freshly-grown bacterial colony was inoculated in 10 mL LB medium with 100 µg/mL ampicillin at 37° C. overnight. 10 mL of overnight culture of all samples was inoculated into 1 L terrific broth (TB) media at 37° C. with 100 µg/mL ampicillin until $OD_{600}$~1. Expression was then induced overnight at room temperature with the addition of 1 mM IPTG. The cells were harvested, lysed in 50 mM Tris (pH 8), 300 mM NaCl and 8 M urea, and frozen at −80° C. Thawed cells were sonicated, and 15 w/v % ammonium sulfate was added. Cell lysates were clarified by centrifugation (14,000 g for 30 min at 4° C.), and the proteins of interest were purified by Ni-NTA affinity chromatography under denaturing conditions with 250 mM imidazole used for protein elution. Purified samples were dialyzed against deionized (DI) water, and 20 mM Tris (pH 8) and 6 M urea were added. The proteins were further purified by ion exchange chromatography using a HiTrap Q HP column (GE Healthcare, Sweden) in an ÄKTA pure FPLC. Samples containing the desired product were dialyzed against DI water and lyophilized. P-intein-cNsp1 was prepared using the same expression condition as the other proteins, but harvested cells were resuspended in 50 mM $NaH_2PO_4$, 300 mM NaCl, and 10 mM imidazole and stored at −80° C. Thawed cells were lysed by the sonication, and cell lysates clarified by centrifugation were stored overnight at 4° C. at pH 7 for intein self-cleavage. Sun Z et al., *Protein Expr Purif* 43: 26 (2005). After adjusting the pH to 8, samples with 6×His tags (SEQ ID NO: 30) were purified by Ni-NTA under native conditions and by FPLC as described above. P-$C_{30}$-P protein was expressed and purified as reported previously (Olsen B D et al., *Macromolecules* 43: 9094 (2010)), with additional FPLC purification under denaturing conditions. Lyophilized samples were weighed to calculate yields of samples from 1 L culture (FIG. 2B and FIG. 3B). The purity of samples was determined to be greater than 95% by SDS-PAGE analysis (FIG. 2A and FIG. 3A).

For transport studies, pQE80-14×His tag-TEV-IBB-MBP-EGFP, pQE80-14×His tag-TEV-MBP-mCherry and pQE30-scImp β-6×His tag from the Görlich group were transformed into SG13009 (pRep4) cells, and expression followed a previously described protocol. Frey S et al., *EMBO J* 28: 2554 (2009). After cutting off the His-tag with TEV protease (Eton Bioscience, USA) for IBB-MBP-EGFP and MBP-mCherry, additional purification was performed for all three proteins by size exclusion chromatography in buffer containing 50 mM Tris (pH 7.5) and 200 mM NaCl. The concentration of recombinant fluorescent proteins was determined using their optical absorbance.

FITC-Dextran:

Fluorescein isothiocyanate (FITC)-dextran with molar masses of 4, 10, 40, 70 and 150 kg/mol (catalog #46994, FD10S, FD40, 46945 and 46946), were purchased from Sigma-Aldrich (USA). Approximate Stokes' radii of the FITC-dextran polymers were obtained from the supplier as follows: 1.4 nm (4 kg/mol), 2.3 nm (10 kg/mol), 4.5 nm (40 kg/mol), 6.0 nm (70 kg/mol) and 8.5 nm (150 kg/mol).

Figure 4:
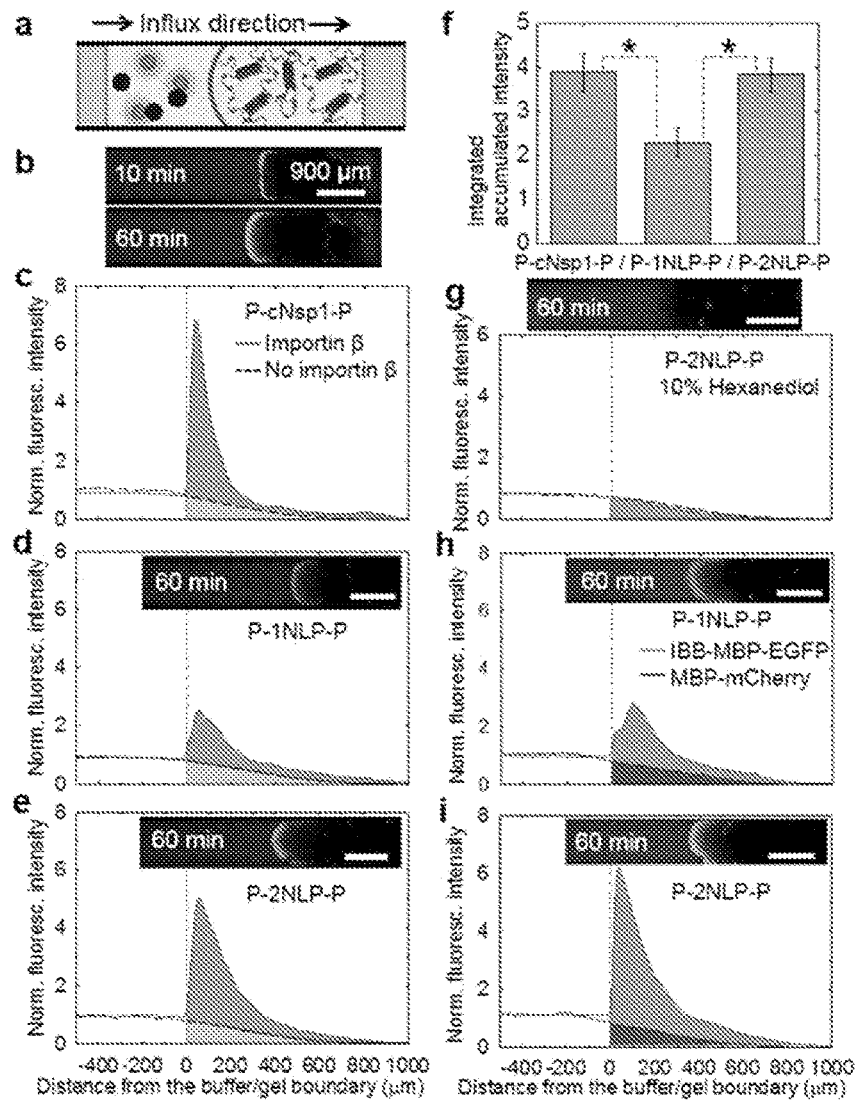
FIG. 4A depicts a schematic of capillary transport assay set-up. Blue (darker) and green (lighter) circles represent importin β and IBB-MBP-EGFP, respectively.
FIG. 4B depicts a time course transport measurement of 20 w/v % P-cNsp1-P hydrogel with β.
FIG. 4C is a graph depicting 20 w/v % P-cNsp1-P hydrogels in the presence (solid line) or absence (dotted line) of importin β.
FIG. 4D is a graph depicting 20 w/v % P-1NLP-P hydrogels in the presence (solid line) or absence (dotted line) of importin β. Scale bar, 900 μm.
FIG. 4E is a graph depicting 20 w/v % P-2NLP-P hydrogels in the presence (solid line) or absence (dotted line) of importin β. Scale bar, 900 μm.
FIG. 4F is a graph depicting absorption of cargo-importin β complexes by P-cNsp1-P, P-1NLP-P and P-2NLP-P hydrogels in one hour. * denotes $p<0.05$.
FIG. 4G is a graph depicting fluorescence intensity measurements on P-2NLP-P hydrogels (20 w/v %) with 10% 1,6 hexanediol. Scale bar, 900 μm.
FIG. 4H is a graph depicting selective permeability test performed on P-1NLP-P biosynthetic hydrogels (20 w/v %) with the addition of 5 μM MBP-mCherry, a model inert molecule, into 5 μM IBB-MBP-EGFP/importin β cargo complex mixtures. Scale bar, 900 μm.
FIG. 4I is a graph depicting selective permeability test performed on P-2NLP-P biosynthetic hydrogels (20 w/v %) with the addition of 5 μM MBP-mCherry, a model inert molecule, into 5 μM IBB-MBP-EGFP/importin β cargo complex mixtures. Scale bar, 900 μm.

Hydrogel Preparation:

Lyophilized samples were dissolved at a concentration of 200 mg/mL in 50 mM Tris/HCl (pH 7.5) and 200 mM NaCl except where otherwise noted, mixed, and allowed to gel at either room temperature or 4° C. It is known that natural nucleoporins can form homogeneous hydrogels at such high protein concentration, but at lower nucleoporin concentrations, the hydrogels lose their selective permeability function. For this reason, nucleoporin hydrogels, Nsp1, are typically prepared at 150-200 mg/mL concentration throughout the literature. Since the invention concerns developing artificially engineered protein hydrogels that mimic the function of natural nucleoporin hydrogels, the nucleoporin hydrogels were benchmarked to these previous studies and used the concentration where it showed the selective transport property. Having confirmed that the designed hydrogels at 20 w/v % can show selectivity (FIG. 4 and FIG. 5), the ability of the best performing gel, P-2NLP-P, to mimic this property at a lower gel concentration, 10 w/v % (FIG. 5), was checked. During the hydrogel inversion test, food coloring was added in the buffer for better visualization of the test.

Rheology:

Oscillatory shear rheology was performed on an Anton Paar MCR-301 in Direct Strain Oscillation mode with TruGap™ control. A Peltier heating system and environmental enclosure were employed to control sample temperature. Samples were loaded into a 25 mm cone-and-plate geometry with an angle of 1° and sealed with a mineral oil barrier to prevent dehydration.

Raman Spectroscopy:

A custom-built NIR confocal Raman inverted microscopy system was used for Raman measurements. 785 nm light from a continuous-wave Ti:Sapphire laser (3900S, Spectra-Physics) pumped by a frequency-doubled Nd:YAG laser (Millennia 5sJ, Spectra-Physics) was used for the excitation. A water immersion objective lens with 1.2 NA (UPLSAPO60XWIR 60×/1.20, Olympus) was used both to focus the laser onto the sample, which is on top of quartz coverslip (043210-KJ, Alfa Aesar), and to collect the back-scattered light. The Rayleigh light in the collected signal was removed by dichroic mirrors (LPD01-785RU-25×36×1.1, Semrock). Raman light was delivered to an imaging spectrograph (Holospec f/1.8i, Kaiser Optical Systems) and detected by a TE-cooled, back-illuminated, deep depleted CCD (PIXIS: 100BR_eXcelon, Princeton Instruments). The laser power at the sample plane was ca. 60 mW, and the signal was integrated for 5 seconds. Nine spectra were collected from each sample and averaged. Spectrum processing (cosmic ray removal, background subtraction and normalization) was performed by MATLAB (Mathworks) scripts.

Capillary Transport Measurements:

1.5 inch borosilicate capillaries with 0.9 mm inner diameters (Vitrocom 8290) were loaded by piercing pre-made hydrogels. 5 µM solutions of IBB-MBP-EGFP, MBP-mCherry, and/or importin β were injected into the capillary and sealed by a 1:1:1 mixture of vaseline, lanolin, and paraffin. Time lapses of cargo transport into the hydrogels were taken at 1 minute intervals for 1-3 hours on a Nikon Ti Eclipse inverted microscope using a Nikon CFI Plan UW 2× and Hamamatsu C11440-22CU camera. All fluorescence intensity profiles were obtained by averaging the fluorescence intensity within 100 µm slice width through the center of the gel and across the gel/buffer interface. The profiles were normalized by the bath concentration in the capillaries at the first time point. The interface between gel and buffer is assigned by a 20% change in the intensity compared to the bath fluorescence intensity as the zero point of the distance scale in each fluorescence intensity profile.

Circular Dichroism Spectroscopy:

CD spectra were obtained on an Aviv Model 202 Circular Dichroism spectrometer. CD spectra were recorded in a quartz cell of 0.1 cm path length at 25° C. between 190 and 250 nm, using a scan rate of 12 nm/min with a wavelength step of 1 nm. cNsp1 and the NLPs were dissolved in 50 mM Tris buffer with 200 mM NaCl at pH 7.5. CD band intensities, after the buffer signal subtractions, were converted into mean residue ellipticity (MRE).

Example 1: Preparation and Expression of Engineered Proteins

Figure 6:
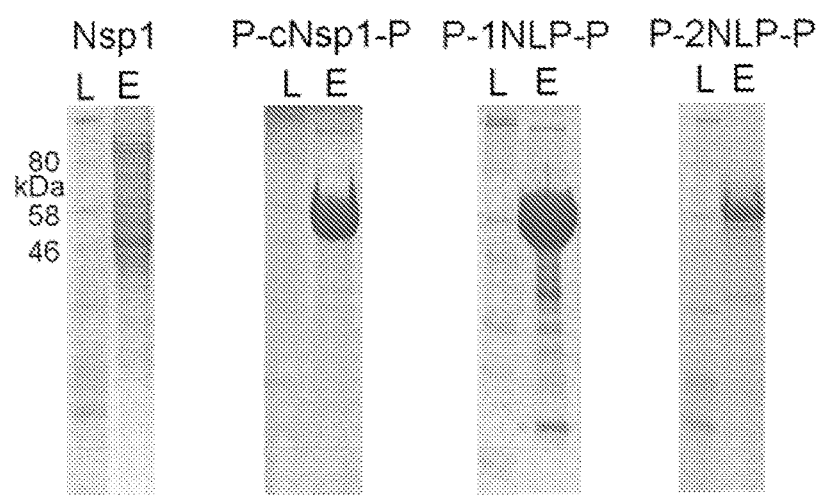
FIG. 6 is a panel of four western blots depicting protein expression levels of Nsp1, P-cNsp1-P, P-1NLP-P, and P-2NLP-P. L, protein ladder; E, elution fraction.

To reduce protein loss during washing step in Ni-NTA chromatography denaturing purification, the washing buffer did not contain imidazole and was prepared at pH 8, causing increased impurity during elution. After the elution, eluted proteins were run on denaturing gels (FIG. 6). While Nsp1 (60 kg/mol), one of nuclear pore proteins, was expressed at low levels and difficult to identify on the gel, engineered proteins (P-cNsp1-P and P-NLPs-P) were highly expressed. For better purity, anion exchange chromatography was performed, with final purified products shown in FIG. 2A. Note that all proteins ran slower in SDS-PAGE (FIGS. 2A, 7A, and 6) than their calculated and measured molar masses (Table 1), similar to previous reports for P-$C_{30}$-P protein. Olsen B D et al., *Macromolecules* 43: 9094 (2010).

TABLE 1

Protein molar masses measured by MALDI

|  | cNsp1 | 1NLP | 2NLP | P-cNsp1-P | P-1NLP-P | P-2NLP-P |
|---|---|---|---|---|---|---|
| Measured (g/mol) | 35,623 | 36,756 | 36,223 | 46,305 | 46,331 | 45,780 |
| Calculated (g/mol) | 35,460 | 36,461 | 36,329 | 45,971 | 45,885 | 45,437 |

TABLE 2

DNA plasmids

| Protein name | Expressed protein | Vector |
|---|---|---|
| Nsp1$^{30-591}$ | Nsp1-His$_6$ | pET-22b |
| cNsp1(=Nsp1$^{274-591}$) | cNsp1-His$_6$ | pET-22b |
| cNsp1 | P-Intein-cNsp1-His$_6$ | pET-22b |
| 1NLP | 1NLP-His$_6$ | pET-22b |
| 2NLP | 2NLP-His$_6$ | pET-22b |
| P-cNsp1-P | P-cNsp1-P-His$_6$ | pET-22b |
| P-1NLP-P | P-1NLP-P-His$_6$ | pET-22b |
| P-2NLP-P | P-2NLP-P-His$_6$ | pET-22b |
| P-$C_{30}$-P | His$_6$-P-$C_{30}$-P | pQE-9 |
| IBB-MBP-EGFP | His$_{14}$-TEV-IBB-MBP-mEGFP | pQE-80 |
| MBP-mCherry | His$_{14}$-TEV-MBP-mCherry | pQE-80 |
| scImpβ | scImpβ-His$_6$ | pQE-30 |

Engineered proteins with P domain blocks—P-cNsp1-P, P-1NLP-P and P-2NLP-P—were easily synthesized in much higher yield than recombinant nucleoporin Nsp1. After protein expression and chromatographic purification, the yield of high purity protein was more than 20- to 70-fold higher than the recombinant Nsp1 protein (FIG. 2 and FIG. 6).

NLPs without the coiled-coil domain were also isolated at 10 times greater yield than their parent sequence, cNsp1, after the same procedure (FIG. 3). Interestingly, when the cNsp1 was fused to the P domain endblocks (P-cNsp1-P), the construct was expressed at a similar yield as the NLP constructs.

Based on this observation, a single P domain together with an intein self-cleavage domain (Mathys S et al., *Gene* 231: 1 (1999)) was subcloned into the N-terminal cNsp1 gene (P-intein-cNsp1). After the self-cleavage of P-intein domains, cNsp1 was obtained at a similar yield as the NLPs (FIG. 3). Significantly improved biosynthetic yields of these artificially engineered proteins enable detailed characterization of their material properties and engineering to control their performance.

Example 2: Preparation and Characterization of Hydrogels

Engineered proteins with P domain endblocks rapidly formed hydrogels, while NLP midblocks alone failed inversion tests, indicating that structure beyond the FG repeat is necessary to give elastic mechanical properties. Consistent with a previous study on recombinant cNsp1, the NLPs without associating coiled-coil domains did not pass hydrogel inversion tests, while the designed proteins with the P domains formed hydrogels within a few minutes, mainly limited by the time required for the lyophilized sample to swell in a buffer. The engineered proteins were found to gel in number of buffer conditions commonly used for the recombinant Nsp1, demonstrating that P domain endblocks successfully replace the role of the N-terminal sequences of Nsp1 as a gel crosslinker.

More particularly, while cNsp1 is known not to form hydrogels, P-cNsp1-P formed gels in all commonly used buffer conditions for Nsp1 at a protein concentration of 200 mg/mL. Buffers tested included (i) water; (ii) 0.1% TFA (in water), followed by neutralization with ¼ volume of the buffer (400 mM Tris-base, 100 mM Tris/HCl pH 7.5, 1 M NaCl); (iii) 0.1% TFA (in water) and neutralized with ⅕ volume of 200 mM Tris-HCl (pH 8.5); (iv) 0.2% TFA (in water) and neutralized with ⅕ volume of 200 mM Tris-HCl (pH 9); and (v) 100 mM phosphate buffer.

Example 3: Significance of Midblock FG Repeats

Figure 8:
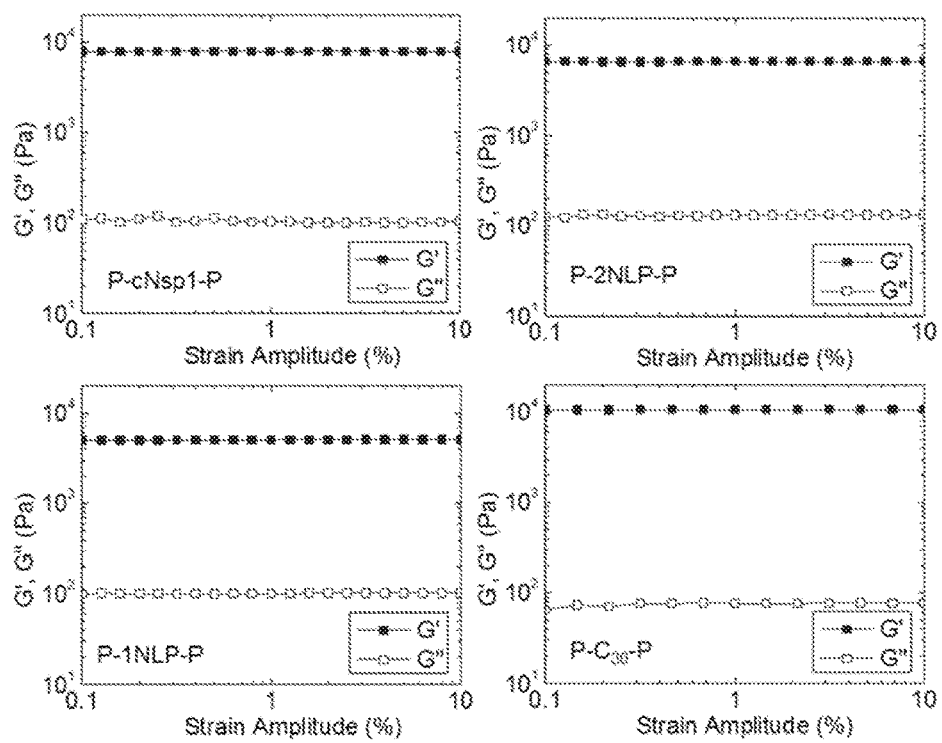
FIG. 8 is a series of four graphs depicting strain sweep oscillatory shear rheology of indicated 20 w/v % hydrogels at 100 rad/s and 25° C. C is a peptide having amino acid sequence AGAGAGPEG (SEQ ID NO:8).

To characterize the effect of midblock interactions on hydrogel mechanics, frequency sweep, linear oscillatory shear rheology of 20 w/v % hydrogels was performed in the absence or presence of 10% 1,6 hexanediol. Measurements were performed at 25° C. with a strain amplitude of 1%, within the linear viscoelastic range. Representative results are shown in FIG. 8.

Rheology showed that the midblock sequence has a significant impact on the low frequency viscoelastic properties of the triblock protein gels without affecting the high frequency elastic plateau modulus. Although the midblocks cNsp1, 1NLP, and 2NLP are insufficient to cause gelation without the P domain, all three proteins with P domains formed gels with a comparable modulus (on the order of 10 kPa) with the crossover between G' and G" occurring below 0.1 rad/s (FIG. 7A-C). In all three artificially engineered hydrogels, the addition of 10% hexanediol to a 20 w/v % gel led to a decrease in the gel relaxation time, increasing the crossover frequency of the gel by approximately a factor of 5, while the stiffness of hydrogels (the plateau modulus G') changed very little (FIG. 7A-C).

Figure 9A:
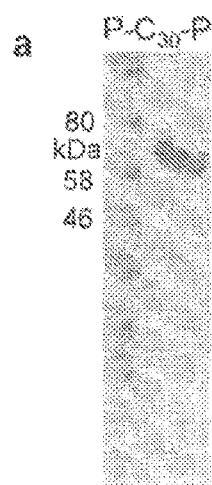
FIG. 9A is a western blot depicting P-C$_{30}$-P. C is a peptide having amino acid sequence AGAGAGPEG (SEQ ID NO:8).
Figure 9B:
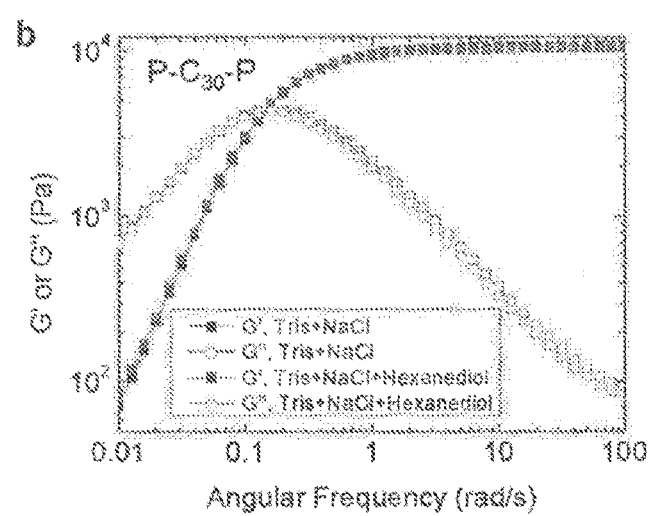
FIG. 9B is a graph depicting strain sweep oscillatory shear rheology of indicated P-C$_{30}$-P hydrogels prepared by hydrating lyophilized samples (20 w/v %) with buffer containing 50 mM Tris/HCl (pH 7.5) and 200 mM NaCl in the presence or absence of 10% 1,6-hexanediol.

Aliphatic alcohols, such as 1,6 hexanediol, are known to weaken FG associations, leading to a loss of selective permeability in vivo and in vitro. Comparison to a control hydrogel of similar molar mass but without FG repeats in the midblock (P-$C_{30}$-P) showed no effect on the crossover frequency and the high frequency plateau modulus after the addition of hexanediol (FIG. 7D and FIG. 9), indicating that the endblock P domains are unaffected by hexanediol. Therefore, the changes in crossover frequency in nucleoporin-mimetic gels, characteristic of changes in network relaxation rate, originate from differences in the state of the midblock domain.

It has been shown that interchain β-sheets in some nucleoporin FG repeat hydrogels contribute to crosslinking and enhance the FG hydrogel stability, and removing these crosslinks enhances permeability and reduces selectivity. Labokha A A et al., *EMBO J* 32: 204 (2013). It is expected that the choice of crosslinking group in the hydrogel may affect biomolecular transport and mechanical properties, as crosslinking controls the mesh size of the gel and the relaxation dynamics of the junction points. These properties can influence the transport of macromolecules interacting with the network chains.

Figure 10:
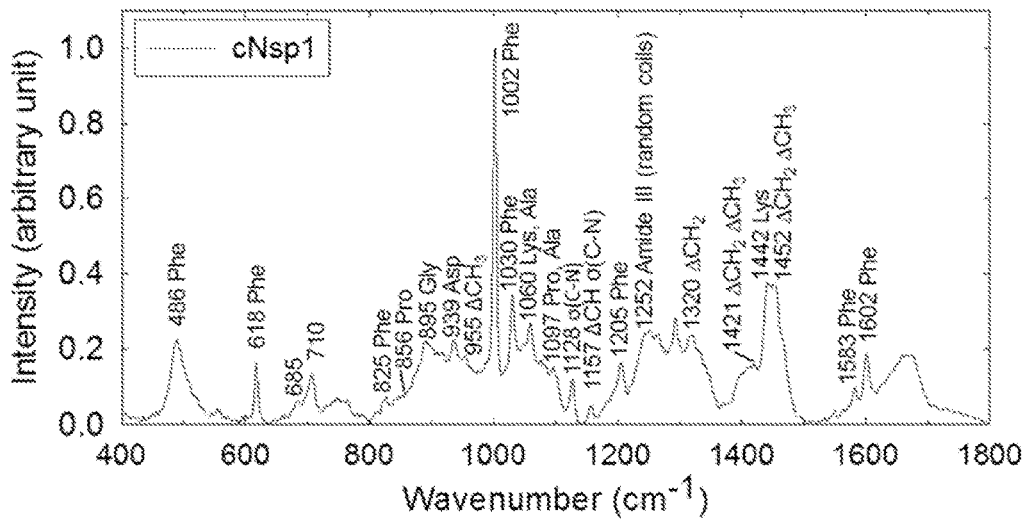
FIG. 10 is a graph depicting Raman spectra of cNsp1 (20 w/v %) with selected band assignments; buffer contained 50 mM Tris/HCl (pH 7.5) and 200 mM NaCl. Δ=deformation; σ=stretching.

Prominent changes in Raman bands upon the addition of hexanediol confirmed that these changes in gel mechanics are caused by disruption of FG repeats involved in molecular interactions within the midblocks, indicating that naturally observed FG interactions have been successfully adapted into the biosynthetic hydrogels. Upon the addition of hexanediol, a significant decrease was observed in the Raman band at 486 cm$^{-1}$ corresponding to a Phe vibrational mode for cNsp1 and both consensus repeat NLP midblocks. Other Phe Raman bands (band assignments in FIG. 10) are similar for all midblock polymers in the presence and absence of the hexanediol (FIG. 7E-G), indicating that natural cNsp1 and synthetic NLPs have a similar physicochemical environment for the Phe residues.

Figure 11:
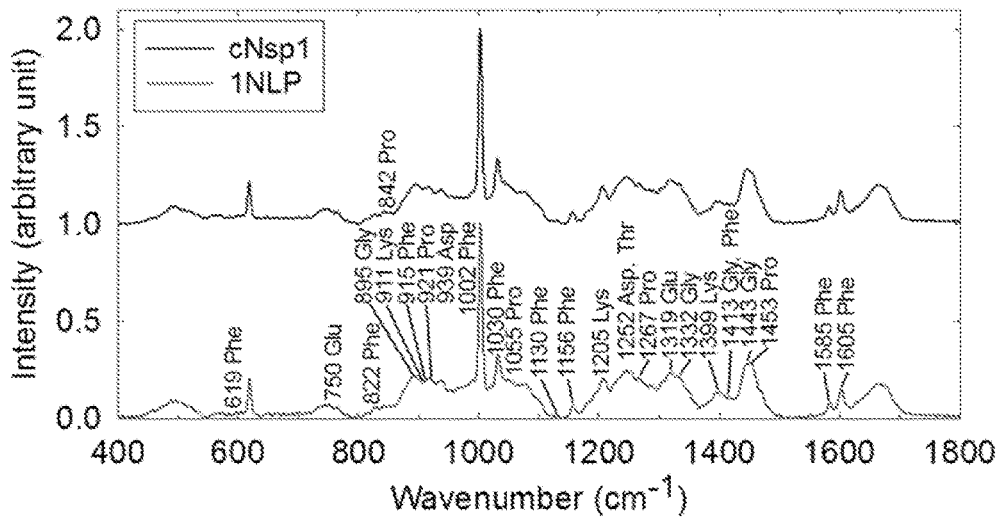
FIG. 11 is a graph depicting Raman spectra of cNsp1 (upper spectrum) and 1NLP (lower spectrum) lyophilized samples with selected band assignments.

Other common changes upon the addition of hexanediol were observed in Raman bands at 685 and 710 cm$^{-1}$. These bands do not appear in lyophilized cNsp1 or NLP (FIG. 11) or in individual amino acids included in NLPs in water solution from a previous study. Zhu G et al., *Spectrochim Acta A Mol Biomol Spectrosc* 78: 1187 (2011). This suggests that the bands are a result of the association between midblocks in water. Molecular interactions between Phe and CH$_3$ and Pro and Lys have been suggested in cNsp1 based upon Nuclear Overhauser Exchange Spectroscopy NMR spectra by Ader et al., *Proc Natl Acad Sci USA* 107: 6281 (2010). The addition of 10% hexanediol suppressed Raman bands responsible for Phe (486 cm$^{-1}$), Pro (856 and 1097 cm$^{-1}$), Lys (1442 cm$^{-1}$), and CH$_3$ (1452 cm$^{-1}$) in cNsp1 (FIG. 7E), consistent with the NMR result,[24] and therefore the observed Raman bands at 685 and 710 cm$^{-1}$ may also relate to those residues.

The similar shifts in the crossover frequency in all designed hydrogels (FIG. 7A-C) and large intensity differences of the 486, 685 and 710 cm$^{-1}$ (FIG. 7E-G) by the addition of hexanediol suggest that hydrophobic interactions, including Phe-mediated associations, between the midblocks exist, similar to the natural Nsp1 hydrogel. These interactions can influence the gel relaxation without contributing significantly to the plateau modulus G' (FIG. 7A-C).

Example 4: Transport Selectivity of Engineered Protein Hydrogels

Engineered protein hydrogels containing cNsp1, 1NLP, and 2NLP midblocks selectively enhanced transport of specific biomolecules into the hydrogels, mimicking the property of natural Nsp1 gels. A fluorescence assay originally established to test recombinant nucleoporin hydrogels was performed in a capillary geometry (FIG. 4A) to test whether cargo-NTR complexes can permeate through the engineered biosynthetic gels with enhanced transport accumulation, while other molecules and cargo without the NTR are significantly retarded.

Figure 12:
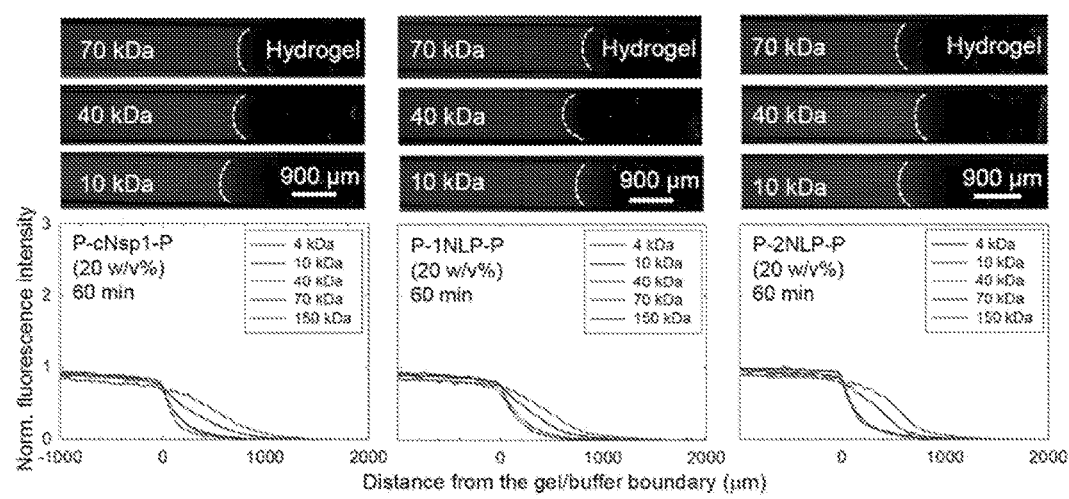
FIG. 12 is a series of three graphs depicting diffusion of various sizes of FITC-dextran through the indicated hydrogels. Gel pore radii are estimated between 2.3 nm and 4.5 nm.
Figure 13A:
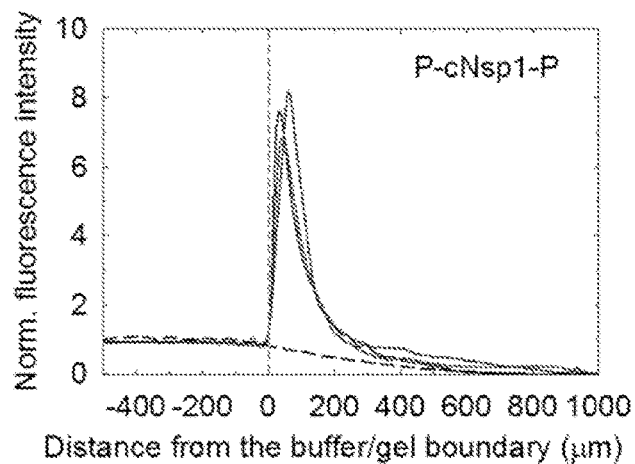
FIG. 13A is a graph depicting permeability profile of the P-cNsp1-P hydrogel for various sizes of FITC-dextran (as per FIG. 12). The florescence intensity profile on the gel at 1 hour is shown. Areas under the solid curves (>0 μm) were calculated and compared to the passive diffusion by inert molecules (dashed curve).
Figure 13B:
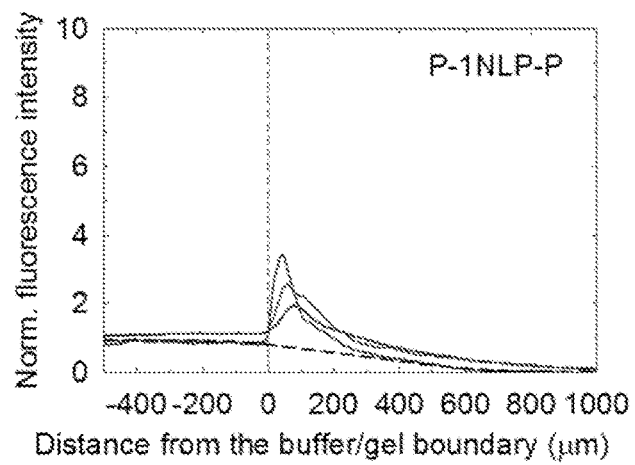
FIG. 13B is a graph depicting permeability profile of the P-1NLP-P hydrogel for various sizes of FITC-dextran (as per FIG. 12). The florescence intensity profile on the gel at 1 hour is shown. Areas under the solid curves (>0 μm) were calculated and compared to the passive diffusion by inert molecules (dashed curve).
Figure 13C:
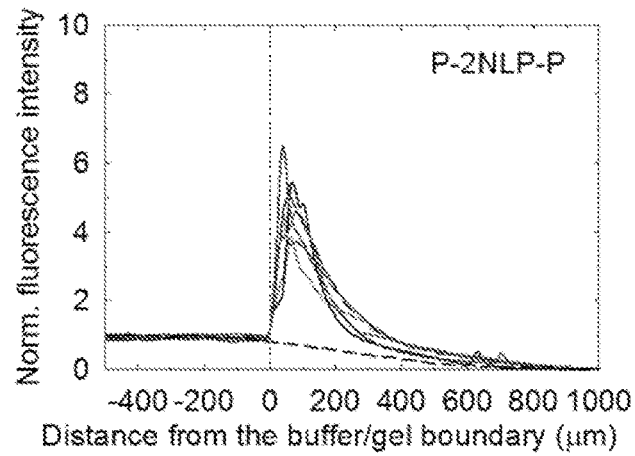
FIG. 13C is a graph depicting permeability profile of the P-2NLP-P hydrogel for various sizes of FITC-dextran (as per FIG. 12). The florescence intensity profile on the gel at 1 hour is shown. Areas under the solid curves (>0 μm) were calculated and compared to the passive diffusion by inert molecules (dashed curve).
Figure 14A:
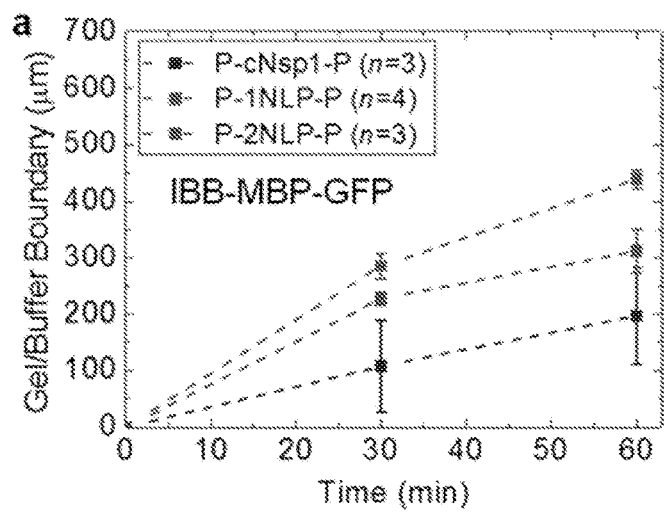
FIG. 14A is a graph depicting indicated gel and buffer interface changes by gel swelling during time lapse measurement of the capillary assay for IBB-MBP-GFP.
Figure 14B:
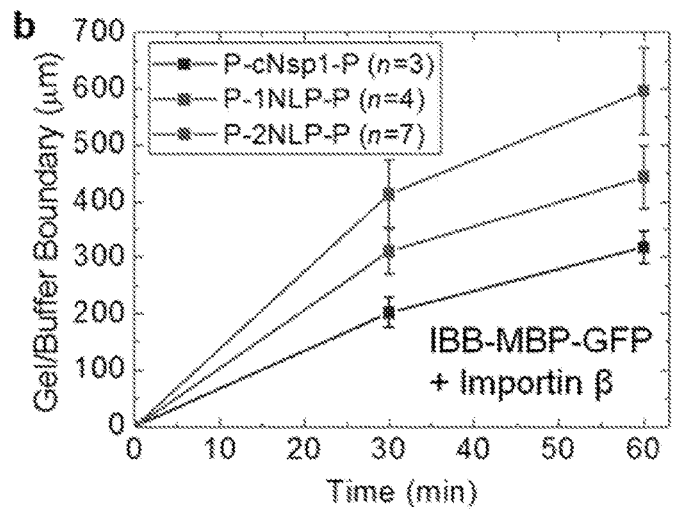
FIG. 14B is a graph depicting indicated gel and buffer interface changes by gel swelling during time lapse measurement of the capillary assay for IBB-MBP-GFP+importin β.

For the assay, importin β (95 kg/mol) was chosen as a NTR due to its well-known binding to cargo with an importin β binding (IBB) domain and to the FG repeat on nucleoporin hydrogels. To reduce the passage of cargo without the NTR and easily quantify the transport of selected cargo, recombinant IBB—maltose binding protein (MBP)—enhanced green fluorescent protein (EGFP) protein fusions were prepared as a model cargo protein (75 kg/mol; Stokes' radii of MBP and GFP are reported as 2.85 nm and 2.42 nm, respectively.). Based on the widely applied dextran diffusion method, it was expected that cargo diffusion into the gel would be significantly reduced since the pore size of the gels is smaller than non-interacting 40 kg/mol dextran probe (4.5 nm of Stokes' radius; FIG. 12). When importin β and the cargo were physically mixed and added to the capillary prepared with the engineered hydrogels, selective partitioning into the hydrogel occurred over time, while a slab diffusion profile was detected in the absence of importin β (FIG. 4B-E and FIG. 13). The enhanced transport into the gel occurred due to a combination of diffusion and convection caused by gel swelling with buffer and cargo complexes (FIG. 14).

Because the length scale of the measurement was much larger than the molecular size and gel mesh size, the gel can be considered as a uniform, semi-infinite slab. The gels can also be treated as macroscopically homogeneous since they are optically clear (absence of inhomogeneity that would scatter on the length scale of visible light) and did not phase separate upon centrifugation. Under these conditions, the permeability coefficient is the product of the diffusivity and solubility coefficients. The discontinuous concentration profile at the interface during the capillary experiments suggested that the cargo-importin β complexes are more soluble in the gel phase than the cargo alone because of the physical association between importin β and FG repeats. This increase in solubility enhances the permeability of the cargo complexes.

Example 5: Electrostatic Effects on Transport Properties

Figure 15:
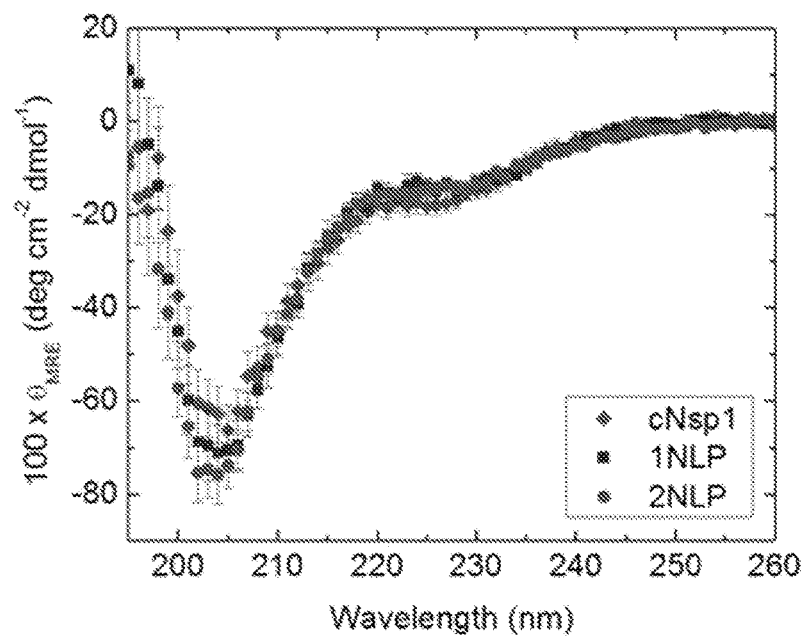
FIG. 15 is a graph depicting circular dichroism (CD) analysis of cNsp1 and indicated NLPs.
Figure 16:
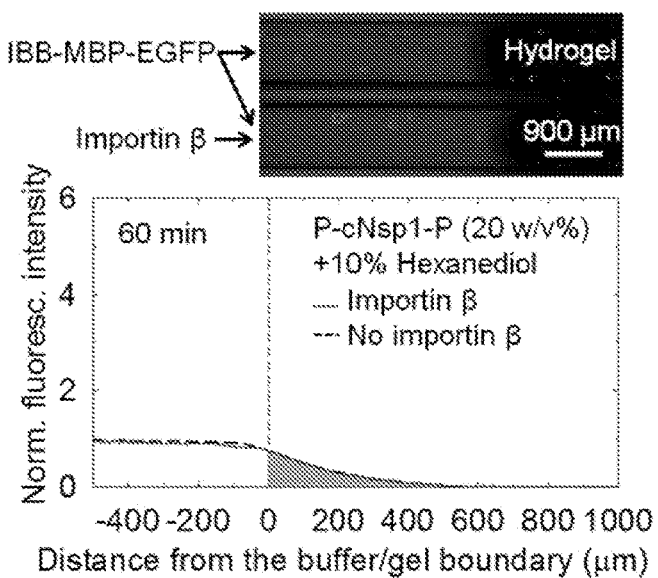
FIG. 16 is a graph depicting permeability profiles of P-cNsp1-P hydrogel (20 w/v %) with 10% 1,6 hexanediol, for IBB-MBP-GFP with or without importin β.
Figure 17A:
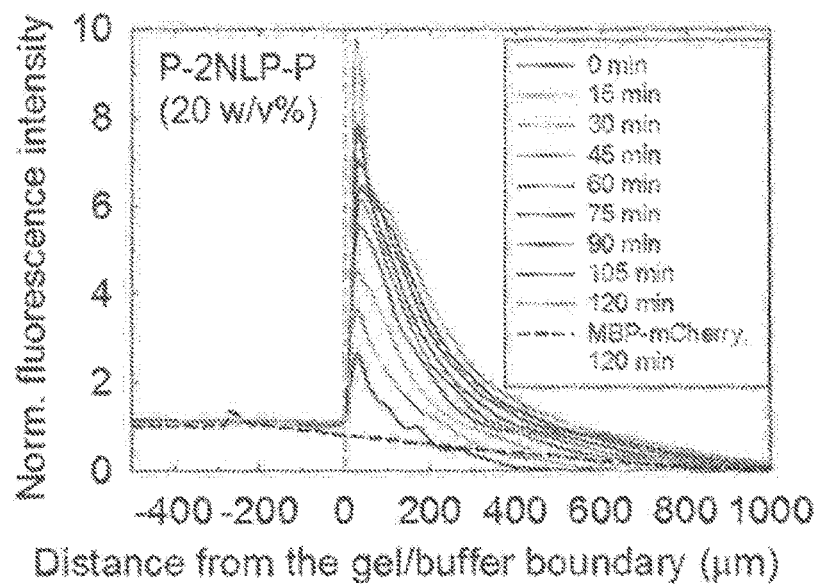
FIG. 17A is a graph depicting time lapse measurements of fluorescence profiles measured to investigate the selective permeability of P-2NLP-P gel (20 w/v %) in the mixture of IBB-MBP-EGFP, MBP-mCherry, and β. Solid curves represent green fluorescence intensity observed in the gel.
Figure 17B:
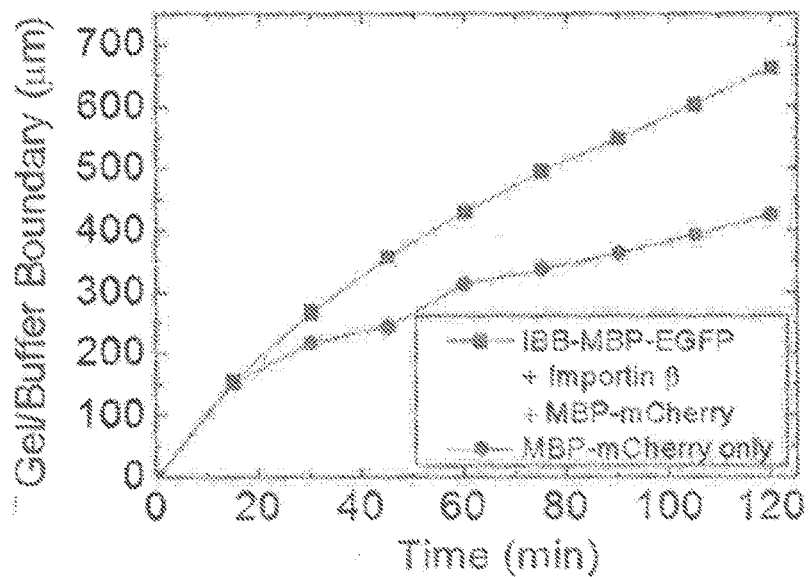
FIG. 17B is a graph depicting movement of the gel/buffer boundary over the course of the selective permeability tests of P-2NLP-P gel (20 w/v %) in the mixture of IBB-MBP-EGFP, MBP-mCherry, and β. For the control experiment, only MBP-mCherry was tested.

The two simplified NLP midblocks, both consensus sequences of cNsp1 but differing by a single amino acid in the repeating peptide, showed quantitative differences in transport properties. When accumulated green fluorescence intensities were calculated compared to the intensities without importin β (FIG. 4F and FIG. 13), the P-2NLP-P gel showed almost twice the intensity of the P-1NLP-P gel. P-cNsp1-P, P-1NLP-P, and P-2NLP-P hydrogels absorbed 3.9±0.4 (mean±SD, n=3), 2.3±0.1 (n=3), and 3.8±0.3 (n=6) times more cargo-importin β complexes than inert molecules in an hour, respectively. Both NLPs have equal numbers of FG repeats, the same P domain crosslinkers for gelation, similar secondary structure as determined by circular dichroism (FIG. 15 and Table 3), and similar passive diffusion profiles for inert molecules over time (dotted black curves in FIG. 4D-E). Therefore, this quantitative change in permeability is believed to originate from the change in the consensus repeat sequence.

TABLE 3

CD analysis of cNsp1 and NLPs[a]

| Protein | Helix 1 | Helix 2 | Strand 1 | Strand 2 | Turns | Unordered | Total | NRMSD |
|---|---|---|---|---|---|---|---|---|
| cNsp1 | 0.00 | 0.02 | 0.18 | 0.11 | 0.14 | 0.54 | 0.99 | 0.125 |
| 1NLP | 0.00 | 0.02 | 0.19 | 0.12 | 0.18 | 0.47 | 0.98 | 0.141 |
| 2NLP | 0.01 | 0.02 | 0.18 | 0.12 | 0.18 | 0.48 | 0.99 | 0.128 |

[a]By the circular dichroism secondary structure (CDSSTR) method (Kang JW et al., *Biomed Opt Express* 2: 2484 (2011)), it was found that approximately 50% structures of all proteins were disordered and others were β-strand and β-turns.

Since the single amino acid change Asp in 1NLP to Ser in 2NLP occurred in the middle of the peptide between FG repeats that are known to bind importin β, the change from an anionic to neutral residue (change from a formal charge of −16 to 0 for the entire midblock of 16 repeats) suggests that electrostatic effects may affect molecular transport. It is interesting to note that the hydrogel made from P-cNsp1-P, where the midblock has a formal charge of +6, shows higher cargo-carrier accumulation on the gel interface than the P-2NLP-P hydrogel (max. fluorescence intensity: 7.6±0.7 and 5.0±0.9 for P-cNsp1-P and P-2NLP-P, respectively). However, the depth-integrated accumulation in an hour is the same for both materials (FIG. 4F), indicating that the P-2NLP-P gel has better permeability to the cargo-carrier than P-cNsp1-P gel.

Changes in the charge of the protein based on a single substitution per repeat unit between 1NLP and 2NLP affect biomolecular transport through the designed hydrogels, despite the use of high ionic strength buffers that screen charge as under physiological conditions. Recent studies of related biological hydrogels such as mucus and cartilage have similarly observed that electrostatic effects influence molecular transport at the physiologically relevant ionic strength conditions. Selective binding can be added to synthetic systems by conjugating FG peptide onto polymer gels. The results presented here on NLP hydrogels indicate that not only FG sequences but also residues far from the FG repeat can play an important role in the performance of nuclear pore-mimetic synthetic hydrogels.

Example 6: Further Characterization of P-2NLP-P

After identifying P-2NLP-P as the top performing construct, additional experiments were performed to explore its performance. The addition of 10% hexanediol to disrupt FG interactions eliminated selective accumulation of cargo complexes in P-2NLP-P gels (FIG. 4G), showing that FG repeat interactions are involved in enhanced selective transport in the biosynthetic hydrogels. This indicates that the engineered hydrogels have a filtering mechanism similar to the natural nucleoporin system.

Using blends of model proteins with and without the IBB domain established the ability of the biosynthetic NLP gels to actively transport cargo proteins compared to the inert proteins. A model cargo protein incapable of binding importin β, MBP-mCherry (67 kg/mol), has smaller size than IBB-MBP-EGFP (75 kg/mol) but showed retarded transport through the biosynthetic NLP hydrogels even in the presence of importin β (FIG. 4H-I, 3 hours assay in 10 w/v % and 20 w/v % of P-2NLP-P gel results in FIG. 5).

FIG. 4H-I shows selective permeability test performed on P-1NLP-P and P-2NLP-P biosynthetic hydrogels (20 w/v %) with the addition of 5 μM MBP-mCherry, a model inert molecule, into 5 μM IBB-MBP-EGFP/importin β cargo complex mixtures. Over an hour, the cargo-carrier complexes accumulated 3.0 and 5.3 times more than MBP-mCherry (without the IBB domain) in P-1NLP-P and P-2NLP-P hydrogels, respectively.

Figure 5A:
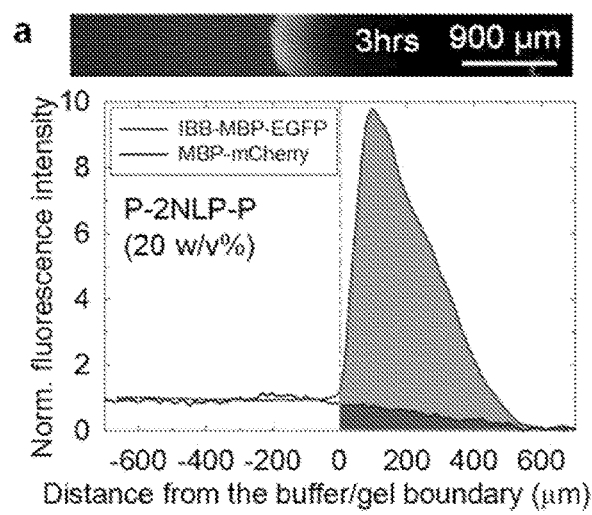
FIG. 5A is a graph depicting selective permeability of P-2NLP-P gel in 20 w/v %
Figure 5B:
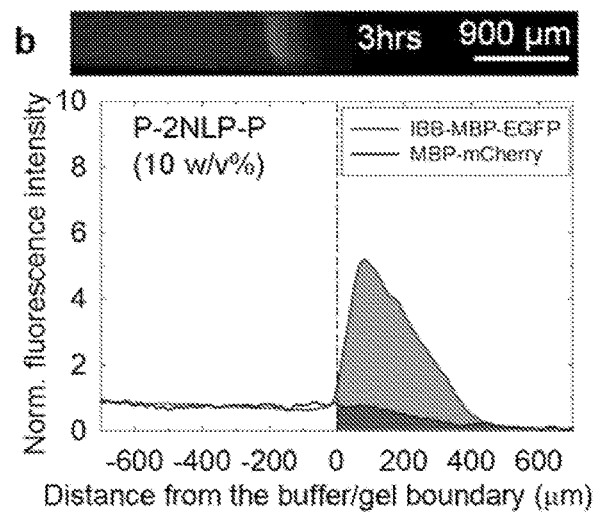
FIG. 5B is a graph depicting selective permeability of P-2NLP-P gel in 10 w/v %.

When hydrated in buffer at 20% and 10%, P-2NLP-P formed optically-clear gels that did not phase separate upon centrifugation, suggesting they formed macroscopically homogeneous networks under these conditions. FIG. 5 shows that over three hours, the cargo-carrier complexes accumulated in the gel 10.2 and 5.2 times more than MBP-mCherry (no IBB domain), indicating that the 10 w/v % gel still showed enhanced transport of the selected biomolecules and the total accumulation depended on the number of FG sequences in the hydrogels (i.e., there are twice as many FG sequences in the 20 w/v % gel compared to the 10 w/v % gel).

The results illustrate that the designed hydrogels can mimic both the selectivity and enhanced transport of natural nucleoporin hydrogels.

Example 7: NTR-Mediated Selective Uptake of a Target Molecule

Figure 18:
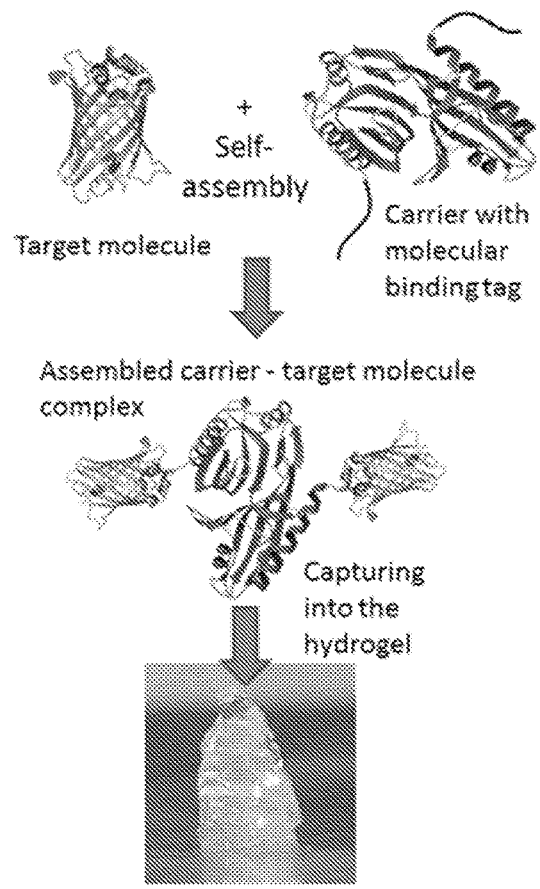
FIG. 18 is a schematic depicting a method for selective capture of a target molecule by a hydrogel of the invention.

This example illustrates a generalizable method for capturing selected molecules into a hydrogel of the invention. As shown in FIG. 18, a peptide tag which can associate with a target molecule of interest can be genetically fused to a nuclear transport receptor (NTR). In a solution, the peptide tag fused to NTR will recognize, i.e., associate with, its target molecule and thereby spontaneously form NTR-peptide tag-target molecule complexes. Due to the interaction between NTR and the hydrogel, the NTR-peptide tag-target molecule complex is captured by and carried into the hydrogel.

As a model system, incomplete green fluorescent protein (GFP) was used as a target molecule and GFP tag as a binding peptide tag. It is known that complete GFP can be constructed by mixing incomplete GFP and the GFP tag, with green fluorescence as evidence of the assembly. Cabantous S et al., *Nat Methods* 3: 845-854 (2006); Kent K P et al., *J Am Chem Soc* 130: 9664-9665 (2008). Another benefit using GFP as a model is that green fluorescence can be used to visualize selective transport of the NTR-GFP tag-incomplete GFP (i.e., NTR-GFP) complex into the hydrogel under a fluorescence microscope.

GFP tag was genetically fused to the C-terminus of the NTR nuclear transport factor 2 (NTF2). Since NTF2 is homodimer, each NTF2 has two GFP tags. For protein purification, 6×Histidine tag (SEQ ID NO: 30) was also fused between NTF2 and GFP tag (NTF2-His tag-GFP tag). After protein synthesis, more than 50 mg of chimeric NTF2-GFP tag was obtained.

Figures 19A, 19B, 19C, 19D, 19E, 19F:
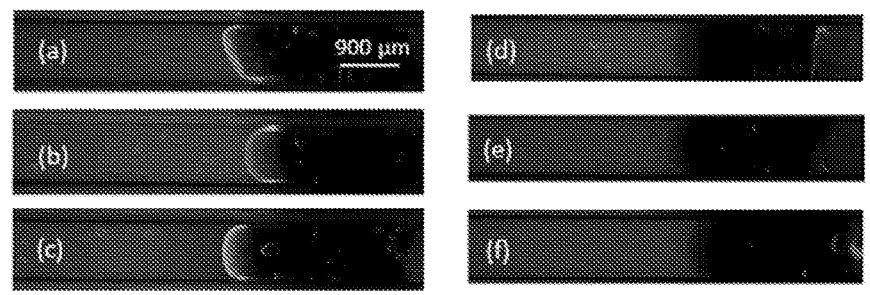
FIG. 19A is a photographic image depicting NTF2-GFP in P-2NLP-P.
FIG. 19B is a photographic image depicting NTF2-GFP in P-1NLP-P.
FIG. 19C is a photographic image depicting NTF2-GFP in P-cNsp1-P.
FIG. 19D is a photographic image depicting 40 kg/mol FITC-dextran in P-2NLP-P.
FIG. 19E is a photographic image depicting 40 kg/mol FITC-dextran in P-1NLP-P.
FIG. 19F is a photographic image depicting 40 kg/mol FITC-dextran in P-cNsp1-P.

Capillary transport assay validated the method and confirmed that the hydrogel system can capture selected molecules into the hydrogel. When NTF2 with GFP tag was mixed with incomplete GFP, the solution turned from no color to light green after overnight incubation. When the solution was added to one end of a capillary where 20 wt % hydrogel filled the other end (FIG. 19), the green fluorescence was accumulated onto the hydrogel over time (FIGS. 19A-19C). In the same experimental conditions, fluorescein-labeled dextran (40 kg/mol, hydrodynamic radius: 4.5 nm) did not get into the hydrogel (FIGS. 19D-19F).

One or two incomplete GFP can associate with NTF2-GFP tag homodimer which has two GFP tags. The molar mass of GFP is approximately 30 kg/mol (2.42 nm hydrodynamic radius). The molar mass of NTF2-GFP tag homodimer is 36 kg/mol. Since NTF2-GFP complex (66 kg/mol with one GFP, or 96 kg/mol with two GFP) is greater than the 40 kg/mol dextran, the results clearly show that the synthetic system can mimic the natural selective filtering nuclear pore function which is carrying target molecule into the gel although the size of the NTF2-GFP complex is greater than uncomplexed inert reference molecules.

The method just described opens new avenues for numerous applications for a number of applications, including for example drug delivery, food toxicology, and defense. Researchers have developed peptide library for various target molecules using phage display, and solid phase peptide synthesis techniques. By simply fusing those peptides to NTR carriers, the carriers will capture the targets and bring them into the hydrogels. More and diverse peptides will be available for specific target molecules with time; thereby, the method will be further generalized. As a specific example, Staphylococcal enterotoxin B (SEB) toxoid can be captured into the hydrogel using anti-SEB tag fused to NTF2 or importin β; the hydrogel can then be removed or destroyed for environmental decontamination.

INCORPORATION BY REFERENCE

All patents and published patent applications mentioned in the description above are incorporated by reference herein in their entirety.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

We claim:

1. A polypeptide comprising a plurality of contiguous instances of the sequence of PAFSFGAKPDEKKDSDTSK (SEQ ID NO: 1), wherein the polypeptide forms a hydrogel.

2. The polypeptide of claim 1, further comprising a first leucine zipper domain endblock, wherein the first leucine zipper domain endblock flanks the N-terminal end at the plurality of contiguous instances of the sequence of SEQ ID NO:1 or flanks the C-terminal end of the plurality of contiguous instances of the sequence of SEQ ID NO:1.

3. The polypeptide of claim 2, wherein the first leucine zipper domain endblock consists of a pentameric coiled-coil domain (P domain).

4. The polypeptide of claim 3, wherein the P domain consists of the peptide represented by APQMLRELQETNAALQDVRELLRQQVKEITFLKNTVMESDAS (SEQ ID NO:3).

5. The polypeptide of claim 1, further comprising a first leucine zipper domain endblock flanking the N-terminal end of the plurality of contiguous instances of the sequence of SEQ ID NO:1; and a second leucine zipper domain endblock flanking the C-terminal end of the plurality of contiguous instances of the sequence of SEQ ID NO:1.

6. The polypeptide of claim 5, wherein at least one of the first or second leucine zipper domain endblock consists of a P domain.

7. The polypeptide of claim 6, wherein the P domain consists of the peptide of APQMLRELQETNAALQDVRELLRQQVKEITFLKNTVMESDAS (SEQ ID NO:3).

8. The polypeptide of claim 1, comprising the sequence: APQMLRELQETNAALQDVRELLRQQVKEITFLKNTVMESDASGASPAFSFGAKPDEKK DSDTSKPAFSFGAKPDEKKDSDTSKPAFSFGAKPDEKKDSDTSKPAFSFGAKPDEKKDS DTSKPAFSFGAKPDEKKDSDTSKPAFSFGAKPDEKKDSDTSKPAFSFGAKPDEKKDSDTS KPAFSFGAKPDEKKDSDTSKTSPAFSFGAKPDEKKDSDTSKPAFSFGAKPDEKKDSDTSK PAFSFGAKPDEKKDSDTSKPAFSFGAKPDEKKDSDTSKPAFSFGAKPDEKKDSDTSKPAF SFGAKPDEKKDSDTSKPAFSFGAKPDEKKDSDTSKPAFSFGAKPDEKKDSDTSKTSAPQ MLRELQETNAALQDVRELLRQQVKEITFLKNTVMESDAS (SEQ ID NO:4).

9. A polypeptide comprising a plurality of contiguous instances of the sequence of PAFSFGAKPDEKKDDDTSK (SEQ ID NO: 2), wherein the polypeptide forms a hydrogel.

10. The polypeptide of claim 9, further comprising a first leucine zipper domain endblock, wherein the first leucine zipper domain endblock flanks the N-terminal end of the plurality of contiguous instances of the sequence of SEQ ID NO:2 or flanks the C-terminal end of the plurality of contiguous instances of the sequence of SEQ ID NO:2.

11. The polypeptide of claim 10, wherein the first leucine zipper domain endblock consists of a pentameric coiled-coil domain (P domain).

12. The polypeptide of claim 11, wherein the P domain consists of the peptide of APQMLRELQETNAALQDVRELLRQQVKEITFLKNTVMESDAS (SEQ ID NO:3).

13. The polypeptide of claim 9, further comprising a first leucine zipper domain endblock flanking the N-terminal end of the plurality of contiguous instances of the sequence of SEQ ID NO:2; and a second leucine zipper domain endblock flanking the C-terminal end of the plurality of contiguous instances of the sequence of SEQ ID NO:2.

14. The polypeptide of claim 13, wherein at least one of the first or second leucine zipper domain endblock consists of a P domain.

15. The polypeptide of claim 14, wherein the P domain consists of the peptide represented by APQMLRELQETNAALQDVRELLRQQVKEITFLKNTVMESDAS (SEQ ID NO:3).

16. The polypeptide of claim 9, comprising the sequence: APQMLRELQETNAALQDVRELLRQQVKEITFLKNTVMESDASGASPAFSFGAKPDEKK DDDTSKPAFSFGAKPDEKKDDDTSKPAFSFGAKPDEKKDDDTSKPAFSFGAKPDEKKDD DTSKPAFSFGAKPDEKKDDDTSKPAFSFGAKPDEKKDDDT SKPAFSFGAKPDEKKDDDTSKTSPAFSFGAKPDEKKDDDTSKPAFSFGAKPDEKKDDDT SKPAFSFGAKPDEKKDDDTSKPAFSFGAKPDEKKDDDTSKPAFSFGAKPDEKKDDDTSK PAFSFGAKPDEKKDDDTSKPAFSFGAKPDEKKDDDTSKTS APQMLRELQETNAALQDVRELLRQQVKEITFLKNTVMESDAS (SEQ ID NO:5).

17. A nucleic acid molecule encoding the polypeptide of claim 1.

18. An expression vector comprising the nucleic acid molecule of claim 17.

19. A cell, comprising the expression vector of claim 18.

20. A hydrogel, comprising the polypeptide of claim 1.

21. A filtering device, comprising the hydrogel of claim 20; and a housing or support for the hydrogel.

22. A drug delivery device, comprising a drug; and the hydrogel of claim 20.

23. A method of separating or selectively filtering macromolecules, comprising contacting a source of macromolecules with a hydrogel of claim 20.

* * * * *